(12) United States Patent
Velaparthi et al.

(10) Patent No.: US 8,415,340 B2
(45) Date of Patent: Apr. 9, 2013

(54) TRIAZINE KINASE INHIBITORS

(75) Inventors: Upender Velaparthi, Cheshire, CT (US); Peiying Liu, Madison, CT (US); Mark D. Wittman, Wallingford, CT (US); David R. Langley, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/670,257

(22) PCT Filed: Jul. 24, 2008

(86) PCT No.: PCT/US2008/070961
§ 371 (c)(1),
(2), (4) Date: Jan. 22, 2010

(87) PCT Pub. No.: WO2009/015254
PCT Pub. Date: Jan. 29, 2009

(65) Prior Publication Data
US 2010/0197654 A1   Aug. 5, 2010

Related U.S. Application Data

(60) Provisional application No. 60/951,806, filed on Jul. 25, 2007, provisional application No. 60/970,314, filed on Sep. 6, 2007.

(51) Int. Cl.
| | |
|---|---|
| *A61K 31/53* | (2006.01) |
| *A61K 31/535* | (2006.01) |
| *A61K 31/55* | (2006.01) |
| *A61K 31/54* | (2006.01) |
| *A61K 31/554* | (2006.01) |
| *C07D 403/04* | (2006.01) |
| *C07D 279/10* | (2006.01) |
| *C07D 267/02* | (2006.01) |
| *C07D 243/08* | (2006.01) |
| *C07D 417/04* | (2006.01) |
| *C07D 413/04* | (2006.01) |

(52) U.S. Cl.
USPC ............... 514/210.18; 514/211.15; 514/218; 514/227.8; 514/236.2; 514/245; 540/544; 540/575; 544/60; 544/113; 544/198; 544/58.2

(58) Field of Classification Search ............. 514/210.18, 514/236.2, 245, 218, 227.8, 211.15; 540/544, 540/575; 544/113, 198, 58.2, 60
See application file for complete search history.

(56) References Cited

FOREIGN PATENT DOCUMENTS

| | | |
|---|---|---|
| EP | 1479397 | 11/2004 |
| WO | WO 00/25780 | 5/2000 |
| WO | 01/25220 | * 4/2001 |
| WO | WO 01/25220 | 4/2001 |
| WO | WO 02/22603 | 3/2002 |
| WO | WO 2004/031184 | 4/2004 |
| WO | WO 2005/028467 | 3/2005 |
| WO | WO 2006/072831 | 7/2006 |

* cited by examiner

*Primary Examiner* — James O Wilson
*Assistant Examiner* — Ebenezer O Sackey
(74) *Attorney, Agent, or Firm* — Elliott Korsen

(57) ABSTRACT

The invention provides compounds of formula I

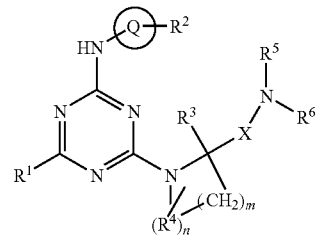

(I)

and pharmaceutically acceptable salts thereof.
The formula I compounds inhibit tyrosine kinase activity thereby making them useful as anticancer agents.

14 Claims, No Drawings

TRIAZINE KINASE INHIBITORS

FIELD OF THE INVENTION

This invention relates to novel triazine compounds that are useful as anti-cancer agents. This invention also relates to pharmaceutical compositions containing the compounds and methods of using the compounds for the treatment of proliferative and other diseases, in particular, certain types of cancer.

BACKGROUND

The invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G. et al., "Signaling Targets for the Development of Cancer Drugs", *Anti-Cancer Drug Design*, 9:263-277 (1994); Merenmies, J. et al., "Receptor Tyrosine Kinase Signaling in Vascular Development" *Cell Growth Differ*, 8:3-10 (1997); Shawver, L. K. et al., "Receptor Tyrosine Kinases as Targets for Inhibition of Angiogenesis", *Drug Discovery Today*, 2:50-63 (1997); all herein incorporated by reference).

Tyrosine kinases play a critical role in signal transduction for several cellular functions including cell proliferation, carcinogenesis, apoptosis, and cell differentiation Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The invention provides compounds of Formula I, including stereoisomers, tautomers and pharmaceutically acceptable salts thereof, which are useful as inhibitors of tyrosine kinase enzymes.

The invention also provides pharmaceutical compositions comprising a pharmaceutically acceptable carrier and one or more of the compounds of the present invention or a stereoisomer, tautomer or pharmaceutically acceptable salt thereof.

The invention also provides a method for treating a condition associated with one or more tyrosine kinase inhibitors comprising administering to a patient in need of such treatment, a therapeutically effective amount of a compound of formula I or a stereoisomer, tautomer or pharmaceutically acceptable salt thereof, and optionally one or more other anticancer agent or treatment.

The invention also provides methods for treating cancer using the compounds of the invention or a stereoisomer, tautomer or pharmaceutically acceptable salt thereof.

The invention also provides the compounds of the present invention or a stereoisomer, tautomer or pharmaceutically acceptable salt thereof, for use in therapy.

The present invention also provides the use of the compounds of the present invention or a stereoisomer, tautomer or pharmaceutically acceptable salt thereof, for the manufacture of a medicament for the treatment of a proliferative disease such as cancer.

These and other features of the invention will be set forth as the disclosure continues.

DETAILED DESCRIPTION OF THE INVENTION

The invention provides for compounds of formula I, pharmaceutical compositions employing such compounds and for methods of using such compounds.

In accordance with the invention, there are disclosed compounds of formula I

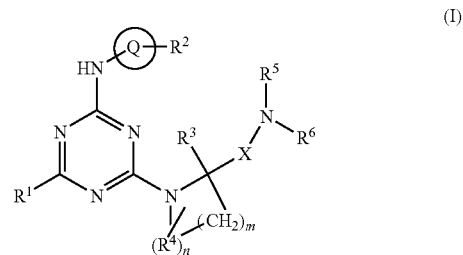

wherein:

Q is aryl, substituted aryl, heteroaryl or substituted heteroaryl;

X is C=O, C=S or $CH_2$;

$R^1$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^2$ is hydrogen, alkyl, substituted alkyl, cycloalkyl or substituted cycloalkyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ and $R^6$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

m is 1, 2 or 3;

n is 0, 1, 2, 3 or 4;

or a pharmaceutically acceptable salt, tautomer or stereoisomer thereof.

In accordance with the invention, there are disclosed compounds of formula Ia

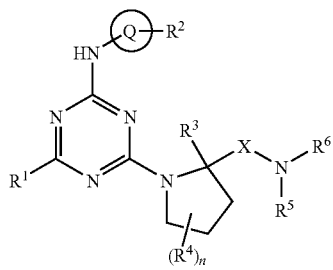

(Ia)

wherein:

Q is heteroaryl or substituted heteroaryl;

X is C=O or C=S;

$R^1$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^2$ is hydrogen, alkyl, substituted alkyl, cycloalkyl or substituted cycloalkyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ is hydrogen;

$R^6$ is hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

n is 0, 1, 2, 3 or 4;

or a pharmaceutically acceptable salt, tautomer or stereoisomer thereof.

In another aspect of the invention, there are disclosed compounds of formula Ia

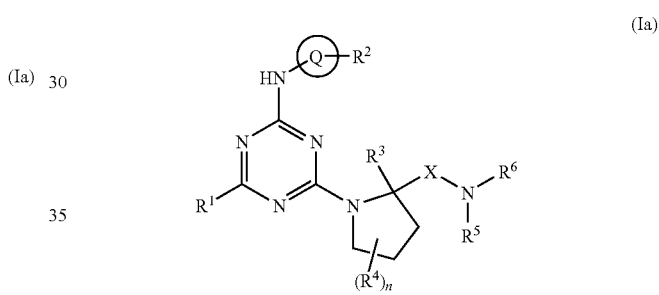

(Ia)

wherein:

Q is heteroaryl;

X is C=O;

$R^1$ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^2$ is hydrogen, alkyl, substituted alkyl, cycloalkyl or substituted cycloalkyl;

$R^3$ is hydrogen, alkyl or substituted alkyl;

R⁴ is independently one or more hydrogen, alkyl, substituted alkyl, hydroxy, alkoxy, halogen, haloalkyl, haloalkoxy, cycloalkyl or substituted cycloalkyl;

R⁵ is hydrogen;

R⁶ is hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or R⁵ and R⁶ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

n is 0, 1 or 2;

or a pharmaceutically acceptable salt, tautomer or stereoisomer thereof.

In a further aspect of the invention, there are disclosed compounds of formula Ia

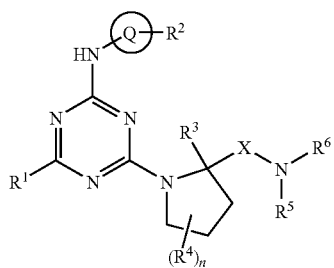

wherein:

Q is pyrazole or imidazole;

X is C=O;

R¹ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

R² is hydrogen, alkyl, substituted alkyl, cycloalkyl or substituted cycloalkyl;

R³ is hydrogen, alkyl or substituted alkyl;

R⁴ is independently one or more hydrogen, alkyl, substituted alkyl, hydroxy, alkoxy, halogen, haloalkyl, haloalkoxy, cycloalkyl or substituted cycloalkyl;

R⁵ is hydrogen;

R⁶ is pyridine, substituted pyridine, pyrazine, substituted pyrazine, thiadiazole, thiazole; substituted thiazole, piperidine or substituted piperidine, or R⁵ and R⁶ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring, n is 0, 1 or 2;

or a pharmaceutically acceptable salt, tautomer or stereoisomer thereof.

In another aspect of the invention, there are disclosed compounds of formula II

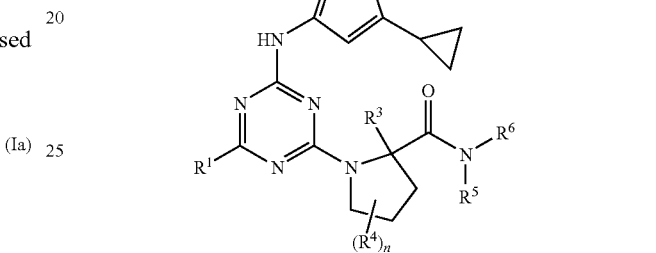

wherein:

R¹ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

R³ is hydrogen, alkyl or substituted alkyl;

R⁴ is independently one or more hydrogen, alkyl, substituted alkyl, hydroxy, alkoxy, halogen, haloalkyl, haloalkoxy, cycloalkyl or substituted cycloalkyl;

R⁵ is hydrogen;

R⁶ is pyridine, substituted pyridine, pyrazine, substituted pyrazine, thiadiazole, thiazole; substituted thiazole, piperidine or substituted piperidine, or R⁵ and R⁶ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring, n is 0, 1 or 2;
or a pharmaceutically acceptable salt, tautomer or stereoisomer thereof.

In yet another aspect of the invention, there are disclosed compounds of formula III

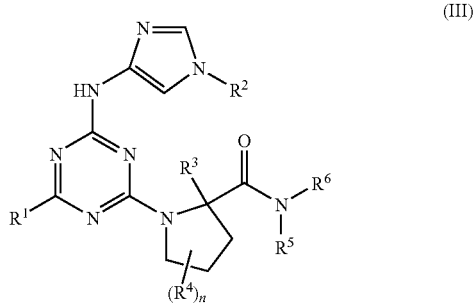

wherein:
R¹ is hydrogen, alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

R² is hydrogen, alkyl, substituted alkyl, cycloalkyl or substituted cycloalkyl;

R³ is hydrogen, alkyl or substituted alkyl;

R⁴ is independently one or more hydrogen, alkyl, substituted alkyl, hydroxy, alkoxy, halogen, haloalkyl, haloalkoxy, cycloalkyl or substituted cycloalkyl;

R⁵ is hydrogen;

R⁶ is pyridine, substituted pyridine, pyrazine, substituted pyrazine, thiadiazole, thiazole; substituted thiazole, piperidine or substituted piperidine, or R⁵ and R⁶ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring, n is 0, 1 or 2;
or a pharmaceutically acceptable salt, tautomer or stereoisomer thereof.

In another embodiment the present invention provides a pharmaceutical composition comprising a pharmaceutically acceptable carrier and one or more of the compounds of the present invention or a stereoisomer, tautomer or pharmaceutically acceptable salt thereof.

In another embodiment the present invention provides a pharmaceutical composition comprising a pharmaceutically acceptable carrier and a therapeutically effective amount of one or more of the compounds of the present invention or a stereoisomer, tautomer or pharmaceutically acceptable salt thereof.

In another embodiment the present invention provides a method for treating protein kinase related disorders comprising administering to a patient in need of such treatment a therapeutically effective amount of one or more of the compounds of the present invention or a stereoisomer, tautomer or pharmaceutically acceptable salt thereof.

In another embodiment the present invention provides a method for treating tyrosine kinase related disorders comprising administering to a patient in need of such treatment a therapeutically effective amount of one or more of the compounds of the present invention or a stereoisomer, tautomer or pharmaceutically acceptable salt thereof.

In another embodiment, the protein kinase related disorder is selected from the group consisting of cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

In another embodiment, the present invention provides a method of treating a patient in need of protein kinase related disorder treatment, comprising administering a compound of the present invention or a stereoisomer, tautomer or pharmaceutically acceptable salt thereof in an amount effective to treat a protein kinase related disorder.

In another embodiment, the present invention provides a pharmaceutical composition further comprising one or more additional anticancer agent or treatment, such as radiation therapy.

In another embodiment, the present invention provides a compound of the present invention for use in therapy.

In another embodiment, the present invention provides a compound of the present invention for use in therapy for treating a protein kinase related disorder.

In another embodiment, the present invention provides a compound of the present invention for use in therapy for treating a tyrosine kinase related disorder.

In another embodiment, the present invention also provides the use of a compound of the present invention for the manufacture of a medicament for the treatment of a protein kinase related disorder.

In another embodiment, the present invention also provides the use of a compound of the present invention for the manufacture of a medicament for the treatment of a tyrosine kinase related disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a protein kinase related disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" or "alkylene" refers to both branched and straight-chain saturated aliphatic hydrocarbon groups of 1 to 20 carbon atoms, preferably 1 to 7 carbon atoms. The expression "lower alkyl" refers to unsubstituted alkyl groups of 1 to 4 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., $SO_2NH_2$, substituted sulfonamido, nitro, cyano, carboxy, carbamyl, e.g., $CONH_2$, substituted carbamyl e.g., CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where it is noted above that the substituent is further substituted, it will be with alkyl, alkoxy, aryl or arylalkyl.

The term "alkenyl" or "alkenylene" refers to hydrocarbon chains of either a straight or branched configuration having the specified number of carbon atoms and one or more unsaturated carbon-carbon bonds which may occur in any stable point along the chain. These may be groups of 2 to 20 carbon atoms, preferably 2 to 15 carbon atoms, and most preferably 2 to 8 carbon atoms, having one to four double bonds. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" or "alkynylene" refers to hydrocarbon chains of either a straight or branched configuration and one or more carbon-carbon triple bonds which may occur in any stable point along the chain. These may include groups of 2 to 20 carbon atoms, preferably 2 to 15 carbon atoms, and most preferably 2 to 8 carbon atoms, having one to four triple bonds. Examples of alkynyl include, but are not limited to s ethynyl, propynyl, butynyl, pentynyl, hexynyl and the like.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g., imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "alkoxy" or "alkyloxy" refers to an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

The term "halogen" or "halo" refers to fluorine, chlorine, bromine and iodine.

The term "haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "carbocyclic ring" or "carbocyclyl" refers to stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

The term "bicyclic carbocycle" or "bicyclic carbocyclic group" refers to a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkylsulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like.

Exemplary substituents include one or more alkyl or arylalkyl groups as described above or one or more groups described above as alkyl substituents.

The terms "heterocycle", "heterocyclic" and "heterocyclyl" refer to an optionally substituted, saturated, partially unsaturated or fully unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized to —NO—, —SO—, or —SO$_2$— and the nitrogen heteroatoms may also optionally be quaternized. The heterocyclic group may be attached at any heteroatom or carbon atom. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "heteroatoms" shall include oxygen, sulfur and nitrogen.

The term "alkylsulfone" refers to —R$^k$S(=O)$_2$R$^k$, wherein R$^k$ is an alkyl or substituted alkyl.

The term "oxo" refers to the divalent radical =O.

The term "carbamate" refers to the group —OC(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —C(=O)NR$^m$R$^n$ wherein R$^m$ and R$^n$ are independently selected from H, alkyl, substituted alkyl, alkenyl, substituted alkenyl, cycloalkyl, and substituted cycloalkyl, provided at least one of R$^m$ or R$^n$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —OC(=O)NR$^q$R$^r$ wherein R$^q$ and R$^r$ are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SR$^s$ where R$^s$ is an alkyl, substituted alkyl, cycloalkyl, or substituted cycloalkyl.

The term "thioalkyl" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^x$, and/or —OC(=O)NR$^y$R$^z$, wherein R$^y$ and R$^z$ are independently selected from alkyl and substituted alkyl.

The group —NR$^6$(C=O)R$^9$ refers to a group where R$^6$ is selected from hydrogen, lower alkyl and substituted lower alkyl, and R$^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

The compounds of formula I may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed according to methods known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:

a) *Design of Prodrugs*, edited by H. Bundgaard (Elsevier, 1985), and *Methods in Enzymology*, Vol. 112, at pp. 309-396, edited by K. Widder et al. (Academic Press, 1985);

b) *A Textbook of Drug Design and Development*, edited by Krosgaard-Larsen and H. Bundgaard, Chapter 5, "Design and Application of Prodrugs", by H. Bundgaard, at pp. 113-191 (1991);

c) H. Bundgaard, *Advanced Drug Delivery Reviews*, 8:1-38 (1992);

d) Bundgaard, H. et al., *Journal of Pharmaceutical Sciences*, 77:285 (1988); and e) Kakeya, N. et al., *Chem Phar Bull.*, 32:692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include C$_{1-6}$alkyl, C$_{1-6}$alkylbenzyl, 4-methoxybenzyl, indanyl, phthalyl, methoxymethyl, C$_{1-6}$ alkanoyloxy-C$_{1-6}$alkyl, e.g., acetoxymethyl, pivaloyloxymethyl or propionyloxymethyl, C$_{1-6}$alkoxycarbonyloxy-C$_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, King, F. D., ed., The Royal Society of Chemistry, Cambridge, UK (1994), which is incorporated herein by reference in its entirety.

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-thrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa. (1985), which is incorporated herein by reference in its entirety.

Utility

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

Further, another aspect of the invention provides for the use of a compound of formula I or a pharmaceutically acceptable salt thereof in the manufacture of a medicament for use in the treatment of certain types of cancer including cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecule compounds such as ZD6474 and SU6668; Vatalanib, Nexavar® (Sorafenib tosylate), Sutent® (sunitinib malate), CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; protein tyrosine kinase inhibitors such as, e.g., Gleevec® (imatinib mesylate) and dasatinib Sprycel (dasatinib), Casodex® (bicalutamide), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists, e.g., 6-thioguanine and 6-mercaptopurine; glutamine antagonists, e.g., DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anti-cancer or cytotoxic agents when a combination formulation is inappropriate. The invention is not limited in the sequence of administration; compounds of formula I may be administered either prior to or after administration of the known anti-cancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

A. CDK 2/cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM $MgCl_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM $MgCl_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 200 µM, FL-peptide, 1.5 µM; FLT3, 4.5 nM and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 µl prepared from 15 µl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of GSK3-β with substrates and test compounds. The reaction was incubated at room temperature for 60 min. and terminated by adding 30 µl of 35 mM EDTA to each sample. The reaction mixture was analyzed on the Caliper LabChip 3000 (Caliper, Hopkinton, Mass.) by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 30 µM; FL-GSK substrate, 1.5 µM; His-GSK3B, 2.4 nM; and DMSO, 1.6%.

D. IGF1-Receptor Tyrosine Kinase Assay

The assays were performed in U-bottom 384-well plates. The final assay volume was 30 µl prepared from 15 µl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the above assay. The following results were obtained.

TABLE I

| IGF-1R in vitro kinase IC50 (uM) | |
| --- | --- |
| Example No. | IGF1R kinase $IC_{50}$ (uM) |
| 87 | 0.002 |
| 62 | 0.002 |
| 46 | 0.003 |
| 25 | 0.003 |
| 119 | 0.003 |
| 34 | 0.003 |
| 117 | 0.007 |
| 122 | 0.007 |
| 82 | 0.007 |
| 113 | 0.007 |
| 20 | 0.007 |
| 27 | 0.007 |
| 104 | 0.043 |
| 102 | 0.044 |
| 72 | 0.056 |
| 105 | 0.089 |
| 58 | 0.095 |
| 103 | 0.108 |

E. Insulin Receptor Tyrosine Kinase Assay

The assays were performed in U-bottom 384-well plates. The final assay volume was 30 μl prepared from 15 μl additions of enzyme and substrates (fluoresceinated InsR substrate peptide and ATP) and test compounds in assay buffer (100 mM HEPES pH 7.4, 10 mM $MnCl_2$, 0.015% Brij35 and 4 mM DTT). The reaction was initiated by the combination of Insulin Receptor with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 μM; FL-peptide, 1.5 μM; Insulin Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

F. JAK2

The assays were performed in U-bottom 384-well plates. The final assay volume was 30 μl prepared from 15 μl additions of enzyme and substrates (fluoresceinated peptide FL-JAK2 substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 μl of 35 mM EDTA to each sample. The reaction mixture was analyzed on the Caliper LabChip 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 μM; FL-JAK2 peptide, 1.5 μM; His-CDKS/p25, 2.6 nM; and DMSO, 1.6%.

G. LCK Kinase Assay

The assays were performed in U-bottom 384-well plates. The final assay volume was 30 μl prepared from 15 μl additions of enzyme and substrates (fluoresceinated LCK substrate peptide and ATP) and test compounds in assay buffer (100 mM HEPES pH 7.4, 10 mM $MnCl_2$, 0.015% Brij35 and 4 mM DTT). The reaction was initiated by the combination of LCK with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays is ATP, 3 μM; FL-peptide, 1.5 μM; Lck, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

H. MapKapK2

The assays were performed in U-bottom 384-well plates. The final assay volume was 30 μl prepared from 15 μl additions of enzyme and substrates (fluoresceinated MK2 substrate peptide and ATP) and test compounds in assay buffer (100 mM HEPES pH 7.4, 10 mM $MgCl_2$, 0.015% Brij35 and 4 mM DTT). The reaction was initiated by the combination of MapKapK2 with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays are ATP, 1 μM; FL-peptide, 1.5 μM; MapKapK2, 0.08 nM; Brij35, 0.015% and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

I. Met Kinase Assay

Kinase reactions consisted of 0.75 ng of baculovirus expressed GST-Met, 3 ug poly(Glu/Tyr) (Sigma), 0.12 μCi 33P γ-ATP, 1 μM ATP in 30 μl kinase buffer (20 mm TRIS-Cl, 5 mM $MnCl_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 μl prepared from 15 μl additions of enzyme and substrates (fluoresceinated P38a substrate peptide and ATP) and test compounds in assay buffer (100 mM HEPES pH 7.2, 10 mM $MgCl_2$, 0.015% Brij35 and 4 mM DTT). The reaction was initiated by the combination of activated p38alpha with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase A with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM, Protein kinase A 1 nM, and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

M. Protein Kinase C-alpha

The assays were performed in U-bottom 384-well plates. The final assay volume was 30 µl prepared from 15 µl additions of enzyme and substrates (fluoresceinated PKCa substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 µM; FL-peptide, 1.5 µM; Protein kinase C-alpha, 1 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

N. TrkA Kinase Assay

Kinase reactions consisted of 0.12 ng of baculovirus expressed His-TrkA, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 ug poly(Glu/Tyr) (Sigma), 0.24 µCi 33P γ-ATP, 30 µM ATP in 30 µl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

P. IGF-1R Sal Tumor Model

A salivary gland adenocarcinoma that developed spontaneously in a transgenic mouse (MCI-19) was excised and cut into fragments of about 20 mg. Tumor fragments were implanted s.c. into the ventral thoracic region of a group of six female, athymic BALB/c nu/nu mice (Harley Sprague-Dawley, Indianapolis, Ind.), using a 13-gauge trocar. Once established, the salivary gland-derived tumor line was designated IGF1R-Sal and was propagated as a tumor xenograft in nude mice. Tumors were passaged every 2 weeks, at which time the tumor reached f500 to 1,000 mm3 in size. For treatment studies, nude micebearing IGF1R-Sal tumors of about 100 mm3 in size were sorted into groups of five for treatment with vehicle (80% polyethylene glycol 400 in water) alone or the test article. Compounds were administered either on a bid schedule (oral doses 8 hours apart) or on a once a day schedule orally (qd) for 4 consecutive days. Tumors were measured at the start and end of treatment. Activity was measured as % tumor growth inhibition (% TGI). The % TGI was determined using the following formula $(C_t - T_t)/(C_t - C_o)$ where $C_t$ is defined as the median tumor size of the control group at the end of treatment, $C_o$ is defined as the median tumor size of the control group at the start of treatment, and $T_t$ is defined as the median tumor size of the treated group at the end of treatment.

Compounds described herein were tested in the above assay. The following results were obtained.

TABLE II

| In Vivo Efficacy in IGF-1R Sal Tumor Model (qd × 4 days) | | | |
|---|---|---|---|
| Example No. | % TGI (3.13 mpk) | % TGI (6.25 mpk) | % TGI (50 mpk) |
| 18 | 96 | | |
| 65 | 80 | | |
| 85 | | 49 | |
| 68 | | 7 | |
| 83 | | | 27 |
| 84 | | | 25 |

Methods of Preparation

In general, the compounds of Formula (I) can be prepared in accordance with the following Schemes and the general knowledge of one skilled in the art. Tautomers and solvates (e.g., hydrates) of the compounds of Formula (I) are also within the scope of the invention. Methods of solvation are generally known in the art. Accordingly, the compounds of the instant invention can be in the free or hydrate form, and can be obtained by methods exemplified in the following Schemes.

Step 1

Compound IV is produced by treating compound II with an appropriately substituted amino compound III in the presence of a base, such as for example, diisoproylethylamine in a solvent, such as THF.

Step 2

Compound VI is obtained by treating compound IV with an appropriately functionalized proline V in the presence of a base, such as, for example, diisoproylethylamine in an organic solvent such as THF or methanol at room temperature. Alternatively, transition metal catalyzed methods for introduction of amino compound V may also be used.

Step 3

Compound I can be obtained by treating VI with an appropriate amine VII in the presence of a base, such as, for example, diisoproylethylamine in an organic solvent such as, THF or methanol. Alternatively, transition metal catalyzed methods for introduction of amino compound VII may also be used.

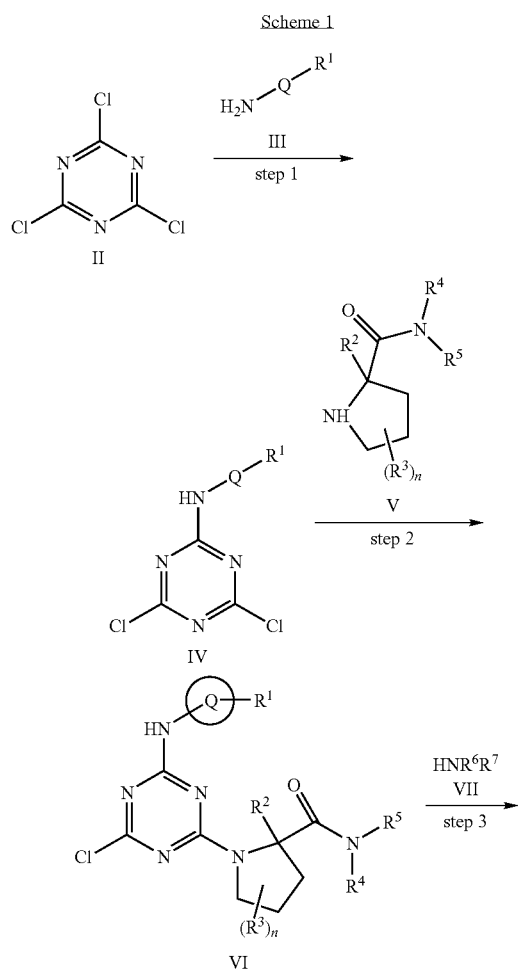

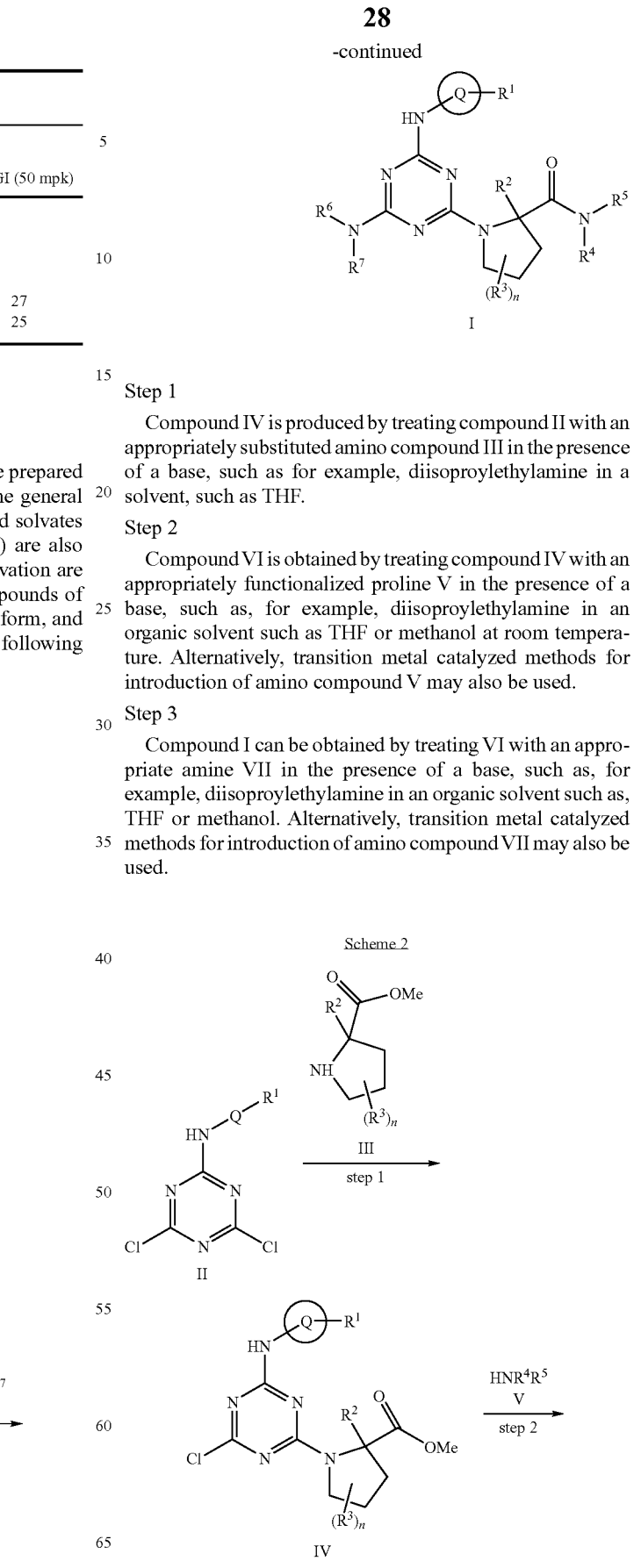

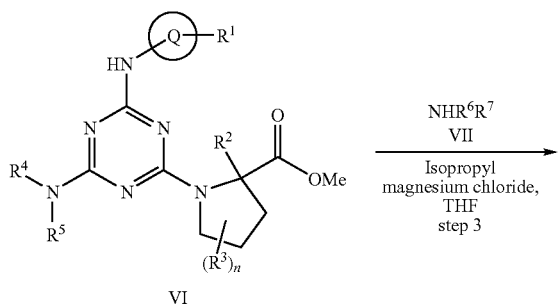

Step 1
Compound IV is obtained by treating compound II with an appropriately functionalized proline III in the presence of a base, such as, for example, diisoproylethylamine in an organic solvent such as, THF or methanol at room temperature. Alternatively, transition metal catalyzed methods for introduction of amino compound V may also be used.

Step 2
Compound VI can be obtained by treating IV with an appropriate amine V in the presence of a base, such as, for example, diisoproylethylamine in an organic solvent such as, THF or methanol. Alternatively, transition metal catalyzed methods for introduction of amino compound V may also be used.

Step 3
Compound I can be obtained by treating VI with alkali metal salts of an aryl or heteroaryl amine VII, which can be generated with alkyl metals such as, for example, methyl or isopropyl magnesium chloride. Alternatively, Compound I can be obtained by coupling of the corresponding acid of VI with an amine VII using reagents that form amide bonds such as, for example, (benzotriazol-1-yloxy)tripyrrolidinophosphonium hexafluorophosphate and a base, such as, for example, diisoproylethyl amine in a solvent such as, for example, dimethylformamide.

HPLC Conditions for Examples:
Analytical Reverse Phase HPLC retention times obtained using following methods while conducting UV detection at 220 nm:

a: Phenomenex-Luna 4.6×50 mm S10, 2 min. gradient, 4 mL/min. Solvent A (10% MeOH-90% $H_2O$-0.1% TFA); Solvent B (90% MeOH-10% $H_2O$-0.1% TFA)

b: Phenomenex-Luna 4.6×150 mm, 20 min. gradient, 1.5 mL/min. Solvent A (10% MeOH-90% $H_2O$-0.1% TFA); Solvent B (90% MeOH-10% $H_2O$-0.1% TFA)

c: Phenomenex-Luna 4.6×50 mm S10, 3 min. gradient, 4 mL/min. Solvent A (10% MeOH-90% $H_2O$-0.1% TFA); Solvent B (90% MeOH-10% $H_2O$-0.1% TFA)

d: Phenomenex-Luna 4.6×150 mm, 15 min. gradient, 1.5 mL/min. Solvent A (10% MeOH-90% $H_2O$-0.1% TFA); Solvent B (90% MeOH-10% $H_2O$-0.1% TFA)

e: Phenomenex-Luna 4.6×150 mm, 18 min. gradient, 1.5 mL/min. Solvent A (10% MeOH-90% $H_2O$-0.1% TFA); Solvent B (90% MeOH-10% $H_2O$-0.1% TFA)

f: Phenomenex-Luna 4.6×50 mm S10, 4 min. gradient, 4 mL/min. Solvent A (10% MeOH-90% $H_2O$-0.1% TFA); Solvent B (90% MeOH-10% $H_2O$-0.1% TFA)

g: Waters Xbridge phenyl 4.6X150, 25 min. gradient, 1 mL/min. Solvent A (5% Acetonitrile-95% $H_2O$-0.1% TFA); Solvent B (95% Acetonitrile-5% $H_2O$-0.1% TFA); Start % B 10 and Final % B 50.

h: Sunfire C18 4.6×150, 30 min. gradient, 1 mL/min. Solvent A (5% Acetonitrile-95% $H_2O$-0.1% TFA); Solvent B (95% Acetonitrile-5% $H_2O$-0.1% TFA); Start % B 0 and Final % B 100.

Preparative Reverse Phase (RP) HPLC was performed with a linear gradient elution using $H_2O$/MeOH mixtures buffered with 0.1% trifluoroacetic acid and detection at 220 nm or 254 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min)

All final products were characterized by $^1$H NMR, electrospray ionization (ESI MS) or atmospheric pressure ionization (API MS) mass spectrometry. $^1$H NMR spectra were obtained on a 500, 400 or 300 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

Example 1

(S)-1-(4-(3-Cyclopropyl-1H-pyrazol-5-ylamino)-6-morpholino-1,3,5-triazin-2-yl)-N-(6-fluoropyridin-3-yl)-2-methylpyrrolidine-2-carboxamide

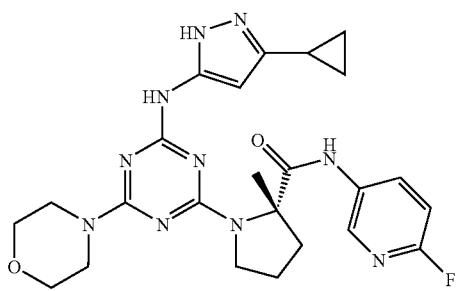 [SMILES: C[C@@]1(C(=O)Nc2ccc(F)nc2)CCCN1c1nc(Nc2cc(C3CC3)n[nH]2)nc(N2CCOCC2)n1]

1A. 4,6-Dichloro-N-(3-cyclopropyl-1H-pyrazol-5-yl)-1,3,5-triazin-2-amine

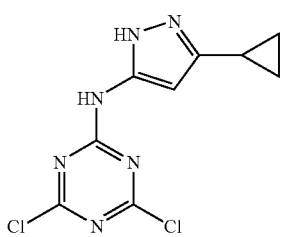 [SMILES: Clc1nc(Cl)nc(Nc2cc(C3CC3)n[nH]2)n1]

To a solution of cyanuric chloride (5 g, 27.1 mmol) in THF (40 mL) were added diisopropylethylamine (7.1 mL, 40.6 mmol) and 3-cyclopropyl-1H-pyrazol-5-amine (4.0 g, 32.5 mmol) in isopropyl alcohol (40 mL) at 0° C. over 30 minutes. The reaction mixture was stirred at room temperature overnight. The crude reaction solution was used for the next step without purification. A small amount was purified by Biotage (0-50% EtOAc/Hexane, 1 L). $^1$H NMR (DMSO, 400 MHz) δ 11.33 (s, NH), 6.19 (s, 1H), 3.83 (br s, NH), 1.88-1.95 (m, 1H), 0.93-0.96 (m, 2H), 0.68-0.70 (m, 2H). LC/MS [M+H]$^+$: 271/273; Ret time (Method F): 3.00 min.

1B. (S)—N-(6-Fluoropyridin-3-yl)-2-methylpyrrolidine-2-carboxamide

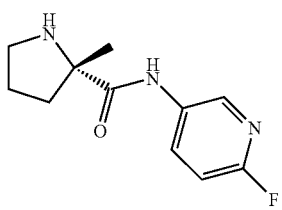 [SMILES: C[C@@]1(C(=O)Nc2ccc(F)nc2)CCCN1]

To a stirred solution of (5)-1-(tert-butoxycarbonyl)-2-methylpyrrolidine-2-carboxylic acid (1.0 g, 4.37 mmol) and 6-fluoropyridin-3-amine (1.47 g, 13.1 mmol), 1-hydroxybenzotriazole (0.65 mg, 4.81 mmol), and N-(3-dimethylaminopropyl)-N'-ethyl-carbodiimide (2.5 g, 13.1 mmol) in N-methylpyrrolidinone (10 mL) was added diisopropylethylamine (3.8 mL, 21.8 mmol). The reaction mixture was heated to 65° C. for 12 h and the solvent was evaporated to dryness. The residue was separated by preparative HPLC. The crude product was dissolved in methanol and 4N HCl in dioxane (4 mL) was added. The reaction mixture was stirred at room temperature overnight and the crude product was used in the next step without further purification. LC/MS [M+H]$^+$: 224; Ret time (Method F): 0.78 min.

1C. (S)-1-(4-Chloro-6-(3-cyclopropyl-1H-pyrazol-5-ylamino)-1,3,5-triazin-2-yl)-N-(6-fluoropyridin-3-yl)-2-methylpyrrolidine-2-carboxamide

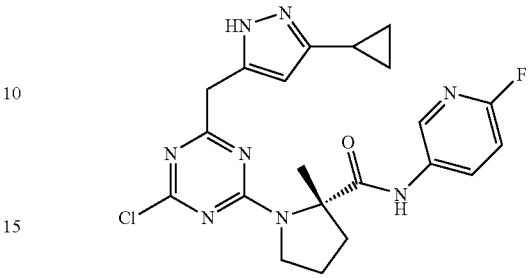

Diisopropylethylamine (0.77 mL, 4.42 mmol) was added to a mixture of 4,6-dichloro-N-(3-cyclopropyl-1H-pyrazol-5-yl)-1,3,5-triazin-2-amine (800 mg, 2.95 mmol) and (S)—N-(6-fluoropyridin-3-yl)-2-methylpyrrolidine-2-carboxamide (625 mg, 2.8 mmol) in THF (20 mL). The reaction mixture was stirred at room temperature overnight and the product was separated by preparative HPLC. Removal of the solvents furnished 1C (860 mg, 64%) as a TFA salt. LC/MS [M+H]$^+$: 458; Ret time (Method F): 2.70 min.

To a stirred solution of 1C (50 mg, 0.109 mmol) in THF (5 mL) was added morpholine (0.2 mL, excess). The reaction mixture was stirred at room temperature for 2 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 1 (37.2 mg, 67%). LC/MS [M+H]$^+$: 508; Ret time (Method A): 1.53 min.

Example 2

(S)-1-(4-(3-Cyclopropyl-1H-pyrazol-5-ylamino)-6-(4-methylpiperazin-1-yl)-1,3,5-triazin-2-yl)-N-(6-fluoropyridin-3-yl)-2-methylpyrrolidine-2-carboxamide

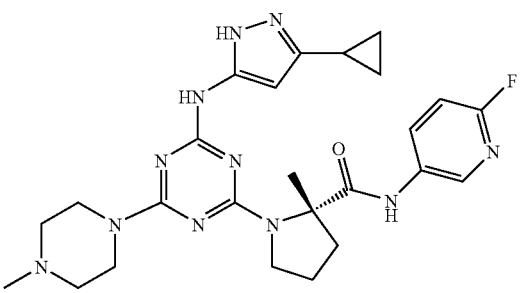 [SMILES: CN1CCN(c2nc(Nc3cc(C4CC4)n[nH]3)nc(N3CCC[C@@]3(C)C(=O)Nc3ccc(F)nc3)n2)CC1]

To a stirred solution of 1C (50 mg, 0.109 mmol) in THF (5 mL) was added N-methyl piperazine (0.2 mL, excess). The reaction mixture was stirred at room temperature for 2 hours and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 2 (36.4 mg, 64%). LC/MS [M+H]$^+$: 522; Ret time (Method F): 2.01 min.

Example 3

(S)-1-(4-(3-Cyclopropyl-1H-pyrazol-5-ylamino)-1,3,5-triazin-2-yl)-N-(6-fluoropyridin-3-yl)-2-methylpyrrolidine-2-carboxamide

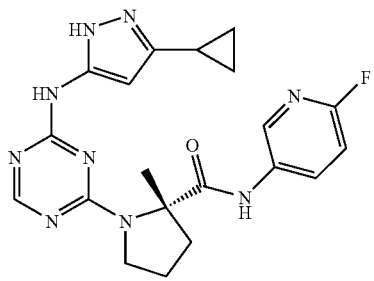 [SMILES: C[C@@]1(C(=O)Nc2ccc(F)nc2)CCCN1c1ncnc(Nc2cc(C3CC3)n[nH]2)n1]

To a stirred suspension of palladium on carbon (10%) (30 mg) in methanol (10 mL) was added (5)-1-(4-chloro-6-(3-cyclopropyl-1H-pyrazol-5-ylamino)-1,3,5-triazin-2-yl)-N-(6-fluoropyridin-3-yl)-2-methylpyrrolidine-2-carboxamide 1C (90 mg, 0.20 mmol) in methanol (10 mL). The reaction mixture was stirred under hydrogen atmosphere using hydrogen balloon at room temperature for two days. The mixture was filtered through a pad of celite, which then was washed with methanol. The filtrate was concentrated and the residue was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 4 (57 mg, 67%). LC/MS [M+H]$^+$: 424; Ret time (Method F): 2.08 min.

Example 4

(S)-1-(4-(3-Cyclopropyl-1H-pyrazol-5-ylamino)-6-(methylamino)-1,3,5-triazin-2-yl)-N-(6-fluoropyridin-3-yl)-2-methylpyrrolidine-2-carboxamide

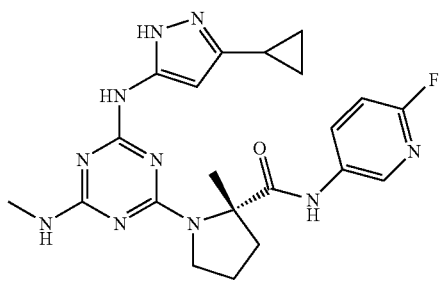 [SMILES: CNc1nc(Nc2cc(C3CC3)n[nH]2)nc(N2CCC[C@@]2(C)C(=O)Nc2ccc(F)nc2)n1]

A solution of 1C (50 mg, 0.109 mmol) and methylamine (2 M THF solution, 1 mL, excess) in ethanol (2 mL) was heated to 70° C. for 10 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 4 (21.7 mg, 44%). LC/MS [M+H]$^+$: 453; Ret time (Method F): 2.35 min.

Example 5

(S)-1-(4-(5-Cyclopropyl-1H-pyrazol-3-ylamino)-6-methoxy-1,3,5-triazin-2-yl)-N-(6-fluoropyridin-3-yl)-2-methylpyrrolidine-2-carboxamide

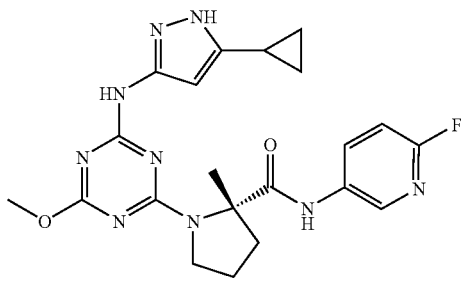 [SMILES: COc1nc(Nc2cc(C3CC3)[nH]n2)nc(N2CCC[C@@]2(C)C(=O)Nc2ccc(F)nc2)n1]

Sodium hydride (300 mg, 12.5 mmol) was added to MeOH (5 ml) at 0° C. under nitrogen. The resulting mixture was stirred at RT for 30 min. 2 ml of the reaction mixture was taken and added to a solution of 1C (100 mg, 0.219 mmol) in MeOH (3 ml). The reaction mixture was stirred at RT for 3 h and concentrated. The residue was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 5 (46 mg, 46%). LC/MS [M+H]$^+$: 454; Ret time (Method F): 2.51 min.

Examples 6 and 7

Examples 6 and 7 are disclosed in Table 1 and were prepared using procedures described above in Example 1.

TABLE 1

| Example No. | Compound | LC Ret. t. (min.) | [M + H]+ |
|---|---|---|---|
| 6 | 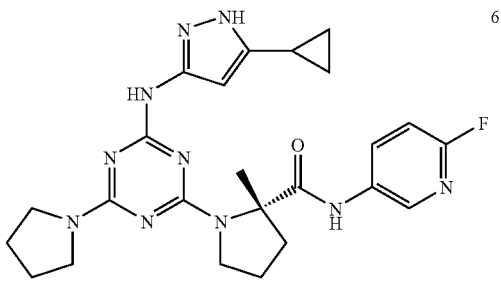<br>(S)-1-(4-(5-cyclopropyl-1H-pyrazol-3-ylamino)-6-(pyrrolidin-1-yl)-1,3,5-triazin-2-yl)-N-(6-fluoropyridin-3-yl)-2-methylpyrrolidine-2-carboxamide | 65879-124 | 493 |
| 7 | 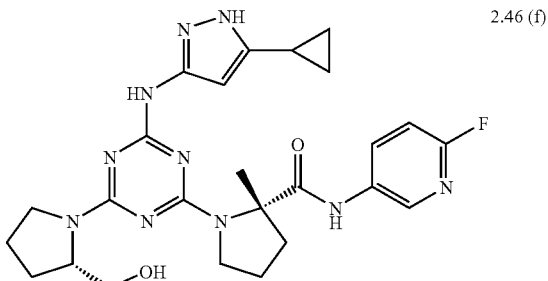<br>(S)-1-(4-(5-cyclopropyl-1H-pyrazol-3-ylamino)-6-((S)-2-(hydroxymethyl)pyrrolidin-1-yl)-1,3,5-triazin-2-yl)-N-(6-fluoropyridin-3-yl)-2-methylpyrrolidine-2-carboxamide | 2.46 (f) | 523 |

Example 8

(S)-1-(4-(3-Cyclopropyl-1H-pyrazol-5-ylamino)-6-morpholino-1,3,5-triazin-2-yl)-2-methyl-N-(pyrazin-2-yl)pyrrolidine-2-carboxamide

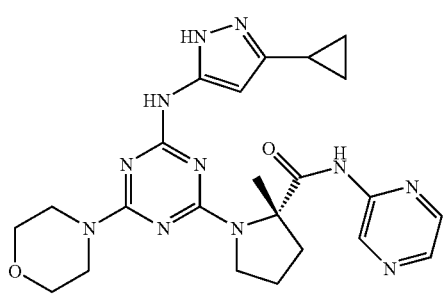 [SMILES: C[C@@]1(C(=O)Nc2cnccn2)CCCN1c1nc(Nc2cc(C3CC3)n[nH]2)nc(N2CCOCC2)n1]

8A. (S)-2-Methyl-N-(pyrazin-2-yl)pyrrolidine-2-carboxamide

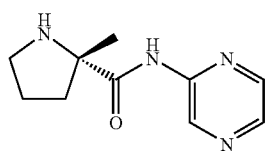

To a stirred solution of pyrazin-2-amine (1.56 g, 16.44 mmol) in THF (30 ml) was added isopropyl magnesium chloride (7.8 ml, 15.62 mmol) (2.0 M THF solution) dropwise at 0° C. under nitrogen. The resulting suspension was stirred at RT for 30 min. A solution of (S)-1-tert-butyl 2-methyl 2-methylpyrrolidine-1,2-dicarboxylate (1.0 g, 4.11 mmol) solid was added to the reaction mixture. The reaction mixture was stirred at RT for 6 h, quenched with MeOH, and concentrated. The residue was dissolved in EtOAc (120 ml) and washed with 1N HCl to remove the excess pyrazin-2-amine, water, and brine, dried over $Na_2SO_4$. The crude product was dissolved in methanol and 4N HCl in dioxane (4 mL) was added.

The reaction mixture was stirred at room temperature overnight and the crude product was used in the next step without further purification.

8B. (S)-1-(4-Chloro-6-(3-cyclopropyl-1H-pyrazol-5-ylamino)-1,3,5-triazin-2-yl)-2-methyl-N-(pyrazin-2-yl)pyrrolidine-2-carboxamide

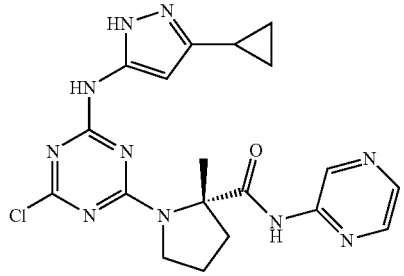 [SMILES: C[C@@]1(C(=O)Nc2cnccn2)CCCN1c1nc(Cl)nc(Nc2cc(C3CC3)n[nH]2)n1]

Diisopropylethylamine (0.77 mL, 4.42 mmol) was added to a mixture of 4,6-dichloro-N-(3-cyclopropyl-1H-pyrazol-5-yl)-1,3,5-triazin-2-amine (800 mg, 2.95 mmol) and (S)—N-(6-fluoropyridin-3-yl)-2-methylpyrrolidine-2-carboxamide (625 mg, 2.8 mmol) in THF (20 mL). The reaction mixture was stirred at room temperature overnight and the product was separated by preparative HPLC. Removal of the solvents furnished 8B (860 mg, 64%) as a TFA salt. LC/MS [M+H]$^+$: 440; Ret time (Method C): 2.33 min.

To a stirred solution of 8B (50 mg, 0.114 mmol) in THF (5 mL) was added morpholine (0.2 mL, excess). The reaction mixture was stirred at room temperature for 2 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 8 (36 mg, 64%). LC/MS [M+H]$^+$: 492; Ret time (Method F): 2.41 min.

Example 9

(S)-1-(4-(5-Cyclopropyl-1H-pyrazol-3-ylamino)-6-(piperazin-1-yl)-1,3,5-triazin-2-yl)-2-methyl-N-(pyrazin-2-yl)pyrrolidine-2-carboxamide

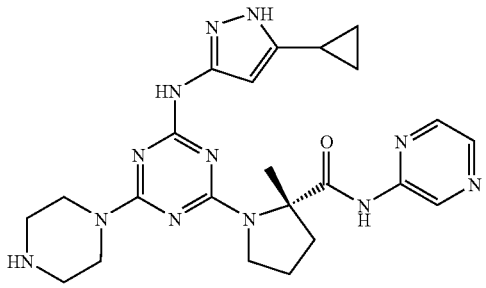 [SMILES: C[C@@]1(C(=O)Nc2cnccn2)CCCN1c1nc(Nc2cc(C3CC3)[nH]n2)nc(N2CCNCC2)n1]

To a stirred solution of 8B (50 mg, 0.114 mmol) in THF (5 mL) was added piperazine (0.2 mL, excess). The reaction mixture was stirred at room temperature for 2 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 9 (34 mg, 61%). LC/MS [M+H]$^+$: 491; Ret time (Method A): 1.32 min.

Example 10

(S)-1-(4-(4-Acetylpiperazin-1-yl)-6-(5-cyclopropyl-1H-pyrazol-3-ylamino)-1,3,5-triazin-2-yl)-2-methyl-N-(pyrazin-2-yl)pyrrolidine-2-carboxamide

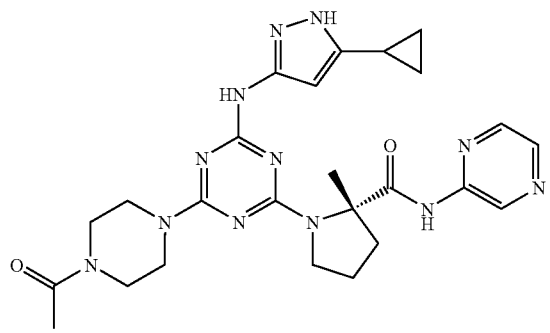 [SMILES: CC(=O)N1CCN(c2nc(Nc3cc(C4CC4)[nH]n3)nc(N3CCC[C@@]3(C)C(=O)Nc3cnccn3)n2)CC1]

To a stirred solution of 8B (50 mg, 0.114 mmol) in THF (5 mL) was added 1-(piperazin-1-yl)ethanone (0.2 mL, excess). The reaction mixture was stirred at room temperature for 2 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 10 (41 mg, 68%). LC/MS [M+H]$^+$: 533; Ret time (Method A): 1.51 min.

Examples 11 to 17

Examples 11 to 17 are disclosed in Table 2 and were prepared using procedures described above in Examples 1 and 2.

TABLE 2

| Example No. | Compound | LC Ret. t. (min.) | [M + H]+ |
|---|---|---|---|
| 11 | 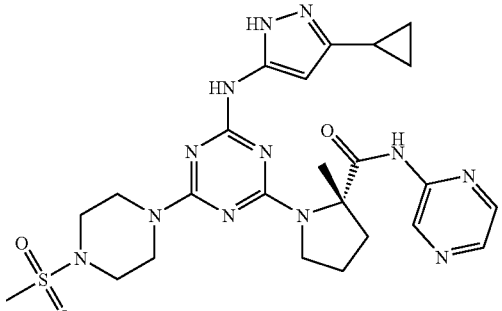(S)-1-(4-(3-Cyclopropyl-1H-pyrazol-5-ylamino)-6-(4-(methylsulfonyl)piperazin-1-yl)-1,3,5-triazin-2-yl)-2-methyl-N-(pyrazin-2-yl)pyrrolidine-2-carboxamide | 1.54 (a) | 569 |
| 12 | 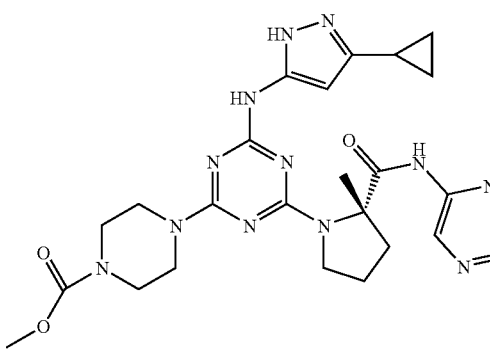(S)-Methyl 4-(4-(3-cyclopropyl-1H-pyrazol-5-ylamino)-6-(2-methyl-2-(pyrazin-2-ylcarbamoyl)pyrrolidin-1-yl)-1,3,5-triazin-2-yl)piperazine-1-carboxylate | 1.64 (a) 14.74 (b) | 549 |
| 13 | 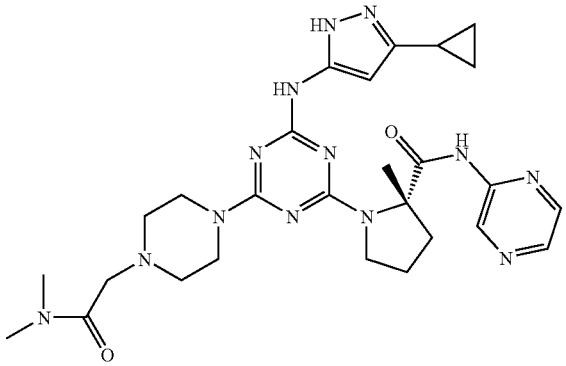 [SMILES: CN(C)C(=O)CN1CCN(c2nc(Nc3cc(C4CC4)n[nH]3)nc(N3CCC[C@@]3(C)C(=O)Nc3cnccn3)n2)CC1](S)-1-(4-(3-Cyclopropyl-1H-pyrazol-5-ylamino)-6-(4-(2-(dimethylamino)-2-oxoethyl)piperazin-1-yl)-1,3,5-triazin-2-yl)-2-methyl-N-(pyrazin-2-yl)pyrrolidine-2-carboxamide | 1.32 (a) | 576 |

TABLE 2-continued

| Example No. | Compound | LC Ret. t. (min.) | [M + H]+ |
|---|---|---|---|
| 14 | 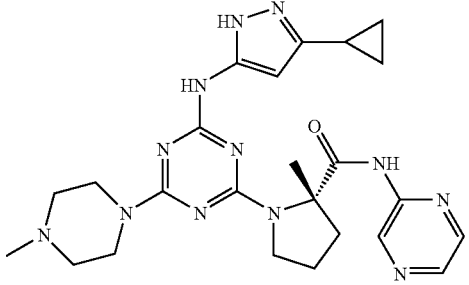 [SMILES: CN1CCN(c2nc(Nc3cc(C4CC4)n[nH]3)nc(N3CCC[C@@]3(C)C(=O)Nc3cnccn3)n2)CC1]<br>(S)-1-(4-(3-Cyclopropyl-1H-pyrazol-5-ylamino)-6-(4-methylpiperazin-1-yl)-1,3,5-triazin-2-yl)-2-methyl-N-(pyrazin-2-yl)pyrrolidine-2-carboxamide | 1.95 (c)<br>10.57 (d) | 505 |
| 15 | 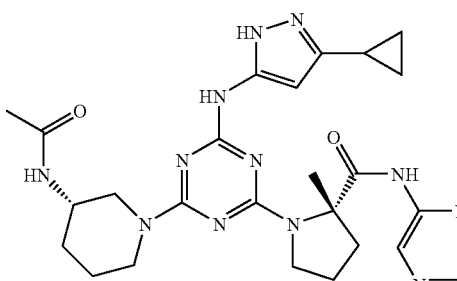<br>(S)-1-(4-((S)-3-Acetamidopiperidin-1-yl)-6-(3-cyclopropyl-1H-pyrazol-5-ylamino)-1,3,5-triazin-2-yl)-2-methyl-N-(pyrazin-2-yl)pyrrolidine-2-carboxamide | 2.27 (c)<br>13.78 (b) | 547 |
| 16 | 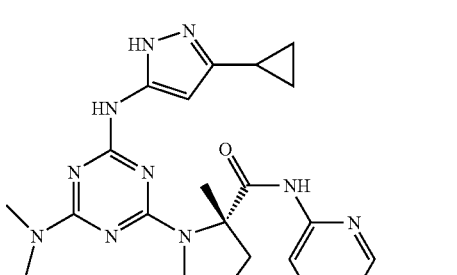<br>(S)-1-(4-(3-Cyclopropyl-1H-pyrazol-5-ylamino)-6-(dimethylamino)-1,3,5-triazin-2-yl)-2-methyl-N-(pyrazin-2-yl)pyrrolidine-2-carboxamide | 1.51 (a)<br>12.35 (d) | 450 |
| 17 | 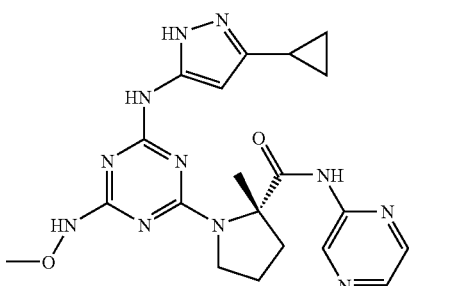<br>(S)-1-(4-(3-Cyclopropyl-1H-pyrazol-5-ylamino)-6-(methoxyamino)-1,3,5-triazin-2-yl)-2-methyl-N-(pyrazin-2-yl)pyrrolidine-2-carboxamide | 2.01 (c) | 452 |

Example 18

(2S,4S)-1-(4-(3-Cyclopropyl-1H-pyrazol-5-ylamino)-6-morpholino-1,3,5-triazin-2-yl)-4-methoxy-N-(pyrazin-2-yl)pyrrolidine-2-carboxamide

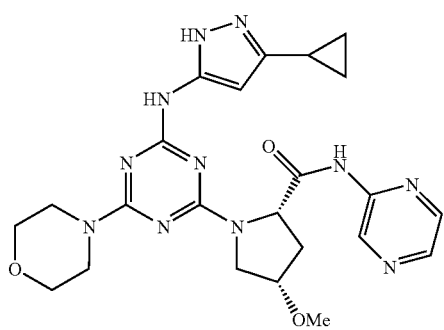 [SMILES: CO[C@H]1C[C@@H](C(=O)Nc2cnccn2)N(c2nc(Nc3cc(C4CC4)n[nH]3)nc(N3CCOCC3)n2)C1]

18A. (2S,4S)-1-(Benzyloxycarbonyl)-4-methoxypyrrolidine-2-carboxylic acid

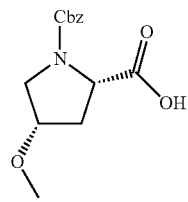 [SMILES: CO[C@H]1C[C@@H](C(=O)O)N(C(=O)OCc2ccccc2)C1]

18A was prepared from commercially available (2S,4S)-1-(benzyloxycarbonyl)-4-hydroxypyrrolidine-2-carboxylic acid according to the procedures described in *J. Med. Chem.*, 331:875-885 (1988).

18B. (2S,4S)-1-Benzyl 2-methyl 4-methoxypyrrolidine-1,2-dicarboxylate

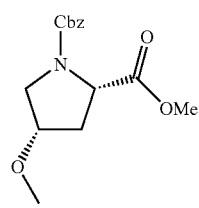 [SMILES: COC(=O)[C@@H]1C[C@H](OC)CN1C(=O)OCc1ccccc1]

To a solution of (2S,4S)-1-(benzyloxycarbonyl)-4-methoxypyrrolidine-2-carboxylic acid (3.0 g, 0.01 mol) in methanol (40 mL0 and diethyl ether (20 mL) was added (trimethylsilyl)diazomethane (2.0 M solution in diethyl ether, 6.4 mL, 0.013 mol) dropwise under ice-bath. The reaction mixture was stirred at room temperature for 1 h. Concentration of the reaction mixture gave (2S,4S)-1-benzyl 2-methyl 4-methoxypyrrolidine-1,2-dicarboxylate 18B (3.2 g, 100%) as an oil which was used in the next step without purification. $^1$H NMR (CDCl$_3$, 400 MHz) δ 7.27-7.36 (m, 5H), 5.04-5.19 (m, 2H), 4.39-4.50 (m, 1H), 3.91-3.94 (m, 1H), 3.53-3.72 (m, 5H), 3.24 (s, 3H), 2.21-2.35 (m, 2H).

18C. (2S,4S)-Benzyl 4-methoxy-2-(pyrazin-2-ylcarbamoyl)pyrrolidine-1-carboxylate

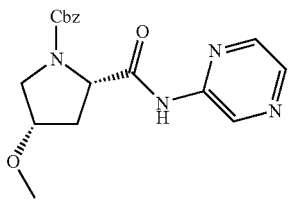 [SMILES: CO[C@H]1C[C@@H](C(=O)Nc2cnccn2)N(C(=O)OCc2ccccc2)C1]

To a solution of aminopyrazine (535 mg, 5.63 mmol) in THF (15 mL) was added isopropylmagnesium chloride (2.0 M THF solution, 2.7 mL, 5.35 mmol) dropwise at 0° C. The resulting slurry was stirred at room temperature for 30 min. A solution of (2S,4S)-1-benzyl 2-methyl 4-methoxypyrrolidine-1,2-dicarboxylate (550 mg, 1.88 mmol) in THF (2 mL) was added to the slurry. The reaction mixture was stirred at room temperature for 4 h and quenched with methanol (3 mL). The crude product was purified by preparative HPLC to give (2S,4S)-benzyl 4-methoxy-2-(pyrazin-2-ylcarbamoyl)pyrrolidine-1-carboxylate 18C (570 mg, 85%) as an oil. LC/MS [M+H]$^+$: 356; Ret time (Method F): 2.32 min.

18D. (2S,4S)-4-Methoxy-N-(pyrazin-2-yl)pyrrolidine-2-carboxamide

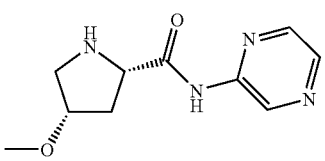 [SMILES: CO[C@@H]1CN[C@H](C(=O)Nc2cnccn2)C1]

To a solution of (2S,4S)-benzyl 4-methoxy-2-(pyrazin-2-ylcarbamoyl)pyrrolidine-1-carboxylate 18C (550 mg, 1.54 mmol) in methanol (200 mL) was added palladium on carbon (10%, 80 mg) under nitrogen. The suspension was hydrogenated at 55 psi overnight. The resulting suspension was filtered through a pad of celite and washed with methanol. Concentration of the filtrate gave the product (18D) as an oil (350 mg, 100%) which was used without purification in the next step. LC/MS [M+H]$^+$: 223; Ret time (Method F): 0.76 min.

18E. (2S,4S)-1-(4-Chloro-6-(3-cyclopropyl-1H-pyrazol-5-ylamino)-1,3,5-triazin-2-yl)-4-methoxy-N-(pyrazin-2-yl)pyrrolidine-2-carboxamide

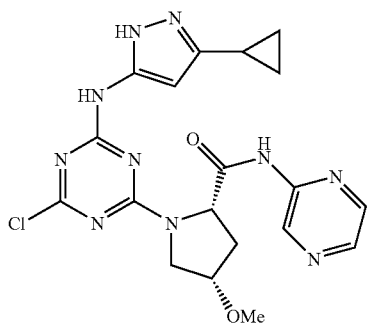 [SMILES: CO[C@H]1C[C@@H](C(=O)Nc2cnccn2)N(c2nc(Cl)nc(Nc3cc(C4CC4)n[nH]3)n2)C1]

Diisopropylethylamine (0.69 mL, 3.97 mmol) was added to a mixture of 4,6-dichloro-N-(3-cyclopropyl-1H-pyrazol-5-yl)-1,3,5-triazin-2-amine 1A (500 mg, 1.32 mmol) and (2S,4S)-4-methoxy-N-(pyrazin-2-yl)pyrrolidine-2-carboxamide (278 mg, 1.25 mmol) in isopropanol (15 mL) and THF (15 mL). The reaction mixture was stirred at room temperature overnight. The crude reaction mixture was used in the next step without concentration. LC/MS [M+H]$^+$: 457/459; Ret time (Method F): 2.40 min.

Morpholine (0.2 mL, excess) was added to a solution of crude (2S,4S)-1-(4-chloro-6-(3-cyclopropyl-1H-pyrazol-5-ylamino)-1,3,5-triazin-2-yl)-4-methoxy-N-(pyrazin-2-yl)pyrrolidine-2-carboxamide 18E (~150 mg) in methanol. The reaction mixture was stirred at room temperature for 3 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 18 (80 mg, 50%). LC/MS [M+H]$^+$: 508; Ret time (Method F): 2.40 min.

Example 19

(2S,4S)-1-(4-(3-Cyclopropyl-1H-pyrazol-5-ylamino)-6-(4-methylpiperazin-1-yl)-1,3,5-triazin-2-yl)-4-methoxy-N-(pyrazin-2-yl)pyrrolidine-2-carboxamide

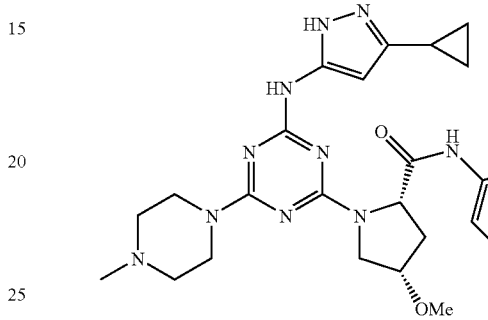

1-Methylpiperazine (0.2 mL, excess) was added to a solution of crude (2S,4S)-1-(4-chloro-6-(3-cyclopropyl-1H-pyrazol-5-ylamino)-1,3,5-triazin-2-yl)-4-methoxy-N-(pyrazin-2-yl)pyrrolidine-2-carboxamide 18E (~150 mg) in methanol. The reaction mixture was stirred at room temperature for 3 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 19 (84 mg, 49%). LC/MS [M+H]$^+$: 521; Ret time (Method F): 1.88 min.

Example 20

(2S,4S)-1-(4-(5-Cyclopropyl-1H-pyrazol-3-ylamino)-6-methoxy-1,3,5-triazin-2-yl)-4-methoxy-N-(pyrazin-2-yl)pyrrolidine-2-carboxamide

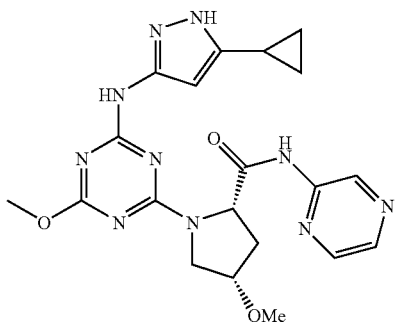 [SMILES: COc1nc(Nc2cc(C3CC3)[nH]n2)nc(N2C[C@@H](OC)C[C@H]2C(=O)Nc2cnccn2)n1]

Compound 20 was prepared from 18E using the same procedure as compound 5. LC/MS [M+H]+: 453; Ret time (Method A): 1.54 min. HPLC Ret time (Method B): 14.05 min.

Example 21

(2S,4S)-1-(4-(3-Cyclopropyl-1H-pyrazol-5-ylamino)-6-(piperazin-1-yl)-1,3,5-triazin-2-yl)-4-methoxy-N-(pyrazin-2-yl)pyrrolidine-2-carboxamide

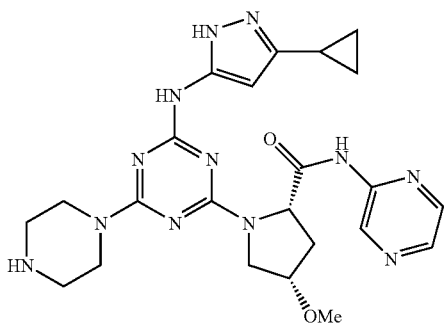 [SMILES: CO[C@H]1C[C@@H](C(=O)Nc2cnccn2)N(c2nc(Nc3cc(C4CC4)n[nH]3)nc(N3CCNCC3)n2)C1]

Piperazine (0.5 mL, excess) was added to a solution of crude (2S,4S)-1-(4-chloro-6-(3-cyclopropyl-1H-pyrazol-5-ylamino)-1,3,5-triazin-2-yl)-4-methoxy-N-(pyrazin-2-yl)pyrrolidine-2-carboxamide 18E (~500 mg, 1.13 mmol) in methanol. The reaction mixture was stirred at room temperature for 3 h and the product was separated by preparative HPLC. One fifth of the TFA salt of the product was dissolved in methanol and placed on MCX cartridge. After washing with methanol, the free base of the product was released using 2M ammonia solution. Removal of the solvents furnished 21 (84 mg, 76%). LC/MS [M+H]+: 507; Ret time (Method F): 2.26 min.

Example 22

(2S,4S)-1-(4-(4-Acetylpiperazin-1-yl)-6-(3-cyclopropyl-1H-pyrazol-5-ylamino)-1,3,5-triazin-2-yl)-4-methoxy-N-(pyrazin-2-yl)pyrrolidine-2-carboxamide

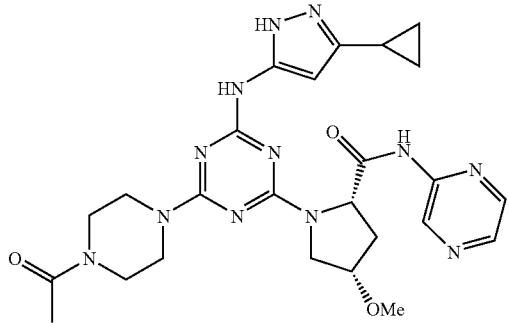 [SMILES: CO[C@H]1C[C@@H](C(=O)Nc2cnccn2)N(c2nc(Nc3cc(C4CC4)n[nH]3)nc(N3CCN(C(C)=O)CC3)n2)C1]

Triethylamine (150 mg, 1.48 mmol) was added to a solution of (2S,4S)-1-(4-(3-cyclopropyl-1H-pyrazol-5-ylamino)-6-(piperazin-1-yl)-1,3,5-triazin-2-yl)-4-methoxy-N-(pyrazin-2-yl)pyrrolidine-2-carboxamide (110 mg, 0.22 mmol) and acetyl chloride (18 mg, 0.44 mmol) in MeOH (5 ml). The reaction mixture was stirred at RT for 6 h and concentrated. The residue was separated by preparative HPLC. One fifth of the TFA salt of the product was dissolved in methanol and placed on MCX cartridge. After washing with methanol, the free base of the product was released using 2M ammonia solution. Removal of the solvents furnished 22 (64 mg, 53%). LC/MS [M+H]+: 549; Ret time (Method F): 2.79 min.

Example 23

(2S,4S)-1-(4-(3-Cyclopropyl-1H-pyrazol-5-ylamino)-6-(1H-imidazol-1-yl)-1,3,5-triazin-2-yl)-4-methoxy-N-(pyrazin-2-yl)pyrrolidine-2-carboxamide

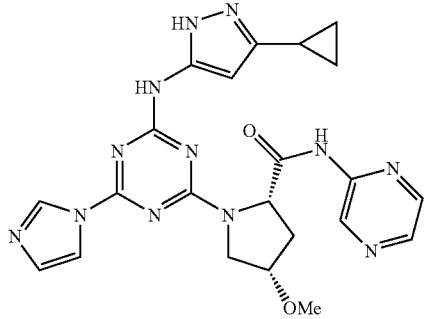 [SMILES: CO[C@H]1C[C@@H](C(=O)Nc2cnccn2)N(c2nc(Nc3cc(C4CC4)n[nH]3)nc(-n3ccnc3)n2)C1]

A solution of (2S,4S)-1-(4-chloro-6-(3-cyclopropyl-1H-pyrazol-5-ylamino)-1,3,5-triazin-2-yl)-4-methoxy-N-(pyrazin-2-yl)pyrrolidine-2-carboxamide 18E (100 mg, 0.22 mmol), imidazole (400 mg, excess), and Hunig's base (66 mg, 0.66 mmol) in EtOH (5 ml) was heated to 100° C. for 5 h and concentrated. The residue was separated by preparative HPLC. One fifth of the TFA salt of the product was dissolved in methanol and placed on MCX cartridge. After washing with methanol, the free base of the product was released using 2M ammonia solution. Removal of the solvents furnished 23 (57 mg, 53%). LC/MS [M+H]+: 489; Ret time (Method F): 2.05 min.

Examples 24 to 61

Examples 24 to 61 are disclosed in Table 3 and were prepared using procedures described above in Examples 18, 20, 22, and 23.

TABLE 3

| Example No. | Compound | HPLC ret. t. (min.) | [M + H]+ |
|---|---|---|---|
| 24 | 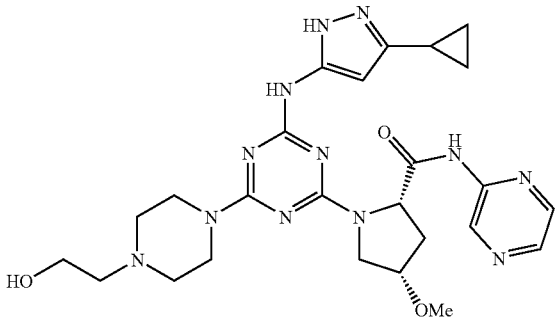 [SMILES: CO[C@H]1C[C@@H](C(=O)Nc2cnccn2)N(c2nc(Nc3cc(C4CC4)n[nH]3)nc(N3CCN(CCO)CC3)n2)C1]<br>(2S,4S)-1-(4-(3-Cyclopropyl-1H-pyrazol-5-ylamino)-6-(4-(2-hydroxyethyl)piperazin-1-yl)-1,3,5-triazin-2-yl)-4-methoxy-N-(pyrazin-2-yl)pyrrolidine-2-carboxamide | 1.86 | 551 |
| 25 | 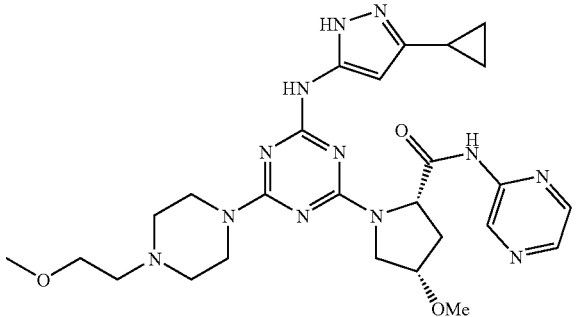 [SMILES: COCCN1CCN(c2nc(Nc3cc(C4CC4)n[nH]3)nc(N3C[C@@H](OC)C[C@H]3C(=O)Nc3cnccn3)n2)CC1]<br>(2S,4S)-1-(4-(3-Cyclopropyl-1H-pyrazol-5-ylamino)-6-(4-(2-methoxyethyl)piperazin-1-yl)-1,3,5-triazin-2-yl)-4-methoxy-N-(pyrazin-2-yl)pyrrolidine-2-carboxamide | 1.94 (f) | 565 |
| 26 | 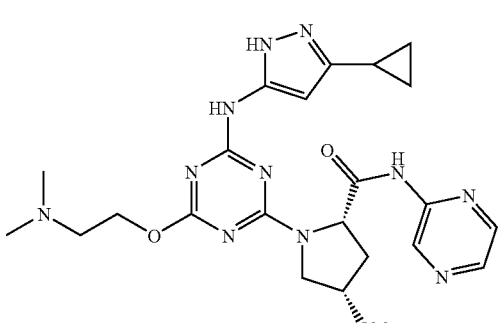<br>(2S,4S)-1-(4-(3-Cyclopropyl-1H-pyrazol-5-ylamino)-6-(2-(dimethylamino)ethoxy)-1,3,5-triazin-2-yl)-4-methoxy-N-(pyrazin-2-yl)pyrrolidine-2-carboxamide | 1.82 (f) | 510 |

TABLE 3-continued

| Example No. | Compound | HPLC ret. t. (min.) | [M + H]⁺ |
|---|---|---|---|
| 27 | 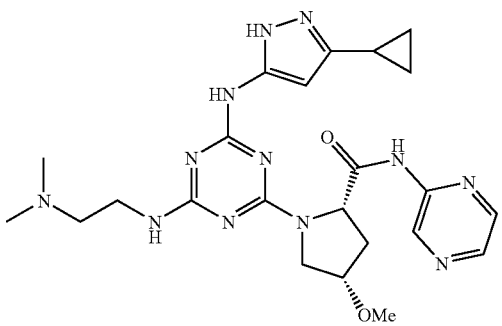 [SMILES: CO[C@H]1C[C@@H](C(=O)Nc2cnccn2)N(c2nc(NCCN(C)C)nc(Nc3cc(C4CC4)n[nH]3)n2)C1]<br>(2S,4S)-1-(4-(3-Cyclopropyl-1H-pyrazol-5-ylamino)-6-(2-(dimethylamino)ethylamino)-1,3,5-triazin-2-yl)-4-methoxy-N-(pyrazin-2-yl)pyrrolidine-2-carboxamide | 1.75 (f) | 509 |
| 28 | 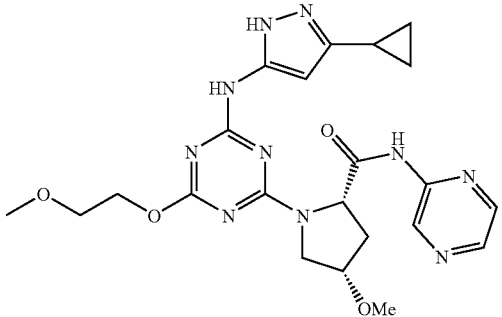 [SMILES: COCCOc1nc(Nc2cc(C3CC3)n[nH]2)nc(N2C[C@@H](OC)C[C@H]2C(=O)Nc2cnccn2)n1]<br>(2S,4S)-1-(4-(3-Cyclopropyl-1H-pyrazol-5-ylamino)-6-(2-(dimethylamino)ethylamino)-1,3,5-triazin-2-yl)-4-methoxy-N-(pyrazin-2-yl)pyrrolidine-2-carboxamide | 2.74 (f) | 497 |
| 29 | 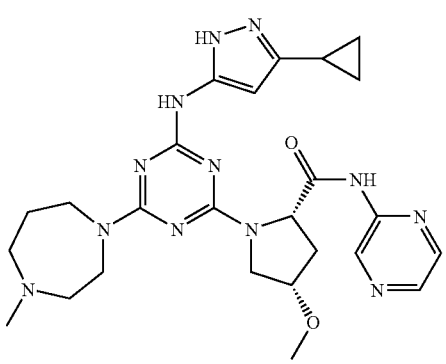 [SMILES: CO[C@H]1C[C@@H](C(=O)Nc2cnccn2)N(c2nc(Nc3cc(C4CC4)n[nH]3)nc(N3CCCN(C)CC3)n2)C1]<br>(2S,4S)-1-(4-(3-Cyclopropyl-1H-pyrazol-5-ylamino)-6-(4-methyl-1,4-diazepan-1-yl)-1,3,5-triazin-2-yl)-4-methoxy-N-(pyrazin-2-yl)pyrrolidine-2-carboxamide | 1.92 (f) | 535 |

TABLE 3-continued

| Example No. | Compound | HPLC ret. t. (min.) | [M + H]+ |
|---|---|---|---|
| 30 | 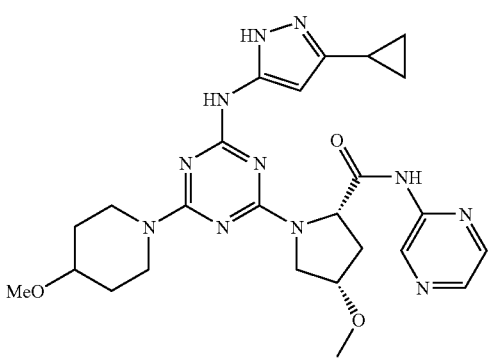 [SMILES: COC1CCN(c2nc(Nc3cc(C4CC4)n[nH]3)nc(N3C[C@@H](OC)C[C@H]3C(=O)Nc3cnccn3)n2)CC1]<br>(2S,4S)-1-(4-(3-Cyclopropyl-1H-pyrazol-5-ylamino)-6-(4-methoxypiperidin-1-yl)-1,3,5-triazin-2-yl)-4-methoxy-N-(pyrazin-2-yl)pyrrolidine-2-carboxamide | 2.41 (c)<br>14.09 (e) | 536 |
| 31 | 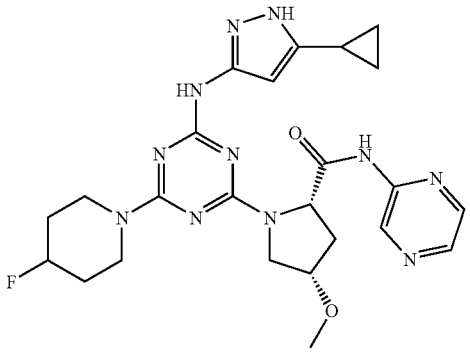 [SMILES: CO[C@H]1C[C@@H](C(=O)Nc2cnccn2)N(c2nc(Nc3cc(C4CC4)[nH]n3)nc(N3CCC(F)CC3)n2)C1]<br>(2S,4S)-1-(4-(5-Cyclopropyl-1H-pyrazol-3-ylamino)-6-(4-fluoropiperidin-1-yl)-1,3,5-triazin-2-yl)-4-methoxy-N-(pyrazin-2-yl)pyrrolidine-2-carboxamide | 1.64 (a) | 524 |
| 32 | 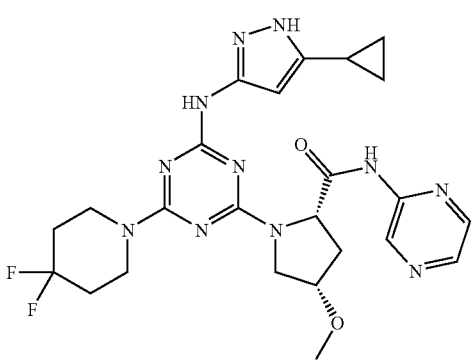 [SMILES: CO[C@H]1C[C@@H](C(=O)Nc2cnccn2)N(c2nc(Nc3cc(C4CC4)[nH]n3)nc(N3CCC(F)(F)CC3)n2)C1]<br>(2S,4S)-1-(4-(5-Cyclopropyl-1H-pyrazol-3-ylamino)-6-(4,4-difluoropiperidin-1-yl)-1,3,5-triazin-2-yl)-4-methoxy-N-(pyrazin-2-yl)pyrrolidine-2-carboxamide | 1.75 (a) | 542 |

TABLE 3-continued
| Example No. | Compound | HPLC ret. t. (min.) | [M + H]+ |
|---|---|---|---|
| 33 | 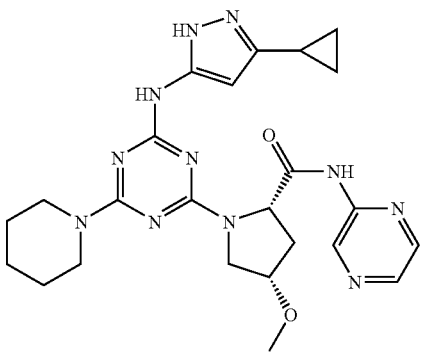 [SMILES: CO[C@H]1C[C@@H](C(=O)Nc2cnccn2)N(c2nc(Nc3cc(C4CC4)n[nH]3)nc(N3CCCCC3)n2)C1]<br>(2S,4S)-1-(4-(3-Cyclopropyl-1H-pyrazol-5-ylamino)-6-(piperidin-1-yl)-1,3,5-triazin-2-yl)-4-methoxy-N-(pyrazin-2-yl)pyrrolidine-2-carboxamide | 2.53 (c)<br>14.76 (e) | 506 |
| 34 | 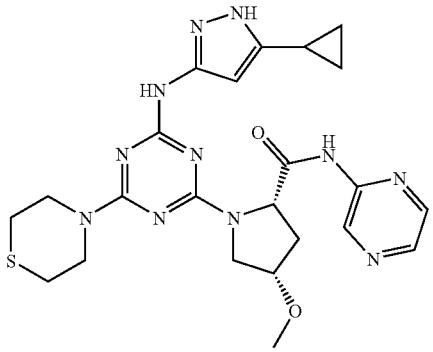 [SMILES: CO[C@H]1C[C@@H](C(=O)Nc2cnccn2)N(c2nc(Nc3cc(C4CC4)[nH]n3)nc(N3CCSCC3)n2)C1]<br>(2S,4S)-1-(4-(5-Cyclopropyl-1H-pyrazol-3-ylamino)-6-thiomorpholino-1,3,5-triazin-2-yl)-4-methoxy-N-(pyrazin-2-yl)pyrrolidine-2-carboxamide | 1.73 (a) | 524 |
| 35 | 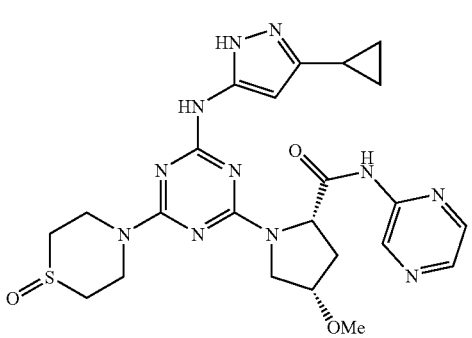 [SMILES: CO[C@H]1C[C@@H](C(=O)Nc2cnccn2)N(c2nc(Nc3cc(C4CC4)n[nH]3)nc(N3CCS(=O)CC3)n2)C1] | 2.21 (f) | 540 |
| 36 | 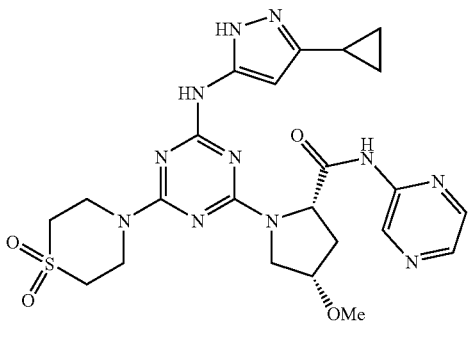 [SMILES: CO[C@H]1C[C@@H](C(=O)Nc2cnccn2)N(c2nc(Nc3cc(C4CC4)n[nH]3)nc(N3CCS(=O)(=O)CC3)n2)C1] | 2.28 (c) | 556 |

TABLE 3-continued

| Example No. | Compound | HPLC ret. t. (min.) | [M + H]+ |
|---|---|---|---|
| 37 | 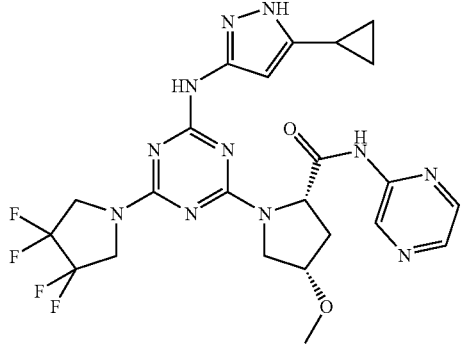 [SMILES: CO[C@H]1C[C@@H](C(=O)Nc2cnccn2)N(c2nc(Nc3cc(C4CC4)[nH]n3)nc(N3CC(F)(F)C(F)(F)C3)n2)C1]<br>(2S,4S)-1-(4-(5-Cyclopropyl-1H-pyrazol-3-ylamino)-6-(3,3,4,4-tetrafluoropyrrolidin-1-yl)-1,3,5-triazin-2-yl)-4-methoxy-N-(pyrazin-2-yl)pyrrolidine-2-carboxamide | 1.97 (a) | 564 |
| 38 | 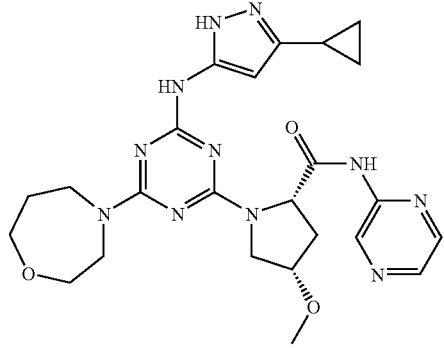 [SMILES: CO[C@H]1C[C@@H](C(=O)Nc2cnccn2)N(c2nc(Nc3cc(C4CC4)n[nH]3)nc(N3CCCOCC3)n2)C1]<br>(2S,4S)-1-(4-(3-Cyclopropyl-1H-pyrazol-5-ylamino)-6-(1,4-oxazepan-4-yl)-1,3,5-triazin-2-yl)-4-methoxy-N-(pyrazin-2-yl)pyrrolidine-2-carboxamide | 2.75 (f) | 522 |
| 39 | 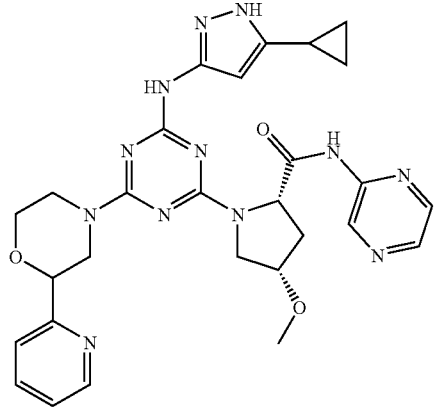 [SMILES: CO[C@H]1C[C@@H](C(=O)Nc2cnccn2)N(c2nc(Nc3cc(C4CC4)[nH]n3)nc(N3CCOC(c4ccccn4)C3)n2)C1]<br>(2S,4S)-1-(4-(5-Cyclopropyl-1H-pyrazol-3-ylamino)-6-(2-(pyridin-2-yl)morpholino)-1,3,5-triazin-2-yl)-4-methoxy-N-(pyrazin-2-yl)pyrrolidine-2-carboxamide | 2.31 (f) | 520 |

TABLE 3-continued

| Example No. | Compound | HPLC ret. t. (min.) | [M + H]+ |
|---|---|---|---|
| 40 | 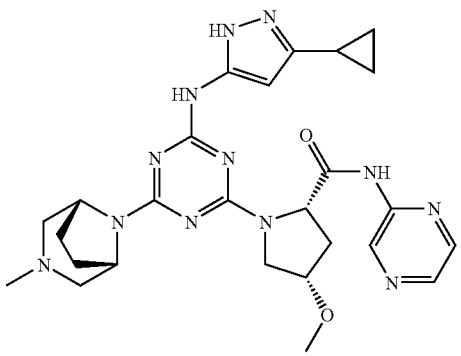 [SMILES: CO[C@H]1C[C@@H](C(=O)Nc2cnccn2)N(c2nc(Nc3cc(C4CC4)n[nH]3)nc(N3[C@@H]4CC[C@H]3CN(C)C4)n2)C1] (2S,4S)-1-(4-(3-Cyclopropyl-1H-pyrazol-5-ylamino)-6-((1R,5S)-3-methyl-3,8-diazabicyclo[3.2.1]octan-8-yl)-1,3,5-triazin-2-yl)-4-methoxy-N-(pyrazin-2-yl)pyrrolidine-2-carboxamide | 2.1 (f) 12.79 (b) | 547 |
| 41 | 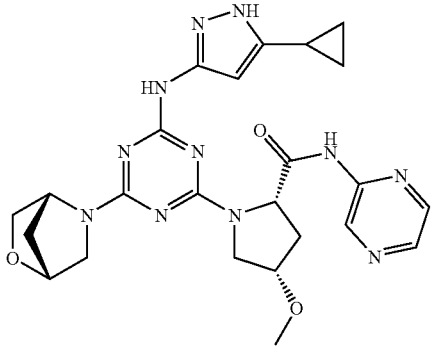 [SMILES: CO[C@H]1C[C@@H](C(=O)Nc2cnccn2)N(c2nc(Nc3cc(C4CC4)[nH]n3)nc(N3C[C@H]4C[C@@H]3CO4)n2)C1] (2S,4S)-1-(4-((1R,4R)-2-Oxa-5-azabicyclo[2.2.1]heptan-5-yl)-6-(5-cyclopropyl-1H-pyrazol-3-ylamino)-1,3,5-triazin-2-yl)-4-methoxy-N-(pyrazin-2-yl)pyrrolidine-2-carboxamide | 2.31 (f) | 520 |
| 42 | 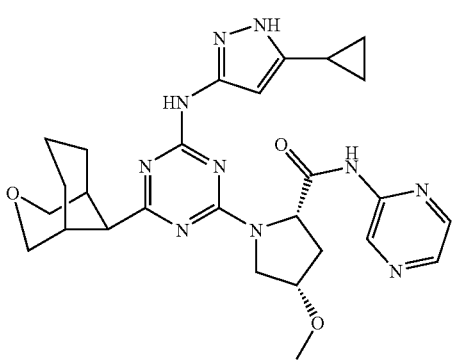 [SMILES: CO[C@H]1C[C@@H](C(=O)Nc2cnccn2)N(c2nc(Nc3cc(C4CC4)[nH]n3)nc(C3C4CCCC3COC4)n2)C1] (2S,4S)-1-(4-(3-Oxabicyclo[3.3.1]nonan-9-yl)-6-(5-cyclopropyl-1H-pyrazol-3-ylamino)-1,3,5-triazin-2-yl)-4-methoxy-N-(pyrazin-2-yl)pyrrolidine-2-carboxamide | 1.68 (a) | 548 |

TABLE 3-continued

| Example No. | Compound | HPLC ret. t. (min.) | [M + H]+ |
|---|---|---|---|
| 43 | 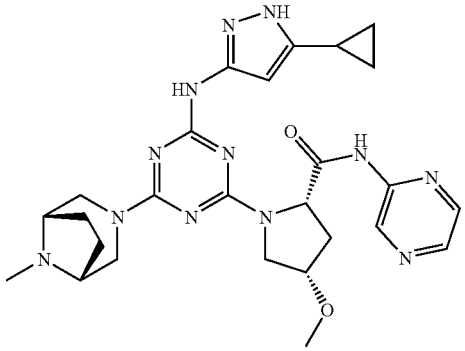 [SMILES: CO[C@H]1C[C@@H](C(=O)Nc2cnccn2)N(c2nc(Nc3cc(C4CC4)[nH]n3)nc(N3C[C@H]4CC[C@@H](C3)N4C)n2)C1]<br>(2S,4S)-1-(4-(5-Cyclopropyl-1H-pyrazol-3-ylamino)-6-((1R,5S)-8-methyl-3,8-diazabicyclo[3.2.1]octan-3-yl)-1,3,5-triazin-2-yl)-4-methoxy-N-(pyrazin-2-yl)pyrrolidine-2-carboxamide | 1.33 (a) | 547 |
| 44 | 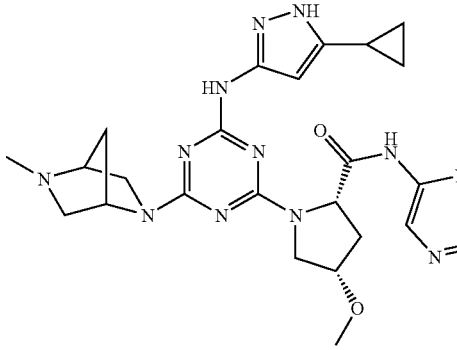<br>(2S,4S)-1-(4-(5-Cyclopropyl-1H-pyrazol-3-ylamino)-6-(5-methyl-2,5-diazabicyclo[2.2.1]heptan-2-yl)-1,3,5-triazin-2-yl)-4-methoxy-N-(pyrazin-2-yl)pyrrolidine-2-carboxamide | 1.92 (f) | 533 |
| 45 | 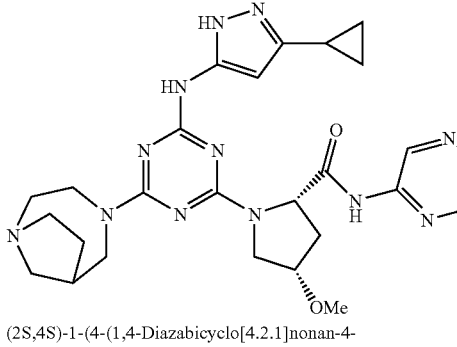<br>(2S,4S)-1-(4-(1,4-Diazabicyclo[4.2.1]nonan-4-yl)-6-(3-cyclopropyl-1H-pyrazol-5-ylamino)-1,3,5-triazin-2-yl)-4-methoxy-N-(pyrazin-2-yl)pyrrolidine-2-carboxamide | 1.95 (f) | 547 |

TABLE 3-continued

| Example No. | Compound | HPLC ret. t. (min.) | [M + H]+ |
|---|---|---|---|
| 46 | (2S,4S)-1-(4-(3-Cyclopropyl-1H-pyrazol-5-ylamino)-6-(4-(methylsulfonyl)piperazin-1-yl)-1,3,5-triazin-2-yl)-4-methoxy-N-(pyrazin-2-yl)pyrrolidine-2-carboxamide | 1.52 (a) 14.29 (b) | 585 |
| 47 | (2S,4S)-1-(4-(3-Cyclopropyl-1H-pyrazol-5-ylamino)-6-(4-(2-(methylsulfonyl)ethyl)piperazin-1-yl)-1,3,5-triazin-2-yl)-4-methoxy-N-(pyrazin-2-yl)pyrrolidine-2-carboxamide | 1.92 (f) | 613 |
| 48 | (2S,4S)-1-(4-(4-Acetylpiperazin-1-yl)-6-(3-cyclopropyl-1H-pyrazol-5-ylamino)-1,3,5-triazin-2-yl)-4-methoxy-N-(pyrazin-2-yl)pyrrolidine-2-carboxamide | 2.40 (f) | 549 |

TABLE 3-continued

| Example No. | Compound | HPLC ret. t. (min.) | [M + H]+ |
|---|---|---|---|
| 49 | Methyl 4-(4-(3-cyclopropyl-1H-pyrazol-5-ylamino)-6-((2S,4S)-4-methoxy-2-(pyrazin-2-ylcarbamoyl)pyrrolidin-1-yl)-1,3,5-triazin-2-yl)piperazine-1-carboxylate | 2.68 (f) 12.90 (g) | 565 |
| 50 | (2S,4S)-1-(4-(5-Cyclopropyl-1H-pyrazol-3-ylamino)-6-(4-cyclopropylpiperazin-1-yl)-1,3,5-triazin-2-yl)-4-methoxy-N-(pyrazin-2-yl)pyrrolidine-2-carboxamide | 1.30 (a) | 547 |
| 51 | (2S,4S)-1-(4-(3-Cyclopropyl-1H-pyrazol-5-ylamino)-6-(4-(pyrimidin-2-yl)piperazin-1-yl)-1,3,5-triazin-2-yl)-4-methoxy-N-(pyrazin-2-yl)pyrrolidine-2-carboxamide | 1.66 (a) 10.30 (h) | 585 |

TABLE 3-continued

| Example No. | Compound | HPLC ret. t. (min.) | [M + H]+ |
|---|---|---|---|
| 52 | 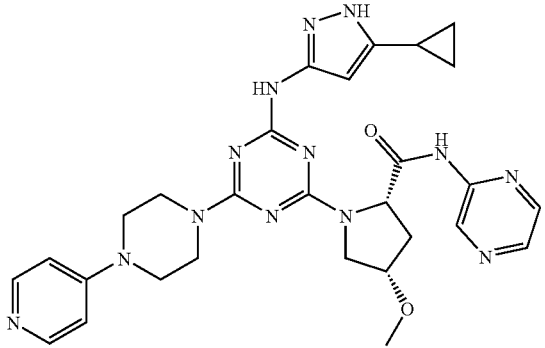 [SMILES: CO[C@H]1C[C@@H](C(=O)Nc2cnccn2)N(c2nc(Nc3cc(C4CC4)[nH]n3)nc(N3CCN(c4ccncc4)CC3)n2)C1]<br>(2S,4S)-1-(4-(5-Cyclopropyl-1H-pyrazol-3-ylamino)-6-(4-pyridin-4-yl)piperazin-1-yl)-1,3,5-triazin-2-yl)-4-methoxy-N-(pyrazin-2-yl)pyrrolidine-2-carboxamide | 2.16 (f) | 584 |
| 53 | 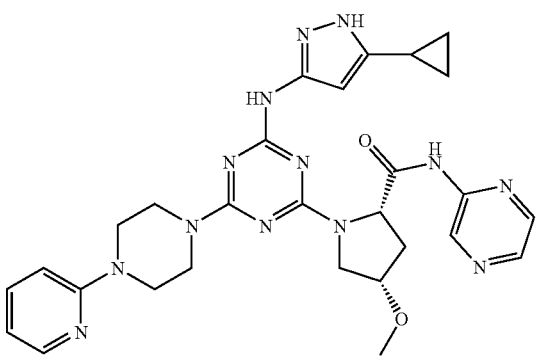 [SMILES: CO[C@H]1C[C@@H](C(=O)Nc2cnccn2)N(c2nc(Nc3cc(C4CC4)[nH]n3)nc(N3CCN(c4ccccn4)CC3)n2)C1]<br>(2S,4S)-1-(4-(5-Cyclopropyl-1H-pyrazol-3-ylamino)-6-(4-(pyridin-4-yl)piperazin-1-yl)-1,3,5-triazin-2-yl)-4-methoxy-N-(pyrazin-2-yl)pyrrolidine-2-carboxamide | 2.78 (f) | 584 |
| 54 | 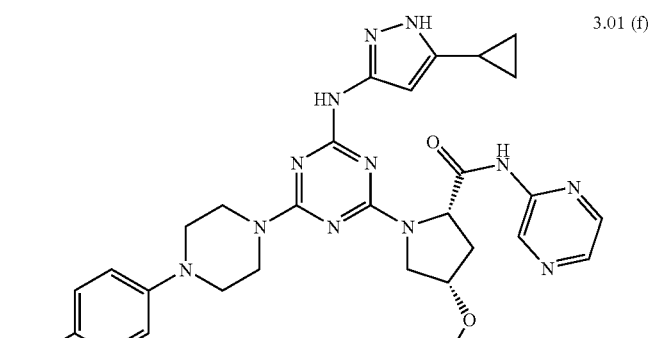<br>(2S,4S)-1-(4-(5-Cyclopropyl-1H-pyrazol-3-ylamino)-6-(4-(4-methoxyphenyl)piperazin-1-yl)-1,3,5-triazin-2-yl)-4-methoxy-N-(pyrazin-2-yl)pyrrolidine-2-carboxamide | 3.01 (f) | 613 |

TABLE 3-continued

| Example No. | Compound | HPLC ret. t. (min.) | [M + H]+ |
|---|---|---|---|
| 55 | 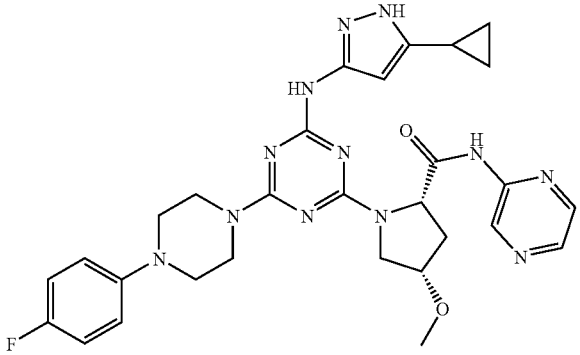 [SMILES: CO[C@H]1C[C@@H](C(=O)Nc2cnccn2)N(c2nc(Nc3cc(C4CC4)[nH]n3)nc(N3CCN(c4ccc(F)cc4)CC3)n2)C1]<br>(2S,4S)-1-(4-(5-Cyclopropyl-1H-pyrazol-3-ylamino)-6-(4-(4-fluorophenyl)piperazin-1-yl)-1,3,5-triazin-2-yl)-4-methoxy-N-(pyrazin-2-yl)pyrrolidine-2-carboxamide | 3.04 (f) | 601 |
| 56 | 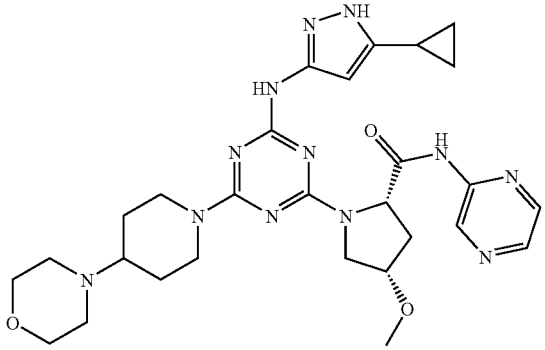 [SMILES: CO[C@H]1C[C@@H](C(=O)Nc2cnccn2)N(c2nc(Nc3cc(C4CC4)[nH]n3)nc(N3CCC(N4CCOCC4)CC3)n2)C1]<br>(2S,4S)-1-(4-(5-Cyclopropyl-1H-pyrazol-3-ylamino)-6-(4-morpholinopiperidin-1-yl)-1,3,5-triazin-2-yl)-4-methoxy-N-(pyrazin-2-yl)pyrrolidine-2-carboxamide | 1.33 (a) | 591 |
| 57 | 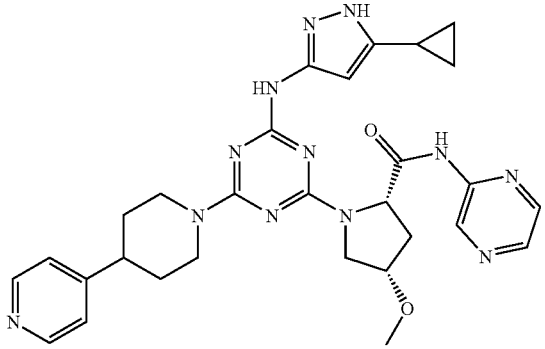 [SMILES: CO[C@H]1C[C@@H](C(=O)Nc2cnccn2)N(c2nc(Nc3cc(C4CC4)[nH]n3)nc(N3CCC(c4ccncc4)CC3)n2)C1]<br>(2S,4S)-1-(4-(5-Cyclopropyl-1H-pyrazol-3-ylamino)-6-(4-(pyridin-4-yl)piperidin-1-yl)-1,3,5-triazin-2-yl)-4-methoxy-N-(pyrazin-2-yl)pyrrolidine-2-carboxamide | 1.36 (a0 | 583 |

TABLE 3-continued

| Example No. | Compound | HPLC ret. t. (min.) | [M + H]+ |
|---|---|---|---|
| 58 | 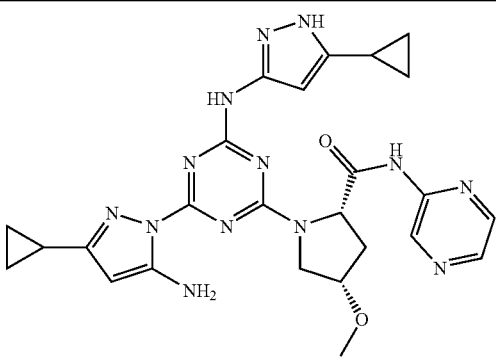<br>(2S,4S)-1-(4-(5-Amino-3-cyclopropyl-1H-pyrazol-1-yl)-6-(5-cyclopropyl-1H-pyrazol-3-ylamino)-1,3,5-triazin-2-yl)-4-methoxy-N-(pyrazin-2-yl)pyrrolidine-2-carboxamide | 1.69 (a) | 544 |
| 59 | 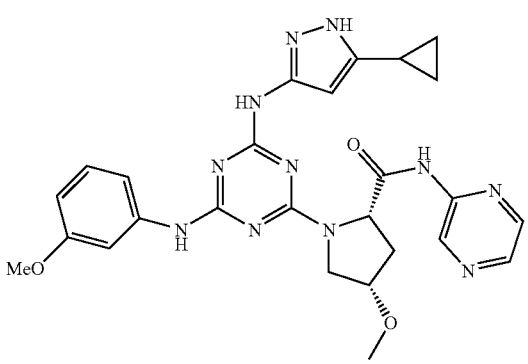 [SMILES: COc1cccc(Nc2nc(Nc3cc(C4CC4)[nH]n3)nc(N3C[C@@H](OC)C[C@H]3C(=O)Nc3cnccn3)n2)c1]<br>(2S,4S)-1-(4-(5-Cyclopropyl-1H-pyrazol-3-ylamino)-6-(3-methoxyphenylamino)-1,3,5-triazin-2-yl)-4-methoxy-N-(pyrazin-2-yl)pyrrolidine-2-carboxamide | 2.61 (c) | 544 |
| 60 | 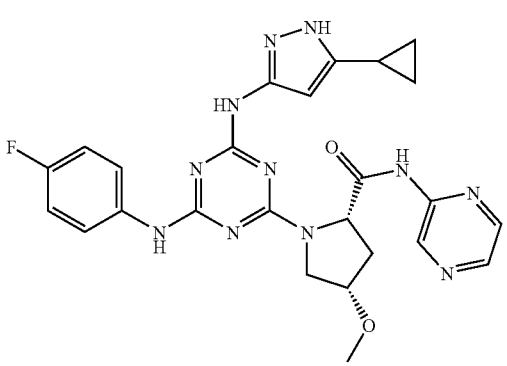 [SMILES: CO[C@H]1C[C@@H](C(=O)Nc2cnccn2)N(c2nc(Nc3ccc(F)cc3)nc(Nc3cc(C4CC4)[nH]n3)n2)C1]<br>(2S,4S)-1-(4-(5-Cyclopropyl-1H-pyrazol-3-ylamino)-6-(4-fluorophenylamino)-1,3,5-triazin-2-yl)-4-methoxy-N-(pyrazin-2-yl)pyrrolidine-2-carboxamide | 2.79 (f) | 532 |

TABLE 3-continued

| Example No. | Compound | HPLC ret. t. (min.) | [M + H]+ |
|---|---|---|---|
| 61 | 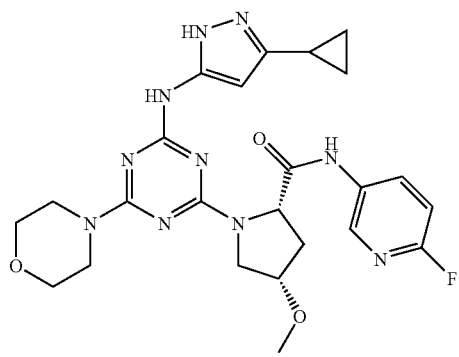 [SMILES: CO[C@H]1C[C@@H](C(=O)Nc2ccc(F)nc2)N(c2nc(Nc3cc(C4CC4)n[nH]3)nc(N3CCOCC3)n2)C1]<br>(2S,4S)-1-(4,6-Bis(5-cyclopropyl-1H-pyrazol-3-ylamino)-1,3,5-triazin-2-yl)-4-methoxy-N-(pyrazin-2-yl)pyrrolidine-2-carboxamide | 1.77 (a) | 544 |

Example 62

(2S,4S)-1-(4-(3-Cyclopropyl-1H-pyrazol-5-ylamino)-6-morpholino-1,3,5-triazin-2-yl)-N-(6-fluoropyridin-3-yl)-4-methoxypyrrolidine-2-carboxamide

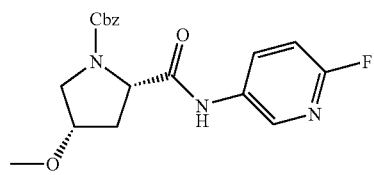 [SMILES: CO[C@H]1C[C@@H](C(=O)Nc2ccc(F)nc2)N(C(=O)OCc2ccccc2)C1]

62A. (2S,4S)-Benzyl 2-(6-fluoropyridin-3-ylcarbamoyl)-4-methoxypyrrolidine-1-carboxylate

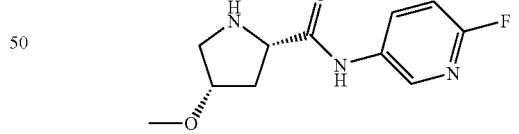

To a solution of 6-fluoropyridin-3-amine (500 mg, 4.46 mmol) in THF (15 mL) was added isopropylmagnesium chloride (2.0 M THF solution, 2.12 mL, 4.24 mmol) dropwise at 0° C. The resulting reaction mixture was stirred at room temperature for 30 min. A solution of (2S,4S)-1-benzyl 2-methyl 4-methoxypyrrolidine-1,2-dicarboxylate 18B (435 mg, 1.49 mmol) in THF (2 mL) was added to the reaction mixture. The reaction mixture was stirred at room temperature for 4 h and quenched with methanol (3 mL). The crude product was purified by prep. HPLC to give (2S,4S)-benzyl 4-methoxy-2-(pyrazin-2-ylcarbamoyl)pyrrolidine-1-carboxylate 62A (424 mg, 80%) as an oil. LC/MS [M+H-Boc]+: 240; Ret time (Method F): 2.43 min.

62B. (2S,4S)—N-(6-Fluoropyridin-3-yl)-4-methoxypyrrolidine-2-carboxamide

To a stirred suspension of palladium on carbon (10%, 80 mg) in methanol (100 mL) was added a solution of (2S,4S)-benzyl 4-methoxy-2-(pyrazin-2-ylcarbamoyl)pyrrolidine-1-carboxylate 62A (400 mg, 1.12 mmol) in methanol (100 mL) under nitrogen. The suspension was hydrogenated with a hydrogen balloon atmosphere overnight. The resulting suspension was filtered through a pad of celite and washed with methanol. Concentration of the filtrate gave the product as an oil (250 mg, 100%) which was used without purification in the next step. LC/MS [M+H]$^+$: 240; Ret time (Method F): 0.91 min.

62C. (2S,4S)-1-(4-Chloro-6-(3-cyclopropyl-1H-pyrazol-5-ylamino)-1,3,5-triazin-2-yl)-N-(6-fluoropyridin-3-yl)-4-methoxypyrrolidine-2-carboxamide

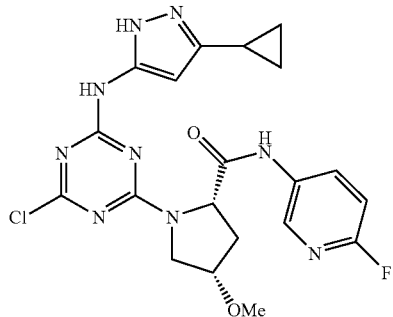 [SMILES: CO[C@H]1C[C@@H](C(=O)Nc2ccc(F)nc2)N(c2nc(Cl)nc(Nc3cc(C4CC4)n[nH]3)n2)C1]

(2S,4S)-1-(4-Chloro-6-(3-cyclopropyl-1H-pyrazol-5-ylamino)-1,3,5-triazin-2-yl)-N-(6-fluoropyridin-3-yl)-4-methoxypyrrolidine-2-carboxamide 62C was prepared using the procedure described in 1C. LC/MS [M+H]$^+$: 474/476; Ret time (Method F): 2.55 min. Morpholine (0.2 mL, excess) was added to a solution of crude 62C (150 mg crude) in THF. The reaction mixture was stirred at room temperature for 3 h and the product was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 62. LC/MS [M+H]$^+$: 525; Ret time (Method F): 2.38 min.

Examples 63 and 64

Examples 63 and 64 are disclosed in Table 4 and were prepared using procedures described above in Example 62 starting from 62C.

TABLE 4

| Example No. | Compound | HPLC ret. time (min.) | [M + H]$^+$ |
|---|---|---|---|
| 63 | (2S,4S)-1-(4-(3-Cyclopropyl-1H-pyrazol-5-ylamino)-6-(4-methylpiperazin-1-yl)-1,3,5-triazin-2-yl)-N-(6-fluoropyridin-3-yl)-4-methoxypyrrolidine-2-carboxamide | 2.22 | 538 |
| 64 | (2S,4S)-1-(4-(3-Cyclopropyl-1H-pyrazol-5-ylamino)-6-(4-(2-methoxyethyl)piperazin-1-yl)-1,3,5-triazin-2-yl)-N-(6-fluoropyridin-3-yl)-4-methoxypyrrolidine-2-carboxamide | 1.96 | 582 |

Example 65

(2S,4R)-1-(4-(3-Cyclopropyl-1H-pyrazol-5-ylamino)-6-morpholino-1,3,5-triazin-2-yl)-4-fluoro-N-(pyrazin-2-yl)pyrrolidine-2-carboxamide

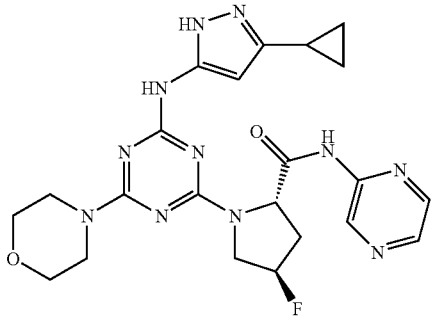 [SMILES: O=C(Nc1cnccn1)[C@@H]1C[C@@H](F)CN1c1nc(Nc2cc(C3CC3)n[nH]2)nc(N2CCOCC2)n1]

65A. (2S,4R)-tert-Butyl 4-fluoro-2-(pyrazin-2-ylcarbamoyl)pyrrolidine-1-carboxylate

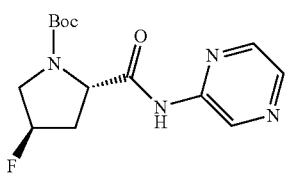 [SMILES: CC(C)(C)OC(=O)N1C[C@H](F)C[C@H]1C(=O)Nc1cnccn1]

To a solution of aminopyrazine (3.85 g, 40.5 mmol) in THF (120 mL) was added isopropylmagnesium chloride (2.0 M THF solution, 19 mL, 38 mmol) dropwise at 0° C. The resulting slurry was stirred at room temperature for 30 min. A solution of commercially available (2S,4R)-1-tert-butyl 2-methyl 4-fluoropyrrolidine-1,2-dicarboxylate (3.2 g, 12.9 mmol) in THF (10 mL) was added to the slurry. The reaction mixture was stirred at room temperature for 4 h and quenched with methanol (3 mL). After concentration in vacuo, ethyl acetate (120 mL) and 1N HCl (60 mL) were added to the residue. The organic layers were washed with 1N HCl, water, brine, and dried over $Na_2SO_4$, and filtered. Concentration gave (2S,4R)-tert-butyl 4-fluoro-2-(pyrazin-2-ylcarbamoyl) pyrrolidine-1-carboxylate 65A (4.1 g, 100%) as a colorless foam. LC/MS [M+H]$^+$: 311; Ret time (Method F): 1.46 min.

65B. (2S,4R)-4-Fluoro-N-(pyrazin-2-yl)pyrrolidine-2-carboxamide

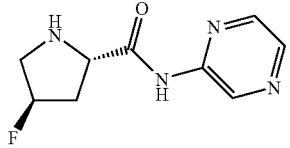 [SMILES: O=C(Nc1cnccn1)[C@@H]1C[C@@H](F)CN1]

To a solution of (2S,4R)-tert-butyl 4-fluoro-2-(pyrazin-2-ylcarbamoyl)pyrrolidine-1-carboxylate 65A (4.1 g, 12.3 mmol) in $CH_2Cl_2$ (120 mL) was added TFA (10 mL). The reaction mixture was stirred at rt overnight. After concentration in vacuo, the residue was used for the next step without purification. LC/MS [M+H]$^+$: 211; Ret time (Method F): 0.30 min.

65C. (2S,4R)-1-(4-Chloro-6-(3-cyclopropyl-1H-pyrazol-5-ylamino)-1,3,5-triazin-2-yl)-4-fluoro-N-(pyrazin-2-yl)pyrrolidine-2-carboxamide

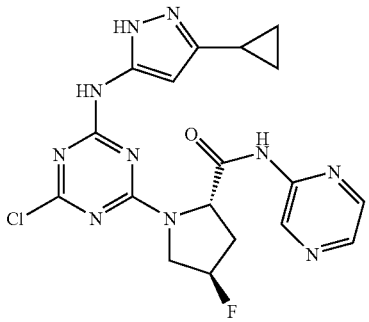 [SMILES: O=C(Nc1cnccn1)[C@@H]1C[C@@H](F)CN1c1nc(Cl)nc(Nc2cc(C3CC3)n[nH]2)n1]

65C was prepared using the procedure described in 1C. LC/MS [M+H]$^+$: 445/447; Ret time (Method F): 2.41 min.

65 was prepared using the procedure described in 1. LC/MS [M+1-1]$^+$: 496; Ret time (Method F): 2.29 min.

Examples 66 to 78

Examples 66 to 78 are disclosed in Table 5 and were prepared using procedures described above in Example 65.

TABLE 5

| Example No. | Compound | HPLC ret. t. (min.) | [M + H]+ |
|---|---|---|---|
| 66 | 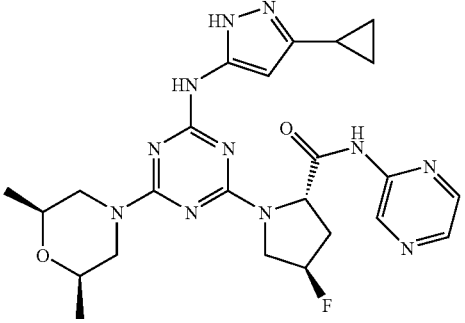 [SMILES: C[C@@H]1CN(c2nc(Nc3cc(C4CC4)n[nH]3)nc(N3C[C@H](F)C[C@H]3C(=O)Nc3cnccn3)n2)C[C@H](C)O1] (2S,4R)-1-(4-(3-Cyclopropyl-1H-pyrazol-5-ylamino)-6-((2S,6R)-2,6-dimethylmorpholino)-1,3,5-triazin-2-yl)-4-fluoro-N-(pyrazin-2-yl)pyrrolidine-2-carboxamide | 2.53 (f) | 524 |
| 67 | 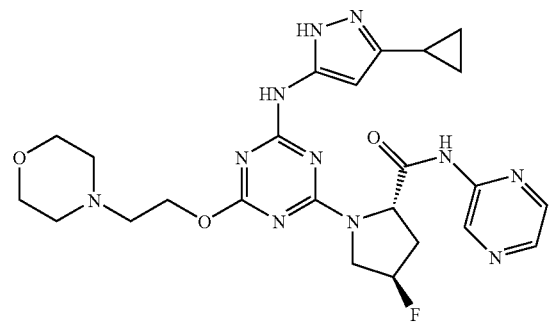 [SMILES: O=C(Nc1cnccn1)[C@@H]1C[C@@H](F)CN1c1nc(Nc2cc(C3CC3)n[nH]2)nc(OCCN2CCOCC2)n1] (2S,4R)-1-(4-(3-Cyclopropyl-1H-pyrazol-5-ylamino)-6-(2-morpholinoethoxy)-1,3,5-triazin-2-yl)-4-fluoro-N-(pyrazin-2-yl)pyrrolidine-2-carboxamide | 2.04 (f) | 540 |
| 68 | 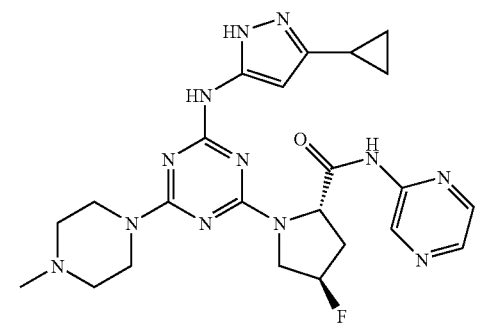 [SMILES: CN1CCN(c2nc(Nc3cc(C4CC4)n[nH]3)nc(N3C[C@H](F)C[C@H]3C(=O)Nc3cnccn3)n2)CC1] (2S,4R)-1-(4-(3-Cyclopropyl-1H-pyrazol-5-ylamino)-6-(4-methylpiperazin-1-yl)-1,3,5-triazin-2-yl)-4-fluoro-N-(pyrazin-2-yl)pyrrolidine-2-carboxamide | 1.78 (f) | 509 |

TABLE 5-continued

| Example No. | Compound | HPLC ret. t. (min.) | [M + H]+ |
|---|---|---|---|
| 69 | 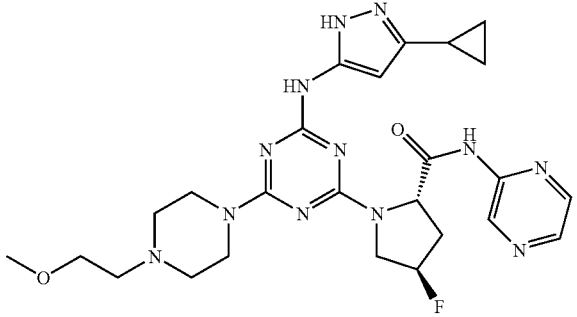 [SMILES: COCCN1CCN(c2nc(Nc3cc(C4CC4)n[nH]3)nc(N3C[C@H](F)C[C@H]3C(=O)Nc3cnccn3)n2)CC1]<br>(2S,4R)-1-(4-(3-Cyclopropyl-1H-pyrazol-5-ylamino)-6-(4-(2-methoxyethyl)piperazin-1-yl)-1,3,5-triazin-2-yl)-4-fluoro-N-(pyrazin-2-yl)pyrrolidine-2-carboxamide | 1.89 (f) | 553 |
| 70 | 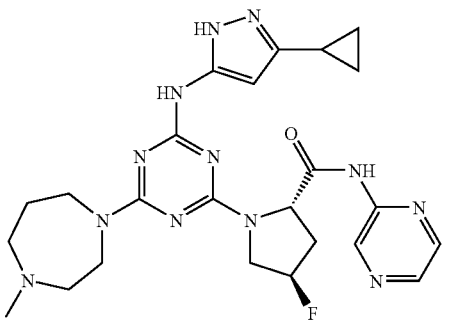 [SMILES: CN1CCCN(c2nc(Nc3cc(C4CC4)n[nH]3)nc(N3C[C@H](F)C[C@H]3C(=O)Nc3cnccn3)n2)CC1]<br>(2S,4R)-1-(4-(3-Cyclopropyl-1H-pyrazol-5-ylamino)-6-(4-methyl-1,4-diazepan-1-yl)-1,3,5-triazin-2-yl)-4-fluoro-N-(pyrazin-2-yl)pyrrolidine-2-carboxamide | 1.74 (f) | 523 |
| 71 | 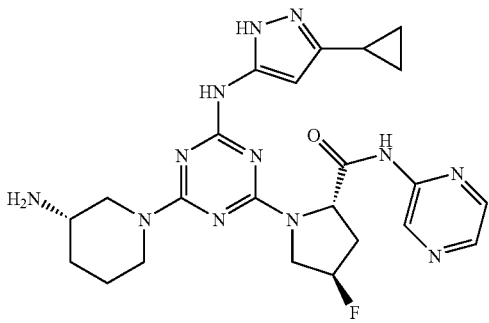 [SMILES: N[C@H]1CCCN(c2nc(Nc3cc(C4CC4)n[nH]3)nc(N3C[C@H](F)C[C@H]3C(=O)Nc3cnccn3)n2)C1]<br>(2S,4R)-1-(4-((S)-3-Aminopiperidin-1-yl)-6-(3-cyclopropyl-1H-pyrazol-5-ylamino)-1,3,5-triazin-2-yl)-4-fluoro-N-(pyrazin-2-yl)pyrrolidine-2-carboxamide | 1.82 (f) | 509 |

TABLE 5-continued

| Example No. | Compound | HPLC ret. t. (min.) | [M + H]+ |
|---|---|---|---|
| 72 | 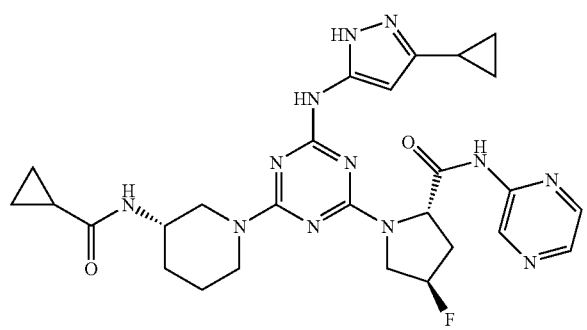 [SMILES: O=C(N[C@H]1CCCN(c2nc(Nc3cc(C4CC4)n[nH]3)nc(N3C[C@H](F)C[C@H]3C(=O)Nc3cnccn3)n2)C1)C1CC1]<br>(2S,4R)-1-(4-((S)-3-(Cyclopropanecarboxamido)piperidin-1-yl)-6-(3-cyclopropyl-1H-pyrazol-5-ylamino)-1,3,5-triazin-2-yl)-4-fluoro-N-(pyrazin-2-yl)pyrrolidine-2-carboxamide | 2.52 (f) | 577 |
| 73 | 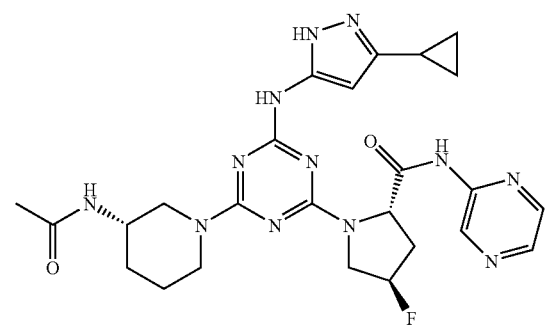 [SMILES: CC(=O)N[C@H]1CCCN(c2nc(Nc3cc(C4CC4)n[nH]3)nc(N3C[C@H](F)C[C@H]3C(=O)Nc3cnccn3)n2)C1]<br>(2S,4R)-1-(4-((S)-3-Acetamidopiperidin-1-yl)-6-(3-cyclopropyl-1H-pyrazol-5-ylamino)-1,3,5-triazin-2-yl)-4-fluoro-N-(pyrazin-2-yl)pyrrolidine-2-carboxamide | 2.29 (f) | 551 |
| 74 | 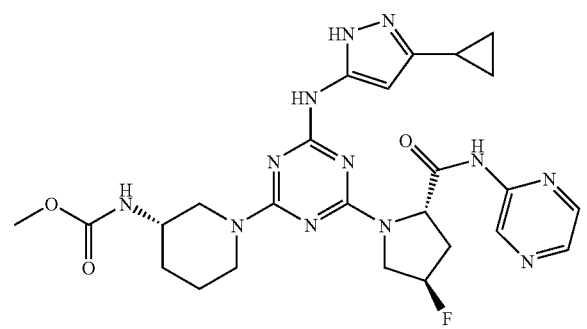 [SMILES: COC(=O)N[C@H]1CCCN(c2nc(Nc3cc(C4CC4)n[nH]3)nc(N3C[C@H](F)C[C@H]3C(=O)Nc3cnccn3)n2)C1]<br>Methyl (S)-1-(4-(3-cyclopropyl-1H-pyrazol-5-ylamino)-6-((2S,4R)-4-fluoro-2-(pyrazin-2-ylcarbamoyl)pyrrolidin-1-yl)-1,3,5-triazin-2-yl)piperidin-3-ylcarbamate | 2.47 (f) | 567 |

TABLE 5-continued

| Example No. | Compound | HPLC ret. t. (min.) | [M + H]+ |
|---|---|---|---|
| 75 | 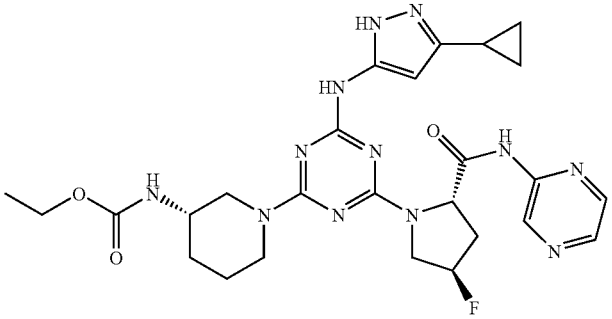 [SMILES: CCOC(=O)N[C@H]1CCCN(c2nc(Nc3cc(C4CC4)n[nH]3)nc(N3C[C@H](F)C[C@H]3C(=O)Nc3cnccn3)n2)C1]<br>Ethyl (S)-1-(4-(3-cyclopropyl-1H-pyrazol-5-ylamino)-6-((2S,4R)-4-fluoro-2-(pyrazin-2-ylcarbamoyl)pyrrolidin-1-yl)-1,3,5-triazin-2-yl)piperidin-3-ylcarbamate | 2.69 (f) | 581 |
| 76 | 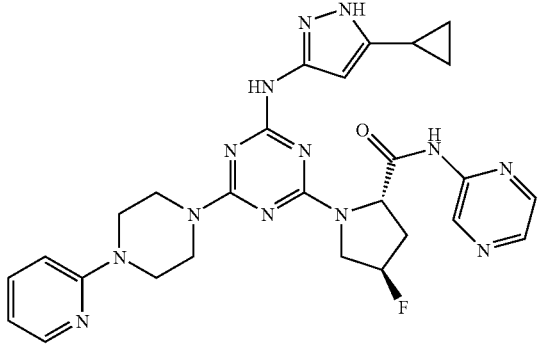 [SMILES: O=C(Nc1cnccn1)[C@@H]1C[C@@H](F)CN1c1nc(Nc2cc(C3CC3)[nH]n2)nc(N2CCN(c3ccccn3)CC2)n1]<br>(2S,4R)-1-(4-(5-Cyclopropyl-1H-pyrazol-3-ylamino)-6-(4-(pyridin-2-yl)piperazin-1-yl)-1,3,5-triazin-2-yl)-4-fluoro-N-(pyrazin-2-yl)pyrrolidine-2-carboxamide | 2.09 (f) | 572 |
| 77 | 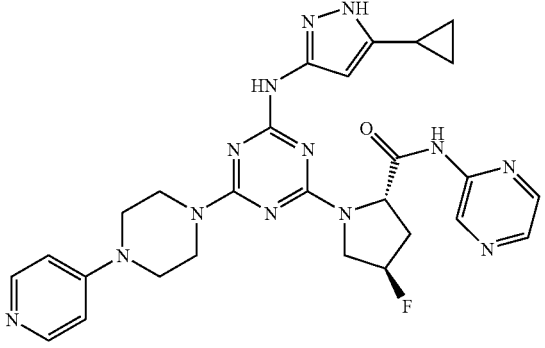 [SMILES: O=C(Nc1cnccn1)[C@@H]1C[C@@H](F)CN1c1nc(Nc2cc(C3CC3)[nH]n2)nc(N2CCN(c3ccncc3)CC2)n1]<br>(2S,4R)-1-(4-(5-Cyclopropyl-1H-pyrazol-3-ylamino)-6-(4-(pyridin-4-yl)piperazin-1-yl)-1,3,5-triazin-2-yl)-4-fluoro-N-(pyrazin-2-yl)pyrrolidine-2-carboxamide | 2.10 (f) | 572 |

TABLE 5-continued

| Example No. | Compound | HPLC ret. t. (min.) | [M + H]+ |
|---|---|---|---|
| 78 | 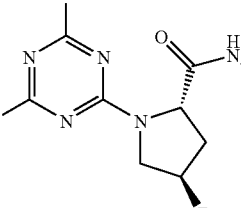<br>(2S,4R)-1-(4-(5-Cyclopropyl-1H-pyrazol-3-ylamino)-6-((1R,5S)-3-methyl-3,8-diazabicyclo[3.2.1]octan-8-yl)-1,3,5-triazin-2-yl)-4-fluoro-N-(pyrazin-2-yl)pyrrolidine-2-carboxamide | 2.05 (f) | 535 |

Example 79

(2S,4R)-1-(4-(3-Cyclopropyl-1H-pyrazol-5-ylamino)-6-morpholino-1,3,5-triazin-2-yl)-4-fluoro-N-(6-fluoropyridin-3-yl)pyrrolidine-2-carboxamide

79A. (2S,4R)-4-Fluoro-N-(6-fluoropyridin-3-yl)pyrrolidine-2-carboxamide

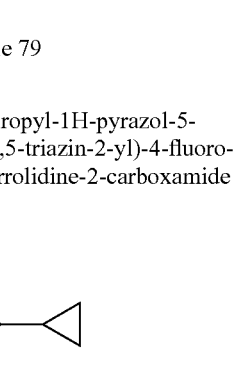

(2S,4R)-4-Fluoro-N-(6-fluoropyridin-3-yl)pyrrolidine-2-carboxamide 79A was prepared from (2S,4R)-1-tert-butyl 2-methyl 4-fluoropyrrolidine-1,2-dicarboxylate as described for 65A and 65B. LC/MS [M+H]+: 228; Ret time (Method C): 0.57 min.

79B. (2S,4R)-1-(4-Chloro-6-(3-cyclopropyl-1H-pyrazol-5-ylamino)-1,3,5-triazin-2-yl)-4-fluoro-N-(6-fluoropyridin-3-yl)pyrrolidine-2-carboxamide

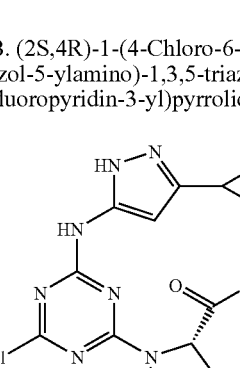

79B was prepared from 1A and 79A as described for 1C: MS: 462/464(M+H)+, HPLC (Method F) Ret time: 2.61 min.
Compound 79 was prepared from morpholine and 79B as described for 1. LC/MS [M+H]+: 513; Ret time (Method F): 2.43 min.

Example 80

(2S,4R)-1-(4-(3-Cyclopropyl-1H-pyrazol-5-ylamino)-6-(4-methylpiperazin-1-yl)-1,3,5-triazin-2-yl)-4-fluoro-N-(6-fluoropyridin-3-yl)pyrrolidine-2-carboxamide

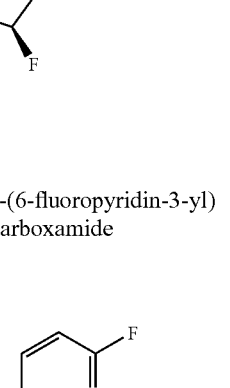

Compound 80 was prepared from N-Methyl piperazine and 79B as described for 1. LC/MS [M+H]⁺: 526; Ret time (Method F): 1.91 min.

Example 81

(2S,4R)-1-(4-(3-Cyclopropyl-1H-pyrazol-5-ylamino)-6-(4-(2-methoxyethyl)piperazin-1-yl)-1,3,5-triazin-2-yl)-4-fluoro-N-(6-fluoropyridin-3-yl)pyrrolidine-2-carboxamide

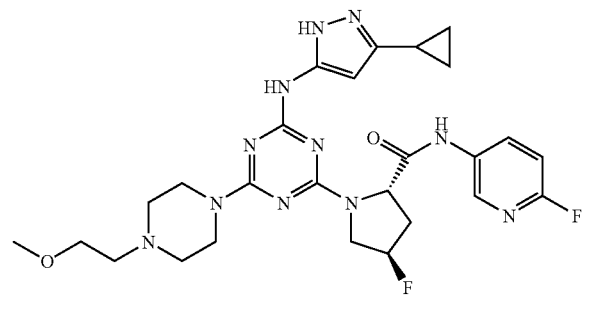 [SMILES: COCCN1CCN(c2nc(Nc3cc(C4CC4)n[nH]3)nc(N3C[C@H](F)C[C@H]3C(=O)Nc3ccc(F)nc3)n2)CC1]

Compound 81 was prepared from N-methoxyethyl piperazine and 79B as described for 1. LC/MS [M+H]⁺: 570; Ret time (Method F): 1.98 min.

Example 82

(2S,4R)-1-(4-(3-Cyclopropyl-1H-pyrazol-5-ylamino)-6-morpholino-1,3,5-triazin-2-yl)-4-fluoro-N-(1,2,4-thiadiazol-5-yl)pyrrolidine-2-carboxamide

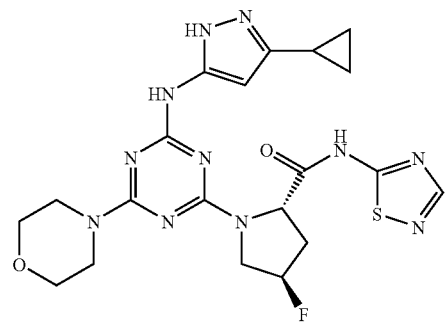 [SMILES: O=C(Nc1ncns1)[C@@H]1C[C@@H](F)CN1c1nc(Nc2cc(C3CC3)n[nH]2)nc(N2CCOCC2)n1]

82A. (2S,4R)-4-Fluoro-N-(1,2,4-thiadiazol-5-yl)pyrrolidine-2-carboxamide

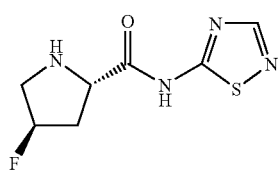 [SMILES: O=C(Nc1ncns1)[C@@H]1C[C@@H](F)CN1]

(2S,4R)-4-Fluoro-N-(1,2,4-thiadiazol-5-yl)pyrrolidine-2-carboxamide 82A was prepared from (2S,4R)-1-tert-butyl 2-methyl 4-fluoropyrrolidine-1,2-dicarboxylate as described for 65A and 65B. LC/MS [M+H]⁺: 217; Ret time (Method F): 0.28 min.

82B. (2S,4R)-1-(4-Chloro-6-(3-cyclopropyl-1H-pyrazol-5-ylamino)-1,3,5-triazin-2-yl)-4-fluoro-N-(1,2,4-thiadiazol-5-yl)pyrrolidine-2-carboxamide

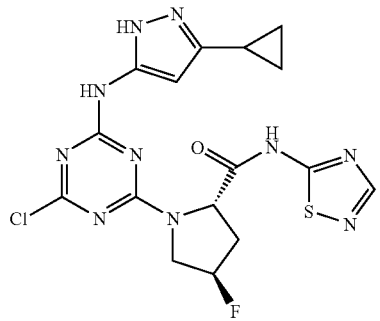 [SMILES: O=C(Nc1ncns1)[C@@H]1C[C@@H](F)CN1c1nc(Cl)nc(Nc2cc(C3CC3)n[nH]2)n1]

82B was prepared from 1A and 83A as described for 1C. LC/MS [M+H]⁺: 451/453; Ret time (Method F): 2.59 min.

Compound 82 was prepared from morpholine and 82B as described for 1. LC/MS [M+H]⁺: 502; Ret time (Method F): 2.77 min.

Example 83

(2S,4R)-1-(4-(3-Cyclopropyl-1H-pyrazol-5-ylamino)-6-(4-methylpiperazin-1-yl)-1,3,5-triazin-2-yl)-4-fluoro-N-(1,2,4-thiadiazol-5-yl)pyrrolidine-2-carboxamide

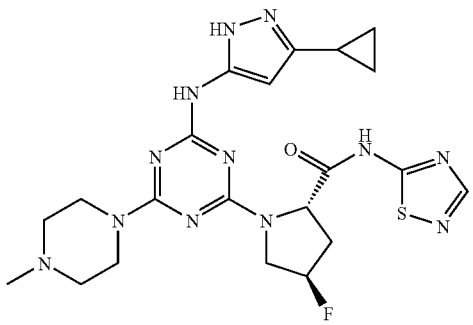 [SMILES: CN1CCN(c2nc(Nc3cc(C4CC4)n[nH]3)nc(N3C[C@H](F)C[C@H]3C(=O)Nc3ncns3)n2)CC1]

Compound 83 was prepared from N-Methyl piperazine and 82B as described for 1. LC/MS [M+H]⁺: 515; Ret time (Method F): 1.91 min.

Example 84

(2S,4R)-1-(4-(3-Cyclopropyl-1H-pyrazol-5-ylamino)-6-(4-(2-methoxyethyl)piperazin-1-yl)-1,3,5-triazin-2-yl)-4-fluoro-N-(1,2,4-thiadiazol-5-yl)pyrrolidine-2-carboxamide

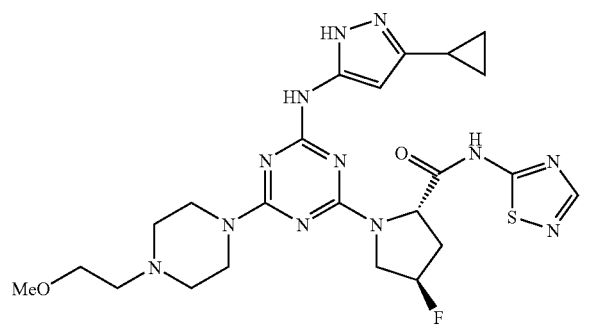 [SMILES: COCCN1CCN(c2nc(Nc3cc(C4CC4)n[nH]3)nc(N3C[C@H](F)C[C@H]3C(=O)Nc3ncns3)n2)CC1]

Compound 84 was prepared from N-methoxyethyl piperazine and 82B as described for 1. LC/MS [M+H]⁺: 559; Ret time (Method F): 2.34 min.

Example 85

(2S,4S)-1-(4-(3-Cyclopropyl-1H-pyrazol-5-ylamino)-6-morpholino-1,3,5-triazin-2-yl)-4-hydroxy-N-(pyrazin-2-yl)pyrrolidine-2-carboxamide

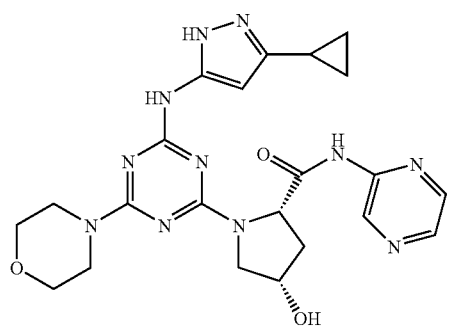 [SMILES: O=C(Nc1cnccn1)[C@@H]1C[C@H](O)CN1c1nc(Nc2cc(C3CC3)n[nH]2)nc(N2CCOCC2)n1]

85A. (2S,4S)-4-Hydroxy-N-(pyrazin-2-yl)pyrrolidine-2-carboxamide

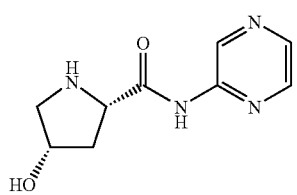 [SMILES: O=C(Nc1cnccn1)[C@@H]1C[C@H](O)CN1]

(2S,4S)-4-Hydroxy-N-(pyrazin-2-yl)pyrrolidine-2-carboxamide 85A was prepared from (2S,4S)-1-tert-butyl 2-methyl 4-hydroxypyrrolidine-1,2-dicarboxylate as described for 65A and 65B. LC/MS [M+H]⁺: 209; Ret time (Method F): 0.27 min.

85B. (2S,4S)-1-(4-Chloro-6-(3-cyclopropyl-1H-pyrazol-5-ylamino)-1,3,5-triazin-2-yl)-4-hydroxy-N-(pyrazin-2-yl)pyrrolidine-2-carboxamide

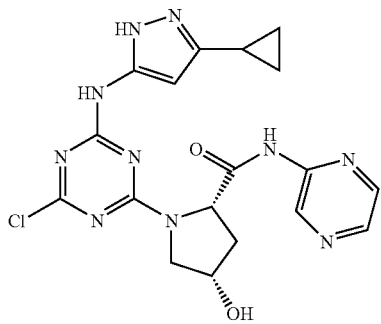 [SMILES: O=C(Nc1cnccn1)[C@@H]1C[C@H](O)CN1c1nc(Cl)nc(Nc2cc(C3CC3)n[nH]2)n1]

Compound 85B was prepared from 1A and 85A as described for 1C. LC/MS [M+H]⁺: 443/445; Ret time (Method F): 2.18 min.

Compound 85 was prepared from morpholine and 85B as described for 1: MS: 494 (M+H)⁺, HPLC (Method F) Ret time: 2.20 min.

Example 86

(2S,4S)-1-(4-(3-Cyclopropyl-1H-pyrazol-5-ylamino)-6-(4-methylpiperazin-1-yl)-1,3,5-triazin-2-yl)-4-hydroxy-N-(pyrazin-2-yl)pyrrolidine-2-carboxamide

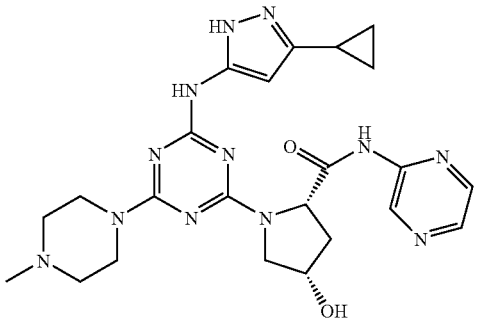 [SMILES: CN1CCN(c2nc(Nc3cc(C4CC4)n[nH]3)nc(N3C[C@@H](O)C[C@H]3C(=O)Nc3cnccn3)n2)CC1]

Compound 86 was prepared from 1-methylpiperazine and 85B as described for 1. LC/MS [M+H]⁺: 507; Ret time (Method F): 1.64 min.

Example 87

(2S,4S)-1-(4-(3-Cyclopropyl-1H-pyrazol-5-ylamino)-6-(4-(2-methoxyethyl)piperazin-1-yl)-1,3,5-triazin-2-yl)-4-hydroxy-N-(pyrazin-2-yl)pyrrolidine-2-carboxamide

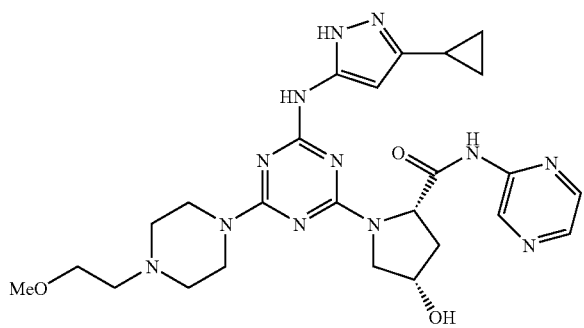 [SMILES: COCCN1CCN(c2nc(Nc3cc(C4CC4)n[nH]3)nc(N3C[C@@H](O)C[C@H]3C(=O)Nc3cnccn3)n2)CC1]

Compound 87 was prepared from 1-(2-methoxyethyl)piperazine and 85B as described for 1. LC/MS [M+H]$^+$: 551; Ret time (Method F): 1.73 min.

Example 88

(2S,4S)-1-(4-(5-Cyclopropyl-1H-pyrazol-3-ylamino)-6-morpholino-1,3,5-triazin-2-yl)-4-hydroxy-N-(thiazol-2-yl)pyrrolidine-2-carboxamide

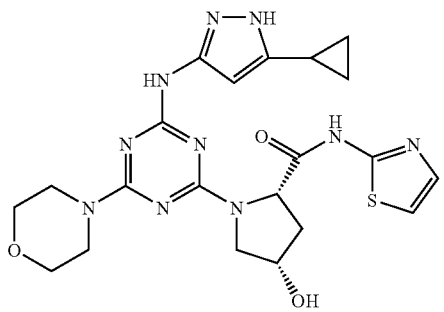 [SMILES: O=C(Nc1nccs1)[C@@H]1C[C@H](O)CN1c1nc(Nc2cc(C3CC3)[nH]n2)nc(N2CCOCC2)n1]

88A. (2S,4S)-4-Hydroxy-N-(thiazol-2-yl)pyrrolidine-2-carboxamide (2S,4S)-4-Hydroxy-N-(thiazol-2-yl)pyrrolidine-2-carboxamide 88A was prepared from (2S,4S)-1-tert-butyl 2-methyl 4-hydroxypyrrolidine-1,2-dicarboxylate and 2-Aminothiazole as described for 65A and 65B. LC/MS [M+H]$^+$: 214; Ret time (Method F): 0.35 min.

88B. (2S,4S)-1-(4-Chloro-6-(5-cyclopropyl-1H-pyrazol-3-ylamino)-1,3,5-triazin-2-yl)-4-hydroxy-N-(thiazol-2-yl)pyrrolidine-2-carboxamide 88B was prepared from 1A and 88A as described for 1C. LC/MS [M+H]$^+$: 448/450; Ret time (Method F): 2.34 min.

Compound 88 was prepared from morpholine and 88B as described for 1. LC/MS [M+H]$^+$: 499; Ret time (Method F): 2.36 min.

Examples 89 to 95

Examples 89 to 95 are disclosed in Table 6 and were prepared using procedures that are described above in Example 88.

TABLE 6

| Example No. | Compound | HPLC ret. time (min.) | [M + H]$^+$ |
|---|---|---|---|
| 89 | (2S,4S)-1-(4-(5-Cyclopropyl-1H-pyrazol-3-ylamino)-6-(5-methyl-2,5-diazabicyclo[2.2.1]heptan-2-yl)-1,3,5-triazin-2-yl)-4-hydroxy-N-(thiazol-2-yl)pyrrolidine-2-carboxamide | 2.12 (f) | 524 |

TABLE 6-continued

| Example No. | Compound | HPLC ret. time (min.) | [M + H]+ |
|---|---|---|---|
| 90 | (2S,4S)-1-(4-(3-Cyclopropyl-1H-pyrazol-5-ylamino)-6-(4-methylpiperazin-1-yl)-1,3,5-triazin-2-yl)-4-hydroxy-N-(thiazol-2-yl)pyrrolidine-2-carboxamide | 1.77 (f) | 512 |
| 91 | (2S,4S)-1-(4-(3-Cyclopropyl-1H-pyrazol-5-ylamino)-6-(4-(2-methoxyethyl)piperazin-1-yl)-1,3,5-triazin-2-yl)-4-hydroxy-N-(thiazol-2-yl)pyrrolidine-2-carboxamide | 2.28 (f) | 556 |
| 92 | (2S,4S)-1-(4-(5-Cyclopropyl-1H-pyrazol-3-ylamino)-6-(4-(pyridin-4-yl)piperazin-1-yl)-1,3,5-triazin-2-yl)-4-hydroxy-N-(thiazol-2-yl)pyrrolidine-2-carboxamide | 2.40 (f) | 575 |

TABLE 6-continued

| Example No. | Compound | HPLC ret. time (min.) | [M + H]+ |
|---|---|---|---|
| 93 | 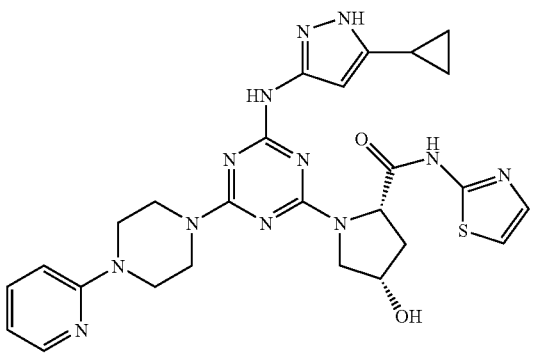 [SMILES: O=C(Nc1nccs1)[C@@H]1C[C@H](O)CN1c1nc(Nc2cc(C3CC3)[nH]n2)nc(N2CCN(c3ccccn3)CC2)n1]<br>(2S,4S)-1-(4-(5-Cyclopropyl-1H-pyrazol-3-ylamino)-6-(4-(pyridin-2-yl)piperazin-1-yl)-1,3,5-triazin-2-yl)-4-hydroxy-N-(thiazol-2-yl)pyrrolidine-2-carboxamide | 2.35 (f) | 575 |
| 94 | 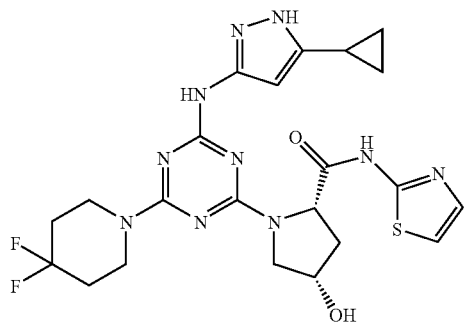 [SMILES: O=C(Nc1nccs1)[C@@H]1C[C@H](O)CN1c1nc(Nc2cc(C3CC3)[nH]n2)nc(N2CCC(F)(F)CC2)n1]<br>(2S,4S)-1-(4-(5-Cyclopropyl-1H-pyrazol-3-ylamino)-6-(4,4-difluoropiperidin-1-yl)-1,3,5-triazin-2-yl)-4-hydroxy-N-(thiazol-2-yl)pyrrolidine-2-carboxamide | 2.78 (f) | 533 |
| 95 | 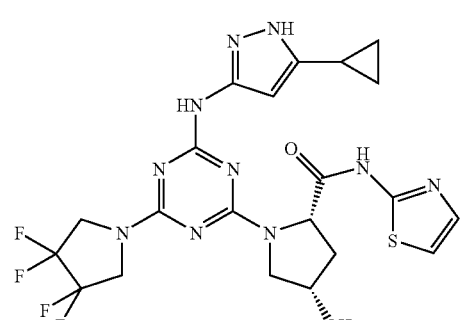<br>(2S,4S)-1-(4-(5-Cyclopropyl-1H-pyrazol-3-ylamino)-6-(3,3,4,4-tetrafluoropyrrolidin-1-yl)-1,3,5-triazin-2-yl)-4-hydroxy-N-(thiazol-2-yl)pyrrolidine-2-carboxamide | 3.04 (f) | 555 |

Example 96

(2S,4S)-1-(4-(5-Cyclopropyl-1H-pyrazol-3-ylamino)-6-morpholino-1,3,5-triazin-2-yl)-4-hydroxy-N-(5-methylthiazol-2-yl)pyrrolidine-2-carboxamide

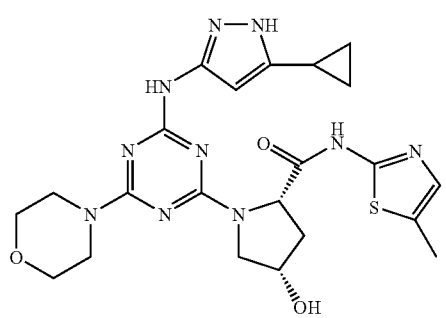 [SMILES: Cc1cnc(NC(=O)[C@@H]2C[C@H](O)CN2c2nc(Nc3cc(C4CC4)[nH]n3)nc(N3CCOCC3)n2)s1]

96A. (2S,4S)-tert-Butyl 4-hydroxy-2-(5-methylthiazol-2-ylcarbamoyl) pyrrolidine-1-carboxylate

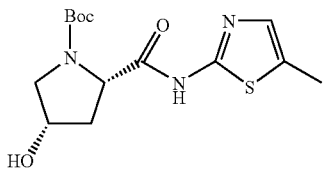 [SMILES: Cc1cnc(NC(=O)[C@@H]2C[C@H](O)CN2C(=O)OC(C)(C)C)s1]

Compound 96A was prepared from (2S,4S)-1-tert-butyl 2-methyl 4-hydroxypyrrolidine-1,2-dicarboxylate and 5-methylthiazol-2-amine as described for 65A. LC/MS [M+H]⁺: 515; Ret time (Method F): 1.91 min. LC/MS [M+H-Boc]⁺: 228; Ret time (Method F): 2.52 min.

96B. (2S,4S)-4-Hydroxy-N-(5-methylthiazol-2-yl)pyrrolidine-2-carboxamide

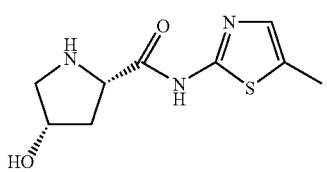

(2S,4S)-4-Hydroxy-N-(5-methylthiazol-2-yl)pyrrolidine-2-carboxamide 65A was prepared from (2S,4S)-1-tert-butyl 2-methyl 4-hydroxypyrrolidine-1,2-dicarboxylate and 5-methylthiazol-2-amine as described for 65B. LC/MS [M+H]⁺: 228; Ret time (Method F): 0.55 min.

96C. (2S,4S)-1-(4-Chloro-6-(5-cyclopropyl-1H-pyrazol-3-ylamino)-1,3,5-triazin-2-yl)-4-hydroxy-N-(5-methylthiazol-2-yl)pyrrolidine-2-carboxamide

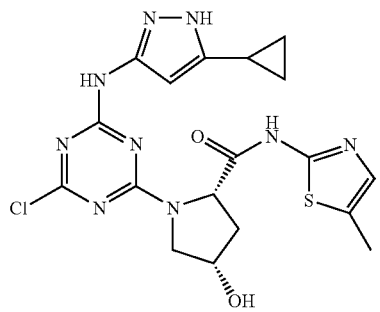 [SMILES: Cc1cnc(NC(=O)[C@@H]2C[C@H](O)CN2c2nc(Cl)nc(Nc3cc(C4CC4)[nH]n3)n2)s1]

96C was prepared from 1A and 96B as described for 1C. LC/MS [M+H]⁺: 462; Ret time (Method F): 2.53 min.

Compound 96 was prepared from morpholine and 96C as described for 1: LC/MS [M+H]⁺: 513, Ret time (Method F): 2.51 min.

Examples 97 to 99

Examples 97 to 99 are disclosed in Table 7 and were prepared using procedures described above in Example 96.

TABLE 7

| Example No. | Compound | HPLC ret. time (min.) | [M + H]+ |
|---|---|---|---|
| 97 | 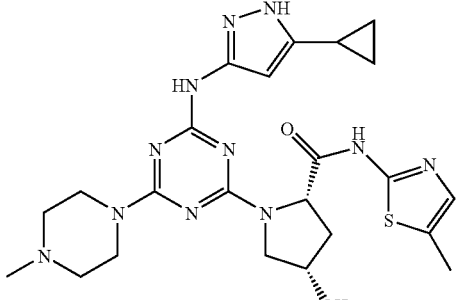<br>(2S,4S)-1-(4-(5-Cyclopropyl-1H-pyrazol-3-ylamino)-6-(4-methylpiperazin-1-yl)-1,3,5-triazin-2-yl)-4-hydroxy-N-(5-methylthiazol-2-yl)pyrrolidine-2-carboxamide | 1.91 (f) | 526 |
| 98 | 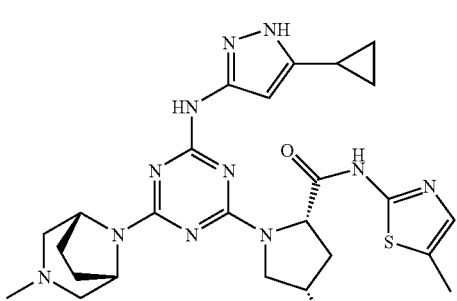<br>(2S,4S)-1-(4-(5-Cyclopropyl-1H-pyrazol-3-ylamino)-6-((1R,5S)-3-methyl-3,8-diazabicyclo[3.2.1]octan-8-yl)-1,3,5-triazin-2-yl)-4-hydroxy-N-(5-methylthiazol-2-yl)pyrrolidine-2-carboxamide | 2.06 (f) | 552 |
| 99 | 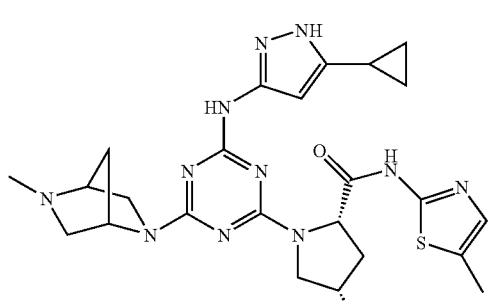<br>(2S,4S)-1-(4-(5-Cyclopropyl-1H-pyrazol-3-ylamino)-6-(5-methyl-2,5-diazabicyclo[2.2.1]heptan-2-yl)-1,3,5-triazin-2-yl)-4-hydroxy-N-(5-methylthiazol-2-yl)pyrrolidine-2-carboxamide | 1.92 (f) | 538 |

Example 100

(2S,4S)-1-(4-(5-Cyclopropyl-1H-pyrazol-3-ylamino)-6-morpholino-1,3,5-triazin-2-yl)-N-(5-fluorothiazol-2-yl)-4-hydroxypyrrolidine-2-carboxamide

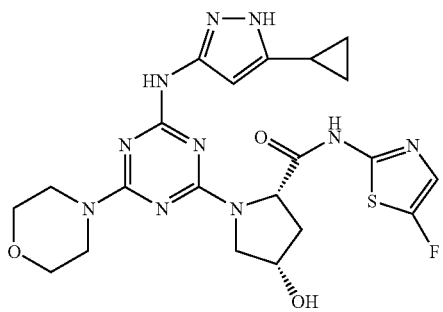 [SMILES: O=C(Nc1ncc(F)s1)[C@@H]1C[C@H](O)CN1c1nc(Nc2cc(C3CC3)[nH]n2)nc(N2CCOCC2)n1]

100A. (2S,4S)-tent-Butyl 2-(5-fluorothiazol-2-ylcarbamoyl)-4-hydroxy pyrrolidine-1-carboxylate

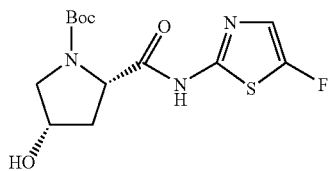 [SMILES: CC(C)(C)OC(=O)N1C[C@@H](O)C[C@H]1C(=O)Nc1ncc(F)s1]

To a solution of 5-fluorothiazol-2-amine, 1.3 TFA (2.249 g, 8.44 mmol) in THF (30 mL) was added isopropylmagnesium (8 mL, 16.00 mmol) (2.0 M THF solution) at 0° C. under nitrogen. The reaction mixture was stirred at RT for 5 min. (1S,4S)-tert-butyl 3-oxo-2-oxa-5-azabicyclo[2.2.1]heptane-5-carboxylate (1.5 g, 7.03 mmol) solid was added to the reaction mixture. The reaction mixture was stirred at RT for 16 h, quenched with MeOH, and concentrated. To the residue were added NH₄Cl (sat'd) and EtOAc. The organic layers were washed with brine, dried over Na₂SO₄, and filtered. The crude product was purified by Biotage (25-60% EtOAc/hex, 1.7 L, 60-80% EtOAc/hex 1.0 L). 1.42 g (60.9%) product was isolated as an oil. LC/MS [M+H-Boc]⁺: 232; Ret time (Method F): 2.70 min.

100B. (2S,4S)—N-(5-Fluorothiazol-2-yl)-4-hydroxypyrrolidine-2-carboxamide

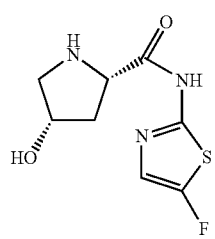 [SMILES: O=C(Nc1ncc(F)s1)[C@@H]1C[C@H](O)CN1]

To a solution of (2S,4S)-tert-butyl 2-(5-fluorothiazol-2-ylcarbamoyl)-4-hydroxypyrrolidine-1-carboxylate (1.42 g, 4.29 mmol) in MeOH (40 mL) was added 4N HCl in dioxane (10.71 mL, 42.9 mmol). The reaction mixture was stirred at RT for 2 h and concentrated. The residue was used for the next step without purification. LC/MS [M+H]⁺: 232; Ret time (Method F): 0.51 min.

100C. (2S,4S)-1-(4-Chloro-6-(5-cyclopropyl-1H-pyrazol-3-ylamino)-1,3,5-triazin-2-yl)-N-(5-fluorothiazol-2-yl)-4-hydroxypyrrolidine-2-carboxamide

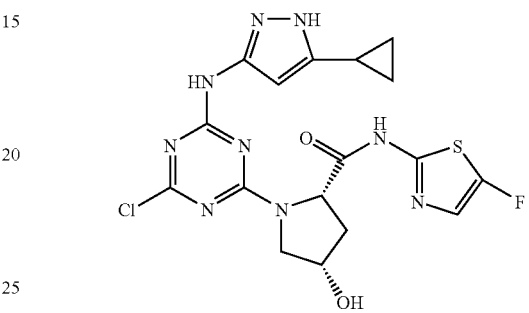

To a solution of 4,6-dichloro-N-(5-cyclopropyl-1H-pyrazol-3-yl)-1,3,5-triazin-2-amine (11.62 mL, 1.359 mmol) in THF was added solid (2S,4S)-tert-butyl 2-(5-fluorothiazol-2-ylcarbamoyl)-4-hydroxypyrrolidine-1-carboxylate HCl salt (0.5 g, 1.359 mmol) and Hunig's base (0.712 mL, 4.08 mmol). The reaction mixture was stirred at RT for 2 h. The crude reaction solution was used for the next step without purification. LC/MS [M+H]⁺: 466; Ret time (Method F): 2.68 min.

To the reaction mixture was added morpholine (0.355 g, 4.08 mmol). The reaction mixture was stirred at RT for 4 h and concentrated. The residue was purified by prep. HPLC. The HPLC fractions that contained the product were concentrated with speedvac and applied on to a cartridge of MCX. This was washed with methanol and the product was eluted with 2N solution of ammonia in methanol to give 100 (320 mg, 44%). LC/MS [M+H]⁺: 517; Ret time (Method F): 2.67 min.

Example 101

(2S,4S)-1-(4-(5-Cyclopropyl-1H-pyrazol-3-ylamino)-6-morpholino-1,3,5-triazin-2-yl)-4-hydroxy-2-methyl-N-(thiazol-2-yl)pyrrolidine-2-carboxamide

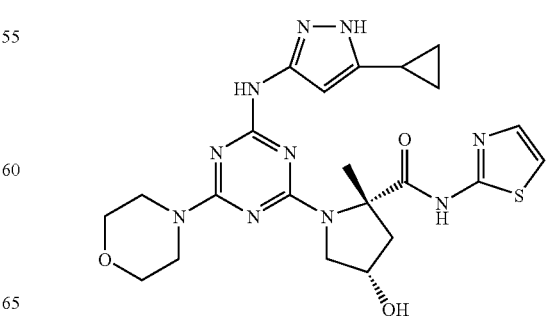

101A. (2S,4S)-2-Benzyl 1-tent-butyl 4-hydroxy-2-methylpyrrolidine-1,2-dicarboxylate

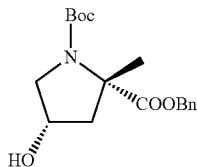

101A was prepared from commercially available (S)-benzyl 2-aminopropanoate and (R)-2-(chloromethyl)oxirane according to the procedures described in *Org. Lett.*, 3029 (2007).

101B. (2S,4S)-1-(tert-Butoxycarbonyl)-4-hydroxy-2-methylpyrrolidine-2-carboxylic acid

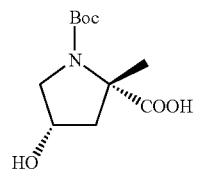 [SMILES: CC(C)(C)OC(=O)N1C[C@@H](O)C[C@@]1(C)C(=O)O]

To nitrogen flushed pressure bottle, were added Pd/C (200 mg) and (2S,4S)-2-benzyl 1-tert-butyl 4-hydroxy-2-methylpyrrolidine-1,2-dicarboxylate (1.4 g, 4.17 mmol) in MeOH (300 mL). The reaction mixture was hydrogenated at 50 psi overnight. The reaction mixture was passed through a pad of celite, washed with MeOH, and concentrated. The residue (0.86 g, 84%) was used for the next step without purification. $^1$H NMR (CD$_3$OD, 400 MHz) δ 4.32-4.39 (m, 1H), 3.62-3.68 (m, 1H), 3.34-3.37 (m, 1H), 2.12-2.22 (m, 2H), 1.51 and 1.49 (s, 3H), 1.43 and 1.40 (s, 9H).

101C. (1S,4S)-tert-Butyl 4-methyl-3-oxo-2-oxa-5-azabicyclo[2.2.1]heptane-5-carboxylate

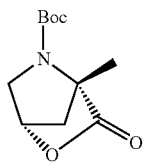 [SMILES: CC(C)(C)OC(=O)N1C[C@@H]2C[C@@]1(C)C(=O)O2]

To a solution of (2S,4S)-1-(tert-butoxycarbonyl)-4-hydroxy-2-methylpyrrolidine-2-carboxylic acid (860 mg, 3.51 mmol) and diphenyl phosphorazidate (700 mg, 2.54 mmol) (DPPA) was added Et$_3$N (0.680 mL, 4.88 mmol) at 0° C. The reaction mixture was stirred at RT for 6 h, quenched with water, extracted with EtOAc (3×40 ml). The combined organic layers were washed with water and brine, dried over Na$_2$SO$_4$, filtered, and concentrated. The residue was purified by Biotage (0-30% EtOAc/hex, 1.2 L) to give 101C (235 mg, 49%). $^1$H NMR (CDCl$_3$, 400 MHz) δ 4.87 (1H, d, J=1.01 Hz), 3.53-3.62 (m, 1H), 3.44-3.53 (m, 1H), 1.98-2.10 (m, 2H), 1.74 (s, 3H), 1.40 (s, 9H); $^{13}$C NMR (CDCl$_3$, 101 MHz) δ 172.45 (1C), 154.93 (1C), 81.22 (1C), 75.03 (1C), 64.02 (1C), 53.16 (1C), 46.35 (1C), 28.26 (1C), and 13.96 (3C).

101D. (2S,4S)-tent-Butyl 4-hydroxy-2-methyl-2-(thiazol-2-ylcarbamoyl) pyrrolidine-1-carboxylate

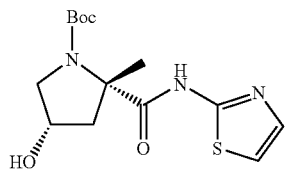 [SMILES: CC(C)(C)OC(=O)N1C[C@@H](O)C[C@@]1(C)C(=O)Nc1nccs1]

To a solution of thiazol-2-amine (2.327 g, 23.23 mmol) in THF (15 mL) was added isopropylmagnesium chloride (11.3 mL, 22.60 mmol) at 0° C. under nitrogen. The reaction mixture was stirred at RT for 30 min. A solution of (1S,4S)-tert-butyl 4-methyl-3-oxo-2-oxa-5-azabicyclo[2.2.1]heptane-5-carboxylate (0.66 g, 2.90 mmol) in THF (3 ml) was added to the reaction mixture. The reaction mixture was stirred at RT for 1 h and heated to 60° C. for 4 h. The reaction mixture was stirred at RT overnight and concentrated. The residue was quenched with TFA in MeOH. The crude product was purified by prep.HPLC. to give 101D (0.49 g, 38%) as a TFA salt. LC/MS [M+H]$^+$: 328; Ret time (Method F): 2.58 min.

101E. (2S,4S)-4-Hydroxy-2-methyl-N-(thiazol-2-yl)pyrrolidine-2-carboxamide

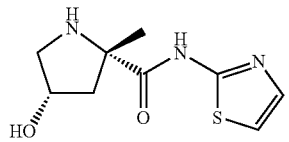

To a solution of (2S,4S)-tert-butyl 4-hydroxy-2-methyl-2-(thiazol-2-ylcarbamoyl)pyrrolidine-1-carboxylate (0.49 g, 1.5 mmol) in CH$_2$Cl$_2$ was added TFA (1 ml, excess). The reaction mixture was stirred at RT for 14 h and concentrated. The residue was used for the next step without purification. LC/MS [M+H]$^+$: 228; Ret time (Method F): 0.46 min.

101F. (2S,4S)-1-(4-Chloro-6-(5-cyclopropyl-1H-pyrazol-3-ylamino)-1,3,5-triazin-2-yl)-4-hydroxy-2-methyl-N-(thiazol-2-yl)pyrrolidine-2-carboxamide

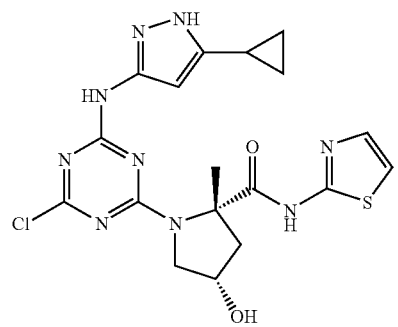 [SMILES: C[C@@]1(C(=O)Nc2nccs2)C[C@H](O)CN1c1nc(Cl)nc(Nc2cc(C3CC3)[nH]n2)n1]

To a solution of 1A (400 mg, 1.5 mmol) in THF (15 ml) were added a solution of (2S,4S)-4-hydroxy-2-methyl-N-(thiazol-2-yl)pyrrolidine-2-carboxamide (342 mg, 1.5 mmol)

and Hunig's base (455 mg, 4.5 mmol). The reaction mixture was stirred at RT for 4 h. The crude reaction solution was used for the next step without purification. LC/MS [M+H]⁺: 462; Ret time (Method F): 2.65 min.

To a solution of (2S,4S)-1-(4-chloro-6-(5-cyclopropyl-1H-pyrazol-3-ylamino)-1,3,5-triazin-2-yl)-4-hydroxy-2-methyl-N-(thiazol-2-yl)pyrrolidine-2-carboxamide (50 mg, 0.108 mmol) in THF was added morpholine (0.1 ml, excess). The reaction mixture was stirred at RT for 4 h and concentrated. The residue was purified by prep. HPLC. The HPLC fractions that contained the product were concentrated with speedvac and applied on to a cartridge of MCX. This was washed with methanol and the product was eluted with 2N solution of ammonia in methanol to give 101 (23 mg, 42%). LC/MS [M+H]⁺: 513; Ret time (Method F): 2.56 min.

Examples 102 to 104

Examples 102 to 104 are disclosed in Table 8 and were prepared using procedures described above in Example 101.

TABLE 8

| Example No. | Compound | HPLC ret. Time (min.) | [M + H]⁺ |
|---|---|---|---|
| 102 | 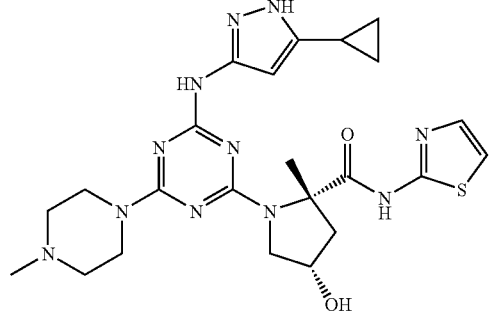 [SMILES: CN1CCN(c2nc(Nc3cc(C4CC4)[nH]n3)nc(N3C[C@@H](O)C[C@@]3(C)C(=O)Nc3nccs3)n2)CC1]<br>(2S,4S)-1-(4-(5-Cyclopropyl-1H-pyrazol-3-ylamino)-6-(4-methylpiperazin-1-yl)-1,3,5-triazin-2-yl)-4-hydroxy-2-methyl-N-(thiazol-2-yl)pyrrolidine-2-carboxamide | 2.01 (f) | 526 |
| 103 | 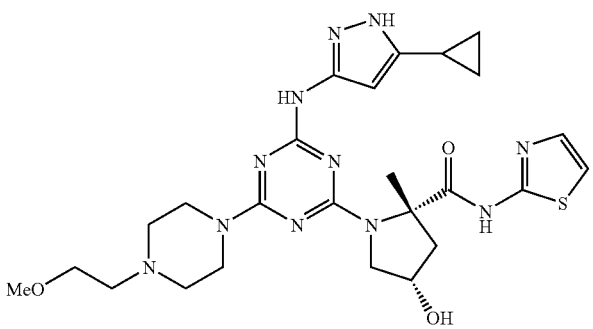 [SMILES: COCCN1CCN(c2nc(Nc3cc(C4CC4)[nH]n3)nc(N3C[C@@H](O)C[C@@]3(C)C(=O)Nc3nccs3)n2)CC1]<br>(2S,4S)-1-(4-(5-Cyclopropyl-1H-pyrazol-3-ylamino)-6-(4-(2-methoxyethyl)piperazin-1-yl)-1,3,5-triazin-2-yl)-4-hydroxy-2-methyl-N-(thiazol-2-yl)pyrrolidine-2-carboxamide | 1.99 (f) | 570 |
| 104 | 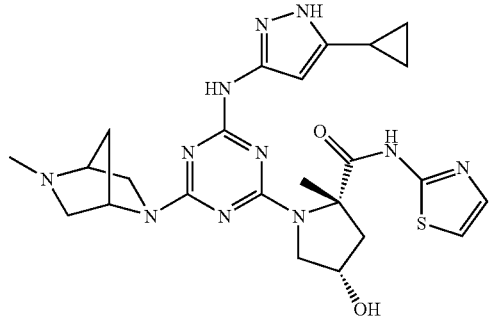 [SMILES: CN1CC2CC1CN2c1nc(Nc2cc(C3CC3)[nH]n2)nc(N2C[C@@H](O)C[C@@]2(C)C(=O)Nc2nccs2)n1]<br>(2S,4S)-1-(4-(5-Cyclopropyl-1H-pyrazol-3-ylamino)-6-(5-methyl-2,5-diazabicyclo[2.2.1]heptan-2-yl)-1,3,5-triazin-2-yl)-4-hydroxy-2-methyl-N-(thiazol-2-yl)pyrrolidine-2-carboxamide | 1.94 (f) | 538 |

Example 105

(2S,4S)-1-(4-(5-Cyclopropyl-1H-pyrazol-3-ylamino)-6-morpholino-1,3,5-triazin-2-yl)-4-hydroxy-2-methyl-N-(5-methylthiazol-2-yl)pyrrolidine-2-carboxamide

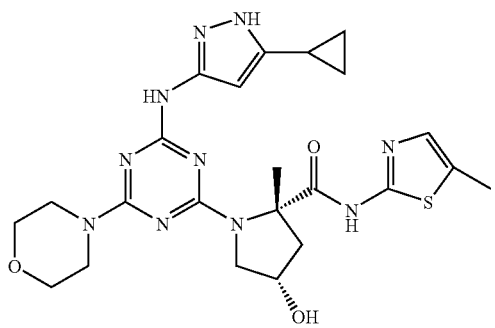 [SMILES: Cc1cnc(NC(=O)[C@]2(C)C[C@H](O)CN2c2nc(Nc3cc(C4CC4)[nH]n3)nc(N3CCOCC3)n2)s1]

105A. (1S,4S)-5-(4-Chloro-6-(3-cyclopropyl-1H-pyrazol-5-ylamino)-1,3,5-triazin-2-yl)-4-methyl-2-oxa-5-azabicyclo[2.2.1]heptan-3-one

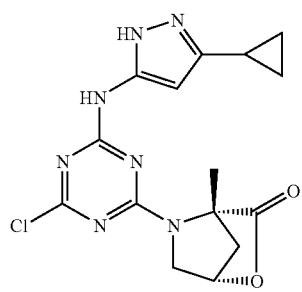 [SMILES: C[C@@]12C[C@@H](CN1c1nc(Cl)nc(Nc3cc(C4CC4)n[nH]3)n1)OC2=O]

To a solution of (1S,4S)-tert-butyl 4-methyl-3-oxo-2-oxa-5-azabicyclo[2.2.1]heptane-5-carboxylate (230 mg, 1.01 mmol) in CH$_2$Cl$_2$ (20 ml) was added TFA (0.5 ml, excess). The reaction mixture was stirred at RT for 6 h and concentrated. The residue was used for the next step without purification.

The crude product obtained above was added to a solution of 1A (270 mg, 1.01 mmol) and Hunig's base (300 mg, 3.03 mmol) in THF (10 ml). The reaction mixture was stirred at RT for 6 h. The crude product was used for the next step without purification. LC/MS [M+H]$^+$: 362; Ret time (Method F): 2.56 min.

105B. (1S,4S)-5-(4-(3-Cyclopropyl-1H-pyrazol-5-ylamino)-6-morpholino-1,3,5-triazin-2-yl)-4-methyl-2-oxa-5-azabicyclo[2.2.1]heptan-3-one

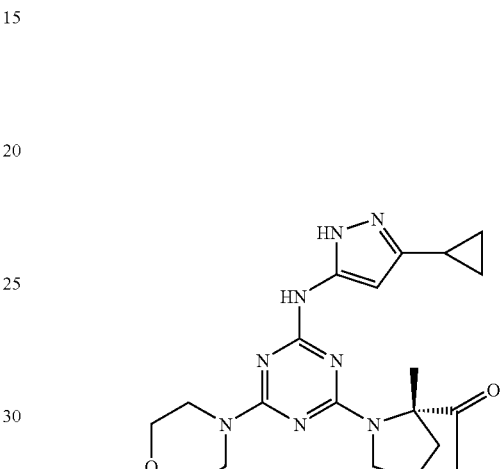

To a solution of (1S,4S)-5-(4-chloro-6-(3-cyclopropyl-1H-pyrazol-5-ylamino)-1,3,5-triazin-2-yl)-4-methyl-2-oxa-5-azabicyclo[2.2.1]heptan-3-one (365 mg, 1.01 mmol) in THF (10 ml) was added morpholine (0.2 ml, excess). The reaction mixture was stirred at RT for 4 h and concentrated. The residue was purified by prep. HPLC to give 105B (340 mg, 66%) as a TFA salt. LC/MS [M+H]$^+$: 513; Ret time (Method F): 2.56 min.

To a solution of aminothiazole (200 mg) in THF (10 ml) was added isopropylmagnesium chloride (2.0M THF solution) (0.95 ml. 0.95 mmol) at 0° C. under nitrogen. The reaction mixture was stirred at RT for 30 min. A solution of (1S,4S)-5-(4-(3-cyclopropyl-1H-pyrazol-5-ylamino)-6-morpholino-1,3,5-triazin-2-yl)-4-methyl-2-oxa-5-azabicyclo[2.2.1]heptan-3-one (50 mg, 0.10 mmol) in THF (3 mL) was added. The reaction mixture was heated to 60° C. for 6 h and cooled to RT. The crude product was purified by prep. HPLC. The HPLC fractions that contained the product were concentrated with speedvac and applied on to a cartridge of MCX. This was washed with methanol and the product was eluted with 2N solution of ammonia in methanol to give 105 (21 mg, 40%). LC/MS [M+H]$^+$: 527; Ret time (Method F): 2.66 min.

Example 106

(S)-1-(4-(5-Cyclopropyl-1H-pyrazol-3-ylamino)-6-morpholino-1,3,5-triazin-2-yl)-2,4,4-trimethyl-N-(pyrazin-2-yl)pyrrolidine-2-carboxamide

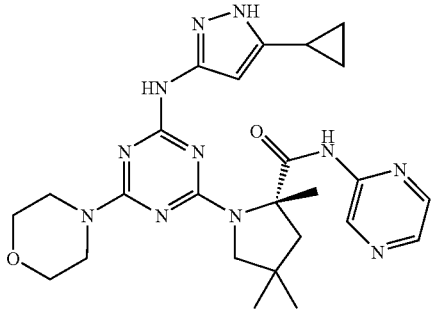 [SMILES: CC1(C)CN(c2nc(Nc3cc(C4CC4)[nH]n3)nc(N3CCOCC3)n2)[C@](C)(C(=O)Nc2cnccn2)C1]

(S)-1-(tert-Butoxycarbonyl)-2-methylpyrrolidine-2-carboxylic acid

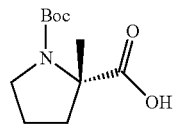 [SMILES: CC(C)(C)OC(=O)N1CCC[C@@]1(C)C(=O)O]

To a stirred solution of commercially available (S)-2-methylpyrrolidine-2-carboxylic acid (20 g, 0.155 mol) and di-tert-butyl dicarbonate (40.6 g, 0.186 mol) in methylene chloride (200 ml) was added triethylamine (24.5 g, 0.233 mol). The suspension was stirred at room temperature overnight. The reaction mixture was concentrated and purified by flash chromatography (2-5% MeOH/CH$_2$Cl$_2$) to give (S)-1-(tert-butoxycarbonyl)-2-methylpyrrolidine-2-carboxylic acid 106A as an oil.

106B. (S)-1-tert-Butyl 2-methyl 2-methylpyrrolidine-1,2-dicarboxylate

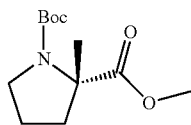 [SMILES: COC(=O)[C@]1(C)CCCN1C(=O)OC(C)(C)C]

To a stirred solution of (S)-1-(tert-butoxycarbonyl)-2-methylpyrrolidine-2-carboxylic acid 106A in methanol (100 ml) and ether (100 ml) was added TMS-Diazomethane (80 ml) (2.0 M ether solution) dropwise at 0° C. The reaction mixture was stirred at room temperature for 2 h and the reaction mixture was concentrated. The residue was purified by flash chromatography (10% EtOAc/Hexane) to give (S)-1-tent-butyl 2-methyl 2-methylpyrrolidine-1,2-dicarboxylate 106B (28.5 g, 76% overall yield) as an oil. $^1$H NMR (CDCl$_3$, 400 MHz) δ 3.69 (s, 3H), 3.42-3.56 (m, 2H), 2.13-2.17 (m, 1H), 1.83-1.93 (m, 3H), 1.49 (s, 3H), 1.39 (s, 9H).

106C. (S)-1-tert-Butyl 2-methyl 2-methyl-5-oxopyrrolidine-1,2-dicarboxylate

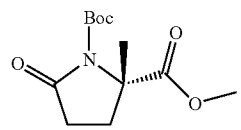 [SMILES: COC(=O)[C@]1(C)CCC(=O)N1C(=O)OC(C)(C)C]

To a vigorously stirred solution of (S)-1-tert-butyl 2-methyl 2-methylpyrrolidine-1,2-dicarboxylate 106B (1 g, 4.11 mmol) in ethyl acetate (40 ml) was added a solution of NaIO$_4$ (3.52 g, 16.46 mmol) and RuCl$_3$ (10 mg, 0.04 mmol) in water (40 ml). The reaction mixture was stirred at room temperature overnight and quenched with isopropanol. The reaction mixture was stirred at room temperature for 20 min and concentrated. The residue was dissolved in ethyl acetate, washed with water and brine, and dried over Na$_2$SO$_4$. The crude product was purified by flash chromatography (20-50% EtOAc/hexane) to give (S)-1-tert-butyl 2-methyl 2-methyl-5-oxopyrrolidine-1,2-dicarboxylate 106C (1.02 g, 100%) as an oil. $^1$H NMR (CDCl$_3$, 400 MHz) δ 3.74 (s, 3H), 2.51-2.64 (m, 2H), 2.16-2.21 (m, 1H), 1.97-2.02 (m, 3H), 1.65 (s, 3H), 1.46 (s, 9H).

106D. (S)-Methyl 2,4,4-trimethylpyrrolidine-2-carboxylate

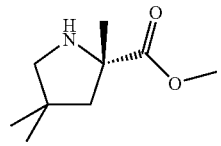

To a stirred solution of (S)-1-tert-butyl 2-methyl 2,4,4-trimethyl-5-oxopyrrolidine-1,2-dicarboxylate 106C (13.96 g, 48.9 mmol) in THF (100 mL) was added Super-hydride (lithium triethylboro-hydride) (58.7 mL, 58.7 mmol) at −78° C. under nitrogen atmosphere. The reaction mixture was stirred at −78° C. for 2 h and quenched with saturated NaHCO$_3$ at −78° C. The reaction mixture was warmed to 0° C. and hydrogen peroxide (15 ml) was added drop-wise at 0° C. The mixture was stirred at 0° C. for 30 min and extracted with ethyl acetate. The combined organic layers were washed with water and brine, dried over Na$_2$SO$_4$. After concentration, the crude product was used for the next step without purification. To a stirred solution of the crude product obtained above in CH$_2$Cl$_2$, was added half of triethylsilane (17.19 mL., 108 mmol) and half of BF$_3$.OEt$_2$ (13.64 mL., 108 mmol) at −78° C. under nitrogen atmosphere. The reaction mixture was stirred at −78° C. for 1 h, then the remaining triethylsilane (17.19 mL., 108 mmol) and BF$_3$.OEt$_2$ (13.64 mL, 108 mmol) were added. The reaction mixture was stirred at −78° C. for 2 h and quenched with saturated NaHCO$_3$ solution. The reaction mixture was extracted with CH₂Cl₂. The combined organic layers were washed with water and brine, dried over Na₂SO₄. The crude product was purified by Biotage (0-30% EtOAc/Hexane, 1.5 L) to give (S)-1-tert-butyl 2-methyl 2,4,4-trimethylpyrrolidine-1,2-dicarboxylate 106D (10 g, 75%) as an oil.

To a stirred solution of (S)-1-tert-butyl 2-methyl 2,4,4-trimethylpyrrolidine-1,2-dicarboxylate 106D in CH₂Cl₂ (60 ml) was added TFA (10 mL). The reaction mixture was stirred at room temperature overnight and concentrated. The residue was used for the next step without purification.

106E. (S)-Methyl 1-(4-chloro-6-(5-cyclopropyl-1H-pyrazol-3-ylamino)-1,3,5-triazin-2-yl)-2,4,4-trimethylpyrrolidine-2-carboxylate

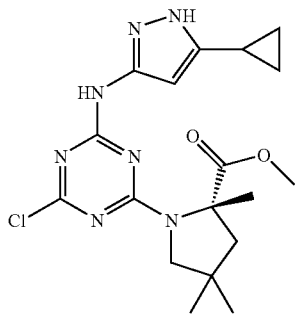 [SMILES: COC(=O)[C@]1(C)CC(C)(C)CN1c1nc(Cl)nc(Nc2cc(C3CC3)[nH]n2)n1]

Compound 106E was prepared from 1A and 106D as described for 1C: LC/MS [M+H]⁺: 406/408; Ret time (Method F): 3.55 min.

106F. (S)-Methyl 1-(4-(5-cyclopropyl-1H-pyrazol-3-ylamino)-6-morpholino-1,3,5-triazin-2-yl)-2,4,4-trimethylpyrrolidine-2-carboxylate

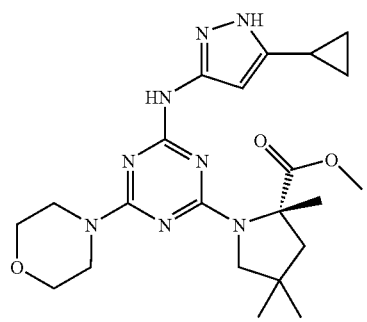 [SMILES: COC(=O)[C@]1(C)CC(C)(C)CN1c1nc(Nc2cc(C3CC3)[nH]n2)nc(N2CCOCC2)n1]

Compound 106F was prepared from morpholine and 106E as described for 1: LC/MS [M+H]⁺: 457; Ret time (Method F): 2.97 min.

To a solution of pyrazin-2-amine (200 mg, 2.10 mmol) in THF (5 mL) was added isopropylmagnesium chloride (1.0 mL, 1.99 mmol) (2.0 M THF solution) at 0° C. under nitrogen. The resulting suspension was stirred at RT for 30 min. A solution of (S)-methyl 1-(4-(3-cyclopropyl-1H-pyrazol-5-ylamino)-6-morpholinopyrimidin-2-yl)-2,4,4-trimethylpyrrolidine-2-carboxylate (50 mg, 0.10 mmol) was added to the suspension. The reaction mixture was stirred at RT for 4 h, quenched with MeOH, and concentrated. The residue was separated by preparative HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 106. LC/MS [M+H]⁺: 520; Ret time (Method F): 2.85 min.

Example 107

(S)-1-(4-(5-Cyclopropyl-1H-pyrazol-3-ylamino)-6-(4-methylpiperazin-1-yl)-1,3,5-triazin-2-yl)-2,4,4-trimethyl-N-(pyrazin-2-yl)pyrrolidine-2-carboxamide

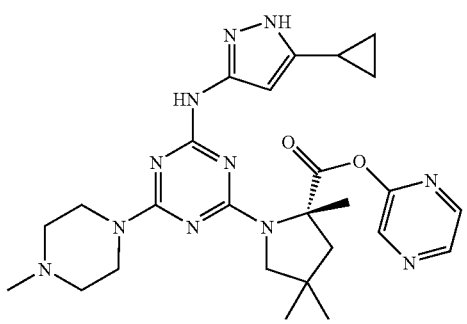 [SMILES: CN1CCN(c2nc(Nc3cc(C4CC4)[nH]n3)nc(N3CC(C)(C)C[C@@]3(C)C(=O)Oc3cnccn3)n2)CC1]

Compound 107 was prepared from N-methyl piperazine and 106E as described for 106F and 106. LC/MS [M+H]⁺: 520; Ret time (Method F): 2.85 min.

Example 108

(S)-1-(4-(5-Cyclopropyl-1H-pyrazol-3-ylamino)-6-morpholino-1,3,5-triazin-2-yl)-2,4,4-trimethyl-N-(thiazol-2-yl)pyrrolidine-2-carboxamide

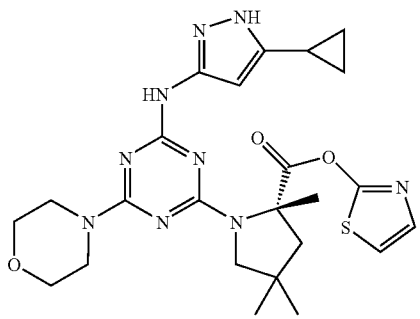 [SMILES: CC1(C)CN(c2nc(Nc3cc(C4CC4)[nH]n3)nc(N3CCOCC3)n2)[C@](C)(C(=O)Oc2nccs2)C1]

Compound 108 was prepared from 106F and 2-amino thaizole as described for 106. LC/MS [M+H]+: 525; Ret time (Method F): 2.99 min.

Example 109

(S)-1-(4-(5-Cyclopropyl-1H-pyrazol-3-ylamino)-6-morpholino-1,3,5-triazin-2-yl)-N-(thiazol-2-yl)pyrrolidine-2-carboxamide

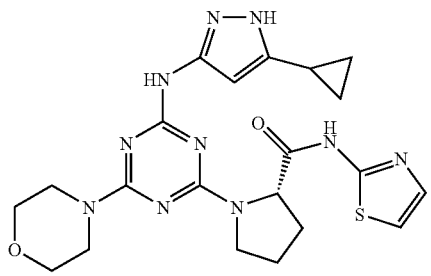 [SMILES: O=C(Nc1nccs1)[C@@H]1CCCN1c1nc(Nc2cc(C3CC3)[nH]n2)nc(N2CCOCC2)n1]

109A. (S)—N-(Thiazol-2-yl)pyrrolidine-2-carboxamide

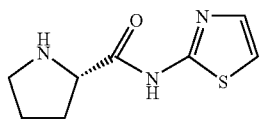 [SMILES: O=C(Nc1nccs1)[C@@H]1CCCN1]

(S)—N-(thiazol-2-yl)pyrrolidine-2-carboxamide 109A was prepared from commercially available tert-butyl 2-methylpyrrolidine-1,2-dicarboxylateas described for 65A. LC/MS [M+H]+: 198; Ret time (Method F): 0.74 min.

109B. (S)-1-(4-Chloro-6-(3-cyclopropyl-1H-pyrazol-5-ylamino)-1,3,5-triazin-2-yl)-N-(thiazol-2-yl)pyrrolidine-2-carboxamide

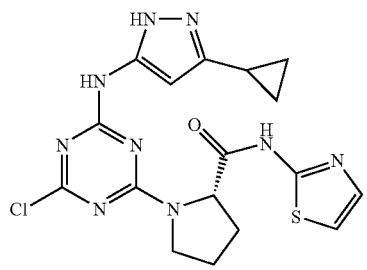 [SMILES: O=C(Nc1nccs1)[C@@H]1CCCN1c1nc(Cl)nc(Nc2cc(C3CC3)n[nH]2)n1]

(S)-1-(4-Chloro-6-(3-cyclopropyl-1H-pyrazol-5-ylamino)-1,3,5-triazin-2-yl)-N-(thiazol-2-yl)pyrrolidine-2-carboxamide 109B was prepared from 1A and 109A as described for 1C. LC/MS [M+H]+: 432/434; Ret time (Method F): 2.70 min.

Compound 109 was prepared from morpholine and 109B as described for 1. LC/MS [M+H]+: 483; Ret time (Method F): 2.54 min.

Example 110

(S)-1-(4-(5-Cyclopropyl-1H-pyrazol-3-ylamino)-6-(4-methylpiperazin-1-yl)-1,3,5-triazin-2-yl)-N-(thiazol-2-yl)pyrrolidine-2-carboxamide

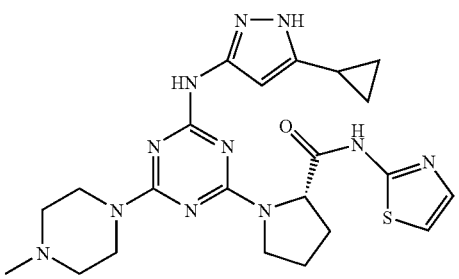 [SMILES: CN1CCN(c2nc(Nc3cc(C4CC4)[nH]n3)nc(N3CCC[C@H]3C(=O)Nc3nccs3)n2)CC1]

Compound 110 was prepared from 1-methylpiperazine and 109B as described for 1. LC/MS [M+H]+: 496; Ret time (Method F): 2.02 min.

Example 111

(S)-1-(4-(5-Cyclopropyl-1H-pyrazol-3-ylamino)-6-(4-(2-methoxyethyl)piperazin-1-yl)-1,3,5-triazin-2-yl)-N-(thiazol-2-yl)pyrrolidine-2-carboxamide

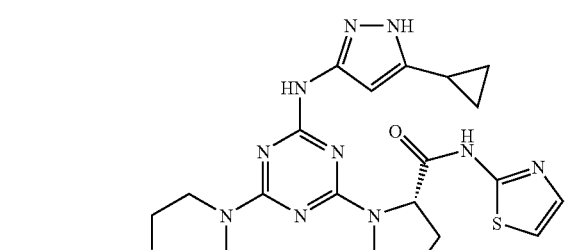

Compound 111 was prepared from 1-(2-methoxyethyl)piperazine and 109B as described for 1. LC/MS [M+H]+: 540; Ret time (Method F): 2.07 min.

Example 112

(2S,4S)-1-(4-(5-Cyclopropyl-1H-pyrazol-3-ylamino)-6-morpholino-1,3,5-triazin-2-yl)-4-methoxy-N—((R)-piperidin-3-yl)pyrrolidine-2-carboxamide

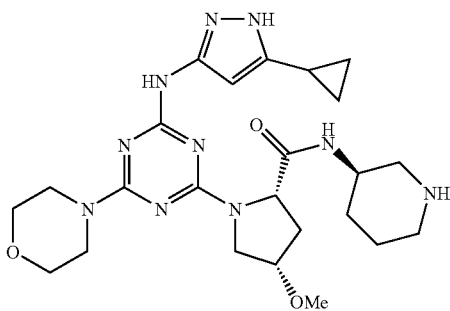 [SMILES: CO[C@H]1C[C@@H](C(=O)N[C@@H]2CCCNC2)N(c2nc(Nc3cc(C4CC4)[nH]n3)nc(N3CCOCC3)n2)C1]

112A. 4-Chloro-N-(5-cyclopropyl-1H-pyrazol-3-yl)-6-morpholino-1,3,5-triazin-2-amine

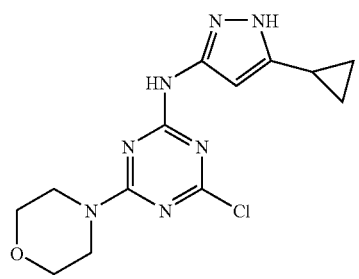 [SMILES: Clc1nc(Nc2cc(C3CC3)[nH]n2)nc(N2CCOCC2)n1]

Compound 112A was prepared from 1A and morpholine as described for 1C. LC/MS [M+H]$^+$: 322/324; Ret time (Method F): 2.81 min.

112B. (2S,4S)-1-(4-(5-Cyclopropyl-1H-pyrazol-3-ylamino)-6-morpholino-1,3,5-triazin-2-yl)-4-methoxypyrrolidine-2-carboxylic acid

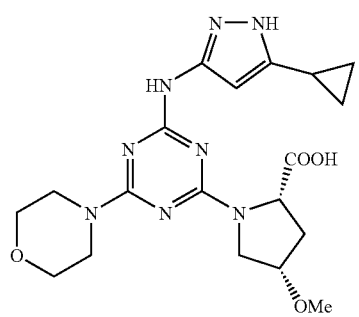 [SMILES: CO[C@H]1C[C@@H](C(=O)O)N(c2nc(Nc3cc(C4CC4)[nH]n3)nc(N3CCOCC3)n2)C1]

Compound 112B was prepared from 112A and (2S,4S)-4-methoxypyrrolidine-2-carboxylic acid as described for 1. LC/MS [M+H]$^+$: 431; Ret time (Method F): 2.27 min.

112C. (R)-tert-Butyl 3-((2S,4S)-1-(4-(5-cyclopropyl-1H-pyrazol-3-ylamino)-6-morpholino-1,3,5-triazin-2-yl)-4-methoxypyrrolidine-2-carboxamido)piperidine-1-carboxylate

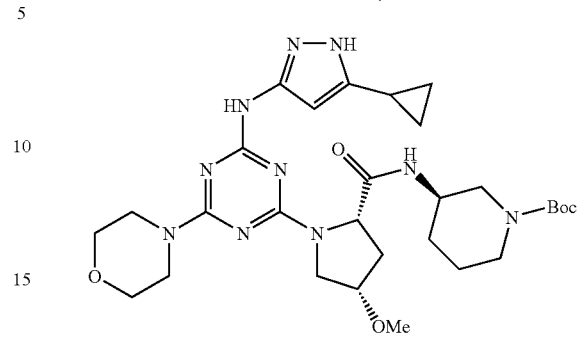

To a solution of 112B (900 mg, 1.653 mmol) in DMF (10 ml) was added N1-((ethylimino)methylene)-N3,N3-dimethylpropane-1,3-diamine hydrochloride (951 mg, 4.96 mmol), (R)-tert-butyl 3-aminopiperidine-1-carboxylate (993 mg, 4.96 mmol), 1H-benzo[d][1,2,3]triazol-1-ol hydrate (253 mg, 1.653 mmol), and Et$_3$N (1.382 ml, 9.92 mmol). The reaction mixture was stirred at RT for 14 h. The crude reaction mixture was purified by prep. HPLC to give 112C (800 mg, 79%). LC/MS [M+H]$^+$: 613; Ret time (Method F): 2.99 min.

To a solution of 112C (900 mg, 1.47 mmol) in CH$_2$Cl$_2$ (40 mL) was added TFA (5 mL, excess). The reaction mixture was stirred at RT for 14 h and concentrated. A small portion was purified by prep. HPLC to provide analytical data and the rest was used in the next step without purification. LC/MS [M+H]$^+$: 513; Ret time (Method F): 1.89 min.

Example 113

(2S,4S)-1-(4-(5-Cyclopropyl-1H-pyrazol-3-ylamino)-6-morpholino-1,3,5-triazin-2-yl)-4-methoxy-N—((R)-1-methylpiperidin-3-yl)pyrrolidine-2-carboxamide

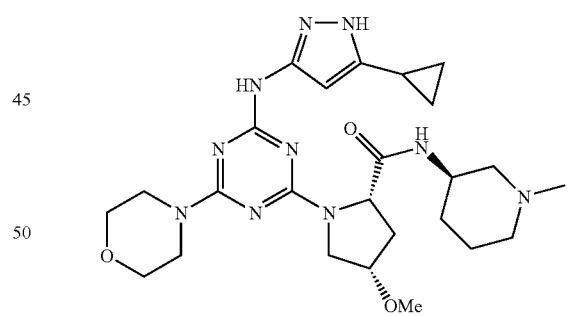

To a solution of 112 (60 mg, 0.117 mmol) in THF (5 mL) was added formaldehyde (0.5 mL, excess), sodium cyanoborohydride (0.24 mL, 0.24 mmol), and Et$_3$N (0.05 mL, 0.35 mmol). The reaction mixture was stirred at RT for 3 h and concentrated. The crude product was purified by prep. HPLC to give 113 (45 mg, 73%). LC/MS [M+H]$^+$: 527; Ret time (Method F): 1.89 min.

Examples 114 and 115

Examples 114 and 115 are disclosed in Table 9 and were prepared using procedures that are described above in Example 113.

TABLE 9

| Example No. | Compound | HPLC ret. t. (min.) | (M + H)+ |
|---|---|---|---|
| 114 | 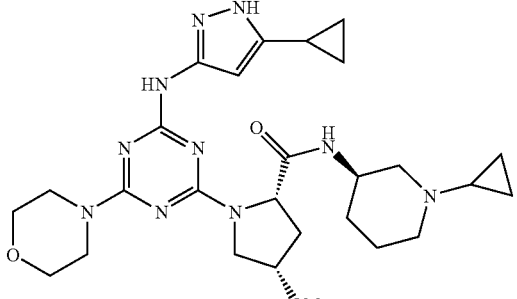<br>(2S,4S)-1-(4-(5-cyclopropyl-1H-pyrazol-3-ylamino)-6-morpholino-1,3,5-triazin-2-yl)-N-((R)-1-cyclopropylpiperidin-3-yl)-4-methoxypyrrolidine-2-carboxamide | 1.91 (f) | 553 |
| 115 | 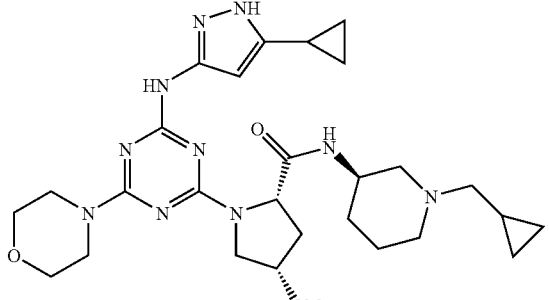<br>(2S,4S)-1-(4-(5-cyclopropyl-1H-pyrazol-3-ylamino)-6-morpholino-1,3,5-triazin-2-yl)-N-((R)-1-(cyclopropylmethyl)piperidin-3-yl)-4-methoxypyrrolidine-2-carboxamide | 1.99 (f) | 567 |

Example 116

(S)-1-(4-(3-Cyclopropyl-1H-pyrazol-5-ylamino)-6-morpholino-1,3,5-triazin-2-yl)-4,4-difluoro-N-(pyrazin-2-yl)pyrrolidine-2-carboxamide

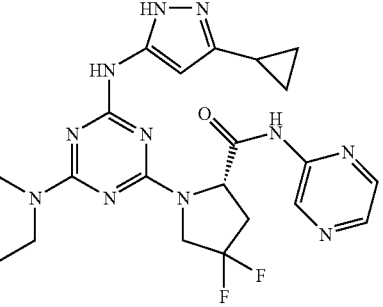

116A. (S)-1-tent-Butyl 2-methyl 4,4-difluoropyrrolidine-1,2-dicarboxylate

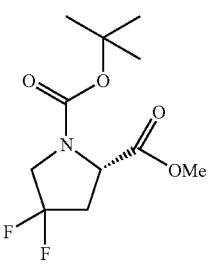 [SMILES: COC(=O)[C@@H]1CC(F)(F)CN1C(=O)OC(C)(C)C]

To a stirred solution of commercially available (S)-1-(tert-butoxycarbonyl)-4,4-difluoropyrrolidine-2-carboxylic acid (5 g, 19.90 mmol) in THF (60 mL) was added trimethylsilyl-diazomethane (12.94 mL, 25.9 mmol) at room temperature.

The mixture was stirred for 12 h and the solvent was evaporated to dryness. The residue was used in the next reaction without further purification.

116B. (S)-tert-Butyl 4,4-difluoro-2-(pyrazin-2-ylcarbamoyl)pyrrolidine-1-carboxylate

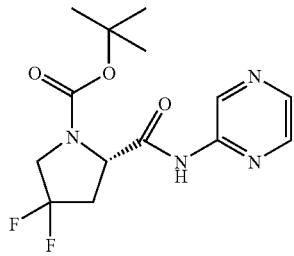

To a stirred solution of pyrazin-2-amine (4.30 g, 45.2 mmol) in 50 mL of THF was added isopropylmagnesium chloride (16.96 mL, 33.9 mmol) dropwise under nitrogen atmosphere. A solid precipitated from the solution. After 15 min, a solution of (S)-1-tert-butyl 2-methyl 4,4-difluoropyrrolidine-1,2-dicarboxylate 116A (3 g, 11.31 mmol) in 50 mL of THF was added and stirred for 2 hr. The solvent was evaporated to dryness at the reduced pressure. The residue was suspended in ethyl acetate, washed with water, brined and dried. Evaporation of the solvent furnished a solid, which was chromatographed (20% ethyl acetate, $CH_2Cl_2$) to give 116B. LC/MS [M+H]$^+$: 329; Ret time (Method F): 2.42 min.

116C. (S)-4,4-Difluoro-N-(pyrazin-2-yl)pyrrolidine-2-carboxamide

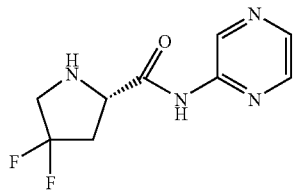

To a stirred solution of (S)-tert-butyl 4,4-difluoro-2-(pyrazin-2-ylcarbamoyl)pyrrolidine-1-carboxylate 116B (1.6 g, 4.87 mmol) in $CH_2Cl_2$ (30 mL) was added trifluoroacetic acid (7.24 mL, 97 mmol). The mixture was stirred for 4 hrs, the solvent was evaporated to dryness and the residue 116C was used in the next reaction without further purification. LC/MS [M+H]$^+$: 229; Ret time (Method F): 0.61 min.

116D. (S)-1-(4-Chloro-6-(3-cyclopropyl-1H-pyrazol-5-ylamino)-1,3,5-triazin-2-yl)-4,4-difluoro-N-(pyrazin-2-yl)pyrrolidine-2-carboxamide

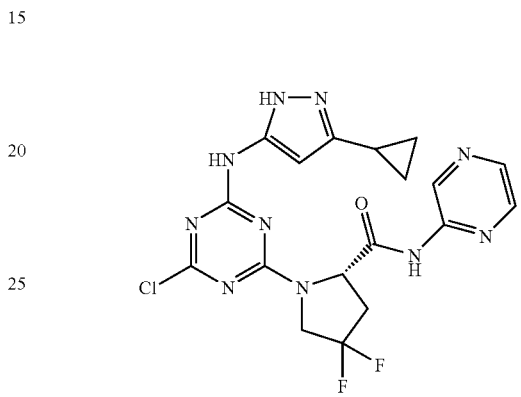

To a stirred solution of 4,6-dichloro-N-(5-cyclopropyl-1H-pyrazol-3-yl)-1,3,5-triazin-2-amine 1A (1.320 g, 4.87 mmol) in MeOH (50 mL) was added N,N-diisopropylethylamine (1.697 mL, 9.74 mmol) followed by (S)-4,4-difluoro-N-(pyrazin-2-yl)pyrrolidine-2-carboxamide 116C (1.111 g, 4.87 mmol) in $CH_2Cl_2$ (25.0 mL) at RT. After 14 h, the solvent was evaporated to dryness and the residue was subjected to preparative HPLC. The fractions containing the product were collected and the solvent was evaporated to dryness using speed vac. The TFA salt of the product 116D was used in the next reaction. LC/MS [M+H]$^+$: 463; Ret time (Method C): 2.23 min.

To a stirred solution of (S)-1-(4-chloro-6-(5-cyclopropyl-1H-pyrazol-3-ylamino)-1,3,5-triazin-2-yl)-4,4-difluoro-N-(pyrazin-2-yl)pyrrolidine-2-carboxamide (70 mg, 0.151 mmol) in MeOH (3 mL) was added N,N-diisopropylethylamine (0.026 mL, 0.151 mmol) followed by morpholine (39.5 mg, 0.454 mmol), and the mixture was stirred at RT for 3 hrs. The solvent was evaporated to dryness and the residue was subjected to preparative HPLC. The fractions containing the product were collected and the solvent was evaporated to dryness using speed vac. The TFA salt of the product was dissolved in methanol and placed on MCX cartridge. After washing with methanol, the free base of the product was released using a 2M ammonia solution. The solvent was evaporated to give the product 116. LC/MS [M+H]$^+$: 514; Ret time (Method C): 1.59 min.

Examples 117 to 120

Examples 117 to 120 are disclosed in Table 10 and were prepared using procedures that are described above in Example 116 starting from 116D.

TABLE 10

| Example No. | Compound | HPLC ret. time (min.) | (M + H) |
|---|---|---|---|
| 117 | 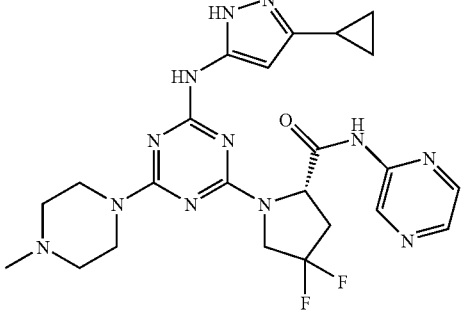(S)-1-(4-(3-Cyclopropyl-1H-pyrazol-5-ylamino)-6-(4-methylpiperazin-1-yl)-1,3,5-triazin-2-yl)-4,4-difluoro-N-(pyrazin-2-yl)pyrrolidine-2-carboxamide | 2.06 (c) | 527 |
| 118 | 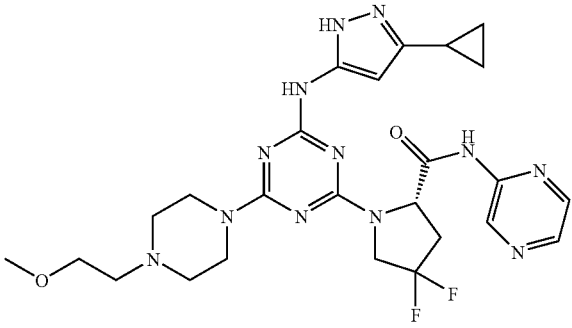 [SMILES: COCCN1CCN(c2nc(Nc3cc(C4CC4)n[nH]3)nc(N3CC(F)(F)C[C@H]3C(=O)Nc3cnccn3)n2)CC1](S)-1-(4-(3-Cyclopropyl-1H-pyrazol-5-ylamino)-6-(4-(2-methoxyethyl)piperazin-1-yl)-1,3,5-triazin-2-yl)-4,4-difluoro-N-(pyrazin-2-yl)pyrrolidine-2-carboxamide | 1.35 (a) | 572 |
| 119 | 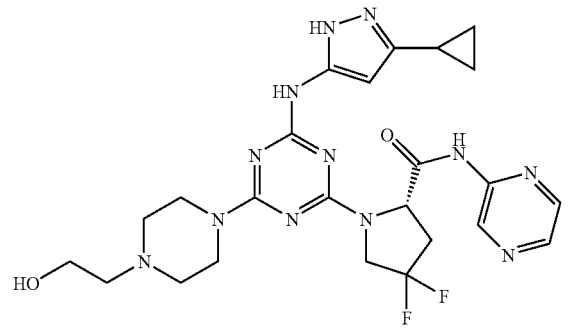 [SMILES: O=C(Nc1cnccn1)[C@@H]1CC(F)(F)CN1c1nc(Nc2cc(C3CC3)n[nH]2)nc(N2CCN(CCO)CC2)n1](S)-1-(4-(3-Cyclopropyl-1H-pyrazol-5-ylamino)-6-(4-(2-hydroxyethyl)piperazin-1-yl)-1,3,5-triazin-2-yl)-4,4-difluoro-N-(pyrazin-2-yl)pyrrolidine-2-carboxamide | 1.31 (a) | 557 |

TABLE 10-continued

| Example No. | Compound | HPLC ret. time (min.) | (M + H) |
|---|---|---|---|
| 120 | 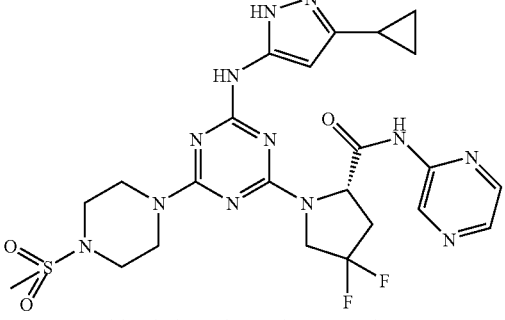<br>(S)-1-(4-(3-Cyclopropyl-1H-pyrazol-5-ylamino)-6-(4-(methylsulfonyl)piperazin-1-yl)-1,3,5-triazin-2-yl)-4,4-difluoro-N-(pyrazin-2-yl)pyrrolidine-2-carboxamide | 1.54 (a) | 591 |

Example 121

(1S,3S,5S)-2-(4-(3-Cyclopropyl-1H-pyrazol-5-ylamino)-6-morpholino-1,3,5-triazin-2-yl)-N-(pyrazin-2-yl)-2-azabicyclo[3.1.0]hexane-3-carboxamide

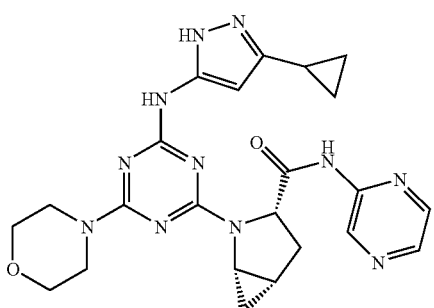 [SMILES: O=C(Nc1cnccn1)[C@@H]1C[C@@H]2C[C@@H]2N1c1nc(Nc2cc(C3CC3)n[nH]2)nc(N2CCOCC2)n1]

121A. (1S,3S,5S)-2-tert-Butyl 3-methyl 2-azabicyclo[3.1.0]hexane-2,3-dicarboxylate

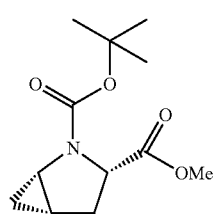 [SMILES: COC(=O)[C@@H]1C[C@@H]2C[C@@H]2N1C(=O)OC(C)(C)C]

(1S,5S)-2-tert-Butyl 3-methyl 2-azabicyclo[3.1.0]hexane-2,3-dicarboxylate 121A can be prepared from the procedures as reported in WO2004/05250.

121B. (1S,3S,5S)-tert-Butyl 3-(pyrazin-2-ylcarbamoyl)-2-azabicyclo[3.1.0]hexane-2-carboxylate

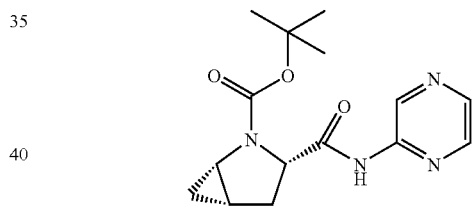

(1S,3S,5S)-tert-Butyl 3-(pyrazin-2-ylcarbamoyl)-2-azabicyclo[3.1.0]hexane-2-carboxylate 121B was prepared from 121A and 2-amino pyrazine using the procedure as reported in 65A. LC/MS [M+H]$^+$: 305; Ret time (Method A): 1.63 min.

121C. (1S,3S,5S)—N-(Pyrazin-2-yl)-2-azabicyclo[3.1.0]hexane-3-carboxamide

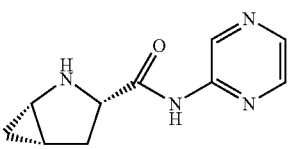 [SMILES: O=C(Nc1cnccn1)[C@@H]1C[C@@H]2C[C@@H]2N1]

Compound 121C was prepared starting from 121B using the procedure as described in 65C. LC/MS [M+H]$^+$: 205; Ret time (Method C): 0.70 min.

121D. (1S,3S,5S)-2-(4-Chloro-6-(3-cyclopropyl-1H-pyrazol-5-ylamino)-1,3,5-triazin-2-yl)-N-(pyrazin-2-yl)-2-azabicyclo[3.1.0]hexane-3-carboxamide

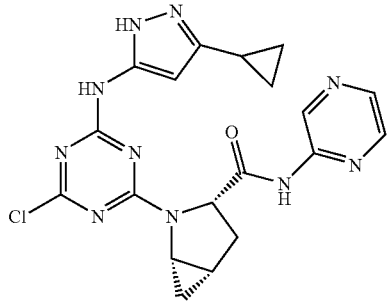 [SMILES: O=C(Nc1cnccn1)[C@@H]1C[C@@H]2C[C@@H]2N1c1nc(Cl)nc(Nc2cc(C3CC3)n[nH]2)n1]

Compound 121D was prepared from compounds 1A and 121C using the procedure as described for 1C. LC/MS [M+H]+: 439; Ret time (Method A): 1.70 min.

Compound 121 was prepared from morpholine and 121D using the procedure described for Compound 1. MS: 490 (M+H)+, HPLC (Method A) Ret time: 1.57 min.

Examples 122 and 123

Examples 122 and 123 are disclosed in Table 11 and were prepared using procedures that are described above in Example 121 starting from 121D.

TABLE 11

| Example No. | Compound | HPLC ret. Time (min.) | (M + H) |
|---|---|---|---|
| 122 | (1S,3S,5S)-2-(4-(3-Cyclopropyl-1H-pyrazol-5-ylamino)-6-(4-methylpiperazin-1-yl)-1,3,5-triazin-2-yl)-N-(pyrazin-2-yl)-2-azabicyclo[3.1.0]hexane-3-carboxamide | 1.29 (a) | 503 |
| 123 | (1S,3S,5S)-2-(4-(3-Cyclopropyl-1H-pyrazol-5-ylamino)-6-(4-(2-methoxyethyl)piperazin-1-yl)-1,3,5-triazin-2-yl)-N-(pyrazin-2-yl)-2-azabicyclo[3.1.0]hexane-3-carboxamide | 6.22 (h) | 547 |

Example 124

(2S,4S)-1-(4-(3-Cyclopropyl-1H-pyrazol-5-ylamino)-6-morpholino-1,3,5-triazin-2-yl)-4-(2,2-difluoroethoxy)-N-(thiazol-2-yl)pyrrolidine-2-carboxamide

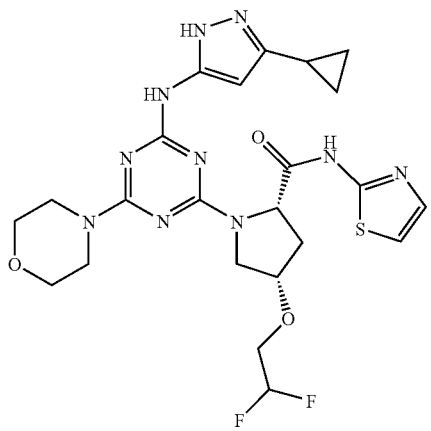 [SMILES: O=C(Nc1nccs1)[C@@H]1C[C@H](OCC(F)F)CN1c1nc(Nc2cc(C3CC3)n[nH]2)nc(N2CCOCC2)n1]

124A. (2S,4S)-1-(Benzyloxycarbonyl)-4-(2,2-difluoroethoxy)pyrrolidine-2-carboxylic acid

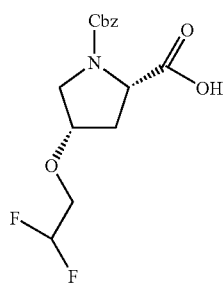 [SMILES: O=C(O)[C@@H]1C[C@H](OCC(F)F)CN1C(=O)OCc1ccccc1]

To a solution of (2S,4S)-1-(benzyloxycarbonyl)-4-hydroxypyrrolidine-2-carboxylic acid (5.0 g, 18.85 mmol) in THF (100 mL) was added NaH (1.583 g, 39.6 mmol) at 0° C. under N₂. The resulting suspension was stirred at RT for 30 min. A solution of 1,1-difluoro-2-(trifluoromethylsulfonyl)ethane (4.11 g, 20.73 mmol) in THF (5 ml) was added to the suspension. The reaction mixture was stirred at RT for 3 h. The reaction mixture was quenched with water and concentrated. The residue was extracted with EtOAc; the aqueous layers was acidified to ph 3 with 1N HCl and extracted with EtOAc. The organic layers were washed with water and brine, dried over Na₂SO₄, and filtered. The crude product was used in the next step without purification. LC/MS [M–H]⁺: 328; Ret time (Method F): 0.93 min (Phenomenex-Luna s10 4.6× 50 mm column, 4 min gradient, 4 mL/min).

124B. (2S,4S)-1-Benzyl 2-methyl 4-(2,2-difluoroethoxy)pyrrolidine-1,2-dicarboxylate

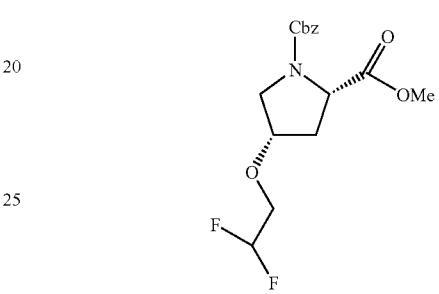

To a solution of (2S,4S)-1-(benzyloxycarbonyl)-4-(2,2-difluoroethoxy)pyrrolidine-2-carboxylic acid (2.0 g, 6.07 mmol) in MeOH and ether (80 ml) (1:1) was added TMS-diazomethane (4.56 mL, 9.11 mmol) (2.0M solution in ether) dropwise at 0° C. The reaction mixture was stirred at RT for 1 h and concentrated. The residue was used in the next step.

124C. (2S,4S)-Methyl 4-(2,2-difluoroethoxy)pyrrolidine-2-carboxylate

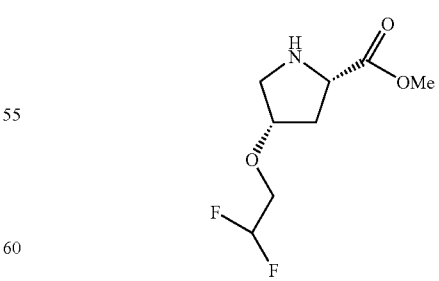

To nitrogen flushed pressure bottle was added Pd/c (200 mg) under nitrogen. A solution of (2S,4S)-1-benzyl 2-methyl 4-(2,2-difluoroethoxy)pyrrolidine-1,2-dicarboxylate (2.0 g, 5.83 mmol) in MeOH (140 mL) was added to the bottle. The reaction mixture was hydrogenated at 50 psi overnight. The reaction mixture was passed through a pad of celite and washed with MeOH. The filtrate was concentrated and the residue was used for the next step without purification. $^1$H NMR (CDCl$_3$, 400 MHz) δ ppm 3.56-3.79 (1H, m), 3.96 (1H, br s), 3.60-3.70 (1H, m), 3.62 (3H, s), 3.43-3.50 (2H, m), 3.07-3.09 (1H, m), 2.94-3.03 (1H, m), 2.78-2.87 (1H, m), 2.05-2.15 (2H, m); $^{13}$C NMR (126 MHz, CDCl$_3$) δ ppm 174.72 (1C), 114.40 (1C, t, J=241 Hz), 80.41 (1C), 67.96 (1C, t, J=27.6 Hz), 58.78 (1C), 52.40 (1C), 52.29 (1C), 52.19 (1C, s), 35.96 (1C).

124D. (1R,4R)-Methyl 2-(4-chloro-6-(3-cyclopropyl-1H-pyrazol-5-ylamino)-1,3,5-triazin-2-yl)-4-(2,2-difluoroethoxy)cyclopentanecarboxylate

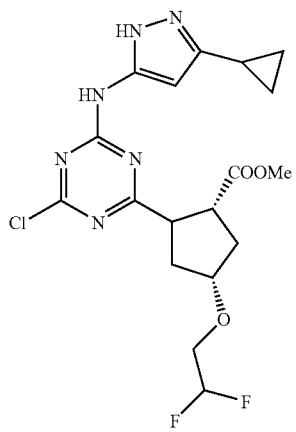 [SMILES: COC(=O)[C@@H]1C[C@H](OCC(F)F)CC1c1nc(Cl)nc(Nc2cc(C3CC3)n[nH]2)n1]

124D was prepared using the procedure described in 1C. LC/MS [M+H]$^+$: 444/446; Ret time (Method F): 2.80 min.

124E. (1R,4R)-Methyl 2-(4-(3-cyclopropyl-1H-pyrazol-5-ylamino)-6-morpholino-1,3,5-triazin-2-yl)-4-(2,2-difluoroethoxy)cyclopentanecarboxylate

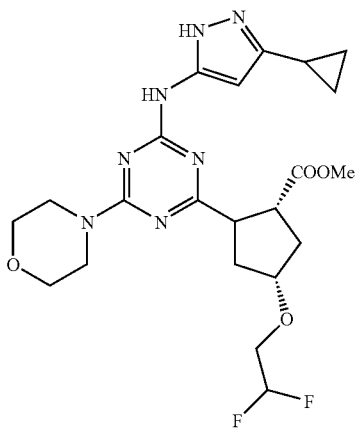 [SMILES: COC(=O)[C@@H]1C[C@H](OCC(F)F)CC1c1nc(Nc2cc(C3CC3)n[nH]2)nc(N2CCOCC2)n1]

124E was prepared from morpholine and 124D using the procedure described in 1. LC/MS [M+H]$^+$: 495; Ret time (Method F): 2.61 min.

To a solution of thiazol-2-amine (153 mg, 1.341 mmol) in THF (10 mL) was added isopropylmagnesium chloride (115 mg, 1.117 mmol) at 0° C. under N$_2$. The reaction mixture was stirred at RT for 10 min. A solution of (2S,4S)-methyl 1-(4-(5-cyclopropyl-1H-pyrazol-3-ylamino)pyrrolo[1,2-f][1,2,4]triazin-2-yl)-4-(2,2-difluoroethoxy)pyrrolidine-2-carboxylate (50 mg, 0.112 mmol) in THF (3 ml) was added. The reaction mixture was stirred at RT for 4 h, quenched with TFA/MeOH, and concentrated. The residue was purified by prep. HPLC. The fractions containing the product were collected and the solvent was evaporated to dryness using speed vac. The TFA salt of the product was dissolved in methanol and placed on MCX cartridge. After washing with methanol, the free base of the product was released using a 2M ammonia solution. Removal of the solvents furnished 124 (43 mg, 72%). LC/MS [M+H]$^+$: 563; Ret time (Method F): 3.21 min.

Examples 125 and 126

Examples 125 and 126 are disclosed in Table 12 and were prepared using procedures that are described above in Example 124 starting from 124E.

TABLE 12
| Example No. | Compound | HPLC ret. time (min.) | (M + H) |
|---|---|---|---|
| 125 | 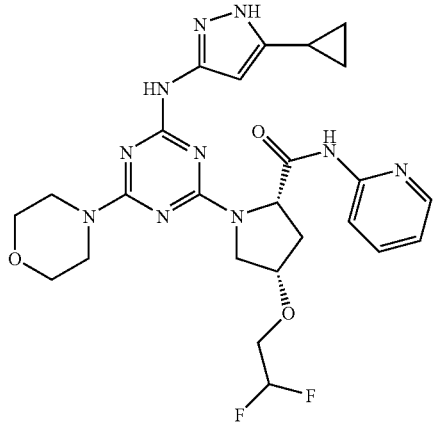 [SMILES: O=C(Nc1ccccn1)[C@@H]1C[C@H](OCC(F)F)CN1c1nc(Nc2cc(C3CC3)[nH]n2)nc(N2CCOCC2)n1]<br>(2S,4S)-1-(4-(5-cyclopropyl-1H-pyrazol-3-ylamino)-6-morpholino-1,3,5-triazin-2-yl)-4-(2,2-difluoroethoxy)-N-(pyridin-2-yl)pyrrolidine-2-carboxamide | 2.52 (f) | 557 |
| 126 | 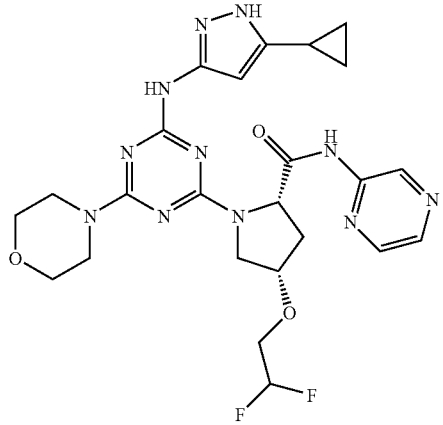 [SMILES: O=C(Nc1cnccn1)[C@@H]1C[C@H](OCC(F)F)CN1c1nc(Nc2cc(C3CC3)[nH]n2)nc(N2CCOCC2)n1]<br>(2S,4S)-1-(4-(5-Cyclopropyl-1H-pyrazol-3-ylamino)-6-morpholino-1,3,5-triazin-2-yl)-4-(2,2-difluoroethoxy)-N-(pyrazin-2-yl)pyrrolidine-2-carboxamide | 2.57 (f) | 558 |

Example 127

(S)-1-(4-(5-Cyclopropyl-1H-pyrazol-3-ylamino)-6-morpholino-1,3,5-triazin-2-yl)-N-(pyrazin-2-yl)azetidine-2-carboxamide

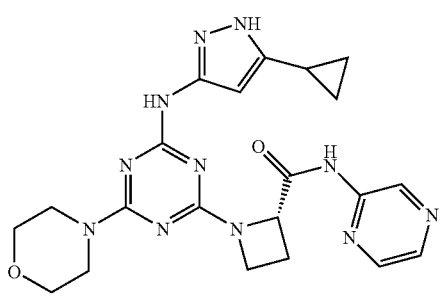 [SMILES: O=C(Nc1cnccn1)[C@@H]1CCN1c1nc(Nc2cc(C3CC3)[nH]n2)nc(N2CCOCC2)n1]

127A. (S)-tert-Butyl 2-(pyrazin-2-ylcarbamoyl)azetidine-1-carboxylate

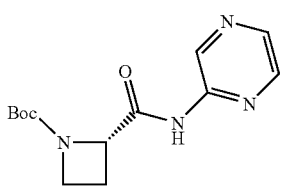 [SMILES: CC(C)(C)OC(=O)N1CC[C@H]1C(=O)Nc1cnccn1]

To a stirred solution of pyrazin-2-amine (1.626 g, 17.10 mmol) in THF (40 mL) was added isopropylmagnesium chloride (8.44 mL, 16.88 mmol) at 0° C. under $N_2$. The resulting slurry was stirred at RT for 30 min. A solution of (S)-1-tert-butyl 2-methyl azetidine-1,2-dicarboxylate (0.92 g, 4.27 mmol) in THF (5 ml) was added to the reaction slurry. The reaction mixture was stirred at RT for 4 h. and concentrated. The residue was dissolved in EtOAc and washed with 1N HCl, water, and brine. The organic layer was dried over $Na_2SO_4$ and filtered. The crude product (1.05 g, 88%) was used in the next step without purification. $^1$H NMR (400 MHz, MeOD) δ ppm 1.38 (s, 9H) 2.31 (br s, 1H) 2.53 (ddd, J=8.81, 6.17, 2.39 Hz, 1H) 3.89-4.00 (m, 2H) 4.81-4.86 (m, 1H) 8.30-8.37 (m, 2H) 9.41 (s, 1H); LC/MS [M+H]$^+$: 279; Ret time (Method F): 2.27 min.

127B. (S)—N-(Pyrazin-2-yl)azetidine-2-carboxamide

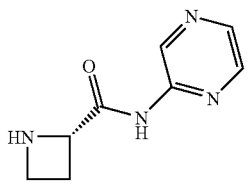 [SMILES: O=C(Nc1cnccn1)[C@@H]1CCN1]

To a stirred solution of (S)-tert-butyl 2-(pyrazin-2-ylcarbamoyl)azetidine-1-carboxylate (1.05 g, 3.77 mmol) in $CH_2Cl_2$ (40 mL) was added TFA (1.453 mL, 18.86 mmol). The reaction mixture was stirred at RT overnight and concentrated. The residue was used for the next step without purification. LC/MS [M+H]$^+$: 179; Ret time (Method F): 0.29 min.

127C. (S)-1-(4-Chloro-6-(3-cyclopropyl-1H-pyrazol-5-ylamino)-1,3,5-triazin-2-yl)-N-(pyrazin-2-yl)azetidine-2-carboxamide

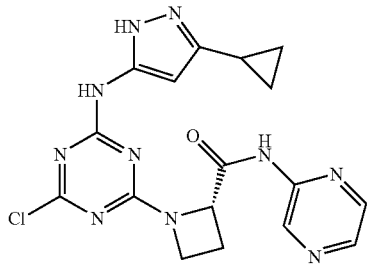 [SMILES: O=C(Nc1cnccn1)[C@@H]1CCN1c1nc(Cl)nc(Nc2cc(C3CC3)n[nH]2)n1]

To a stirred solution of 4,6-dichloro-N-(5-cyclopropyl-1H-pyrazol-3-yl)-1,3,5-triazin-2-amine (0.85 g, 3.14 mmol) and N-ethyl-N-isopropylpropan-2-amine (1.216 g, 9.41 mmol) in Solvent 1 (25 mL) was added (S)—N-(pyrazin-2-yl)azetidine-2-carboxamide (0.559 g, 3.14 mmol) at 0° C. The reaction mixture was stirred at RT for 2 h. The crude reaction solution was used in the next step without purification. LC/MS [M+H]$^+$: 413; Ret time (Method F): 2.39 min.

One fifth of the reaction mixture was put in a flask and morpholine (0.5 ml, excess) was added to the reaction mixture. The reaction mixture was stirred at RT for 2 h and concentrated. The residue was dissolved in MeOH and the solid was filtered off. The crude product was purified by prep. HPLC. The fractions containing the product were collected and the solvent was evaporated to dryness using speed vac. The TFA salt of the product was dissolved in methanol and placed on MCX cartridge. After washing with methanol, the free base of the product was released using 2M ammonia solution. Removal of the solvents furnished 127 (84 mg, 26%). LC/MS [M+H]$^+$: 464; Ret time (Method F): 2.45 min.

Examples 128 to 130

Examples 128 to 130 are disclosed in Table 13 and were prepared using procedures that are described above in Example 127 starting from 127C.

TABLE 13

| Example No. | Compound | HPLC ret. time (min.) | (M + H) |
|---|---|---|---|
| 128 | (S)-1-(4-(5-Cyclopropyl-1H-pyrazol-3-ylamino)-6-(4-methylpiperazin-1-yl)-1,3,5-triazin-2-yl)-N-(pyrazin-2-yl)azetidine-2-carboxamide | 1.83 (f) | 477 |
| 129 | (S)-1-(4-(5-Cyclopropyl-1H-pyrazol-3-ylamino)-6-(4-(2-methoxyethyl)piperazin-1-yl)-1,3,5-triazin-2-yl)-N-(pyrazin-2-yl)azetidine-2-carboxamide | 1.92 (f) | 521 |

TABLE 13-continued

| Example No. | Compound | HPLC ret. time (min.) | (M + H) |
|---|---|---|---|
| 130 | 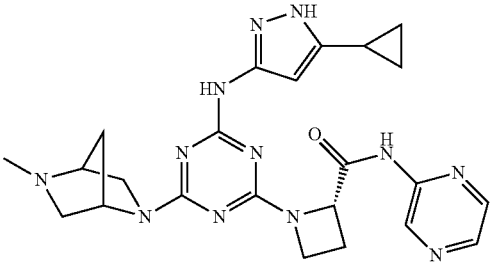 [SMILES: CN1CC2CC1CN2c1nc(Nc2cc(C3CC3)[nH]n2)nc(N2CC[C@H]2C(=O)Nc2cnccn2)n1]<br>(2S)-1-(4-(5-Cyclopropyl-1H-pyrazol-3-ylamino)-6-(5-methyl-2,5-diazabicyclo[2.2.1]heptan-2-yl)-1,3,5-triazin-2-yl)-N-(pyrazin-2-yl)azetidine-2-carboxamide | 1.87 (f) | 487 |

We claim:

1. A compound of the formula

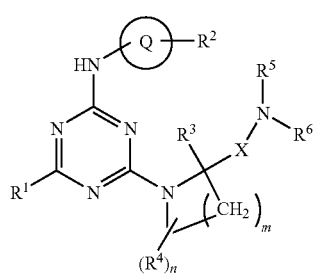

(I)

wherein:

Q is aryl, substituted aryl, heteroaryl or substituted heteroaryl;

X is C=O, C=S or CH$_2$;

R$^1$ is alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

R$^2$ is hydrogen, alkyl, substituted alkyl, cycloalkyl or substituted cycloalkyl;

R$^3$ is hydrogen, alkyl or substituted alkyl;

R$^4$ is independently one or more hydrogen, alkyl, substituted alkyl, hydroxy, alkoxy, halogen, haloalkyl, haloalkoxy, cycloalkyl or substituted cycloalkyl;

R$^5$ and R$^6$ are independently hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or R$^5$ and R$^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

m is 1, 2 or 3;

n is 0, 1, 2, 3 or 4;

or a pharmaceutically acceptable salt, tautomer or stereoisomer thereof.

2. The compound according to claim 1 of the formula

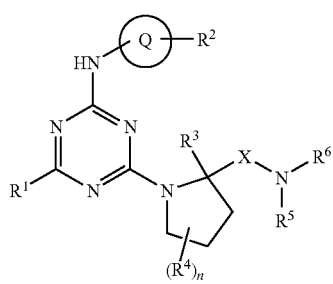

(Ia)

wherein:

Q is heteroaryl or substituted heteroaryl;

X is C=O or C=S;

R$^1$ is alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, substituted amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^2$ is hydrogen, alkyl, substituted alkyl, cycloalkyl or substituted cycloalkyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ is hydrogen;

$R^6$ is hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

n is 0, 1, 2, 3 or 4;

or a pharmaceutically acceptable salt, tautomer or stereoisomer thereof.

3. The compound according to claim 2 of the formula

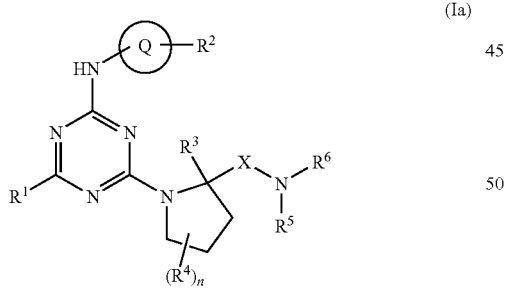

(Ia)

wherein:
Q is heteroaryl;
X is C=O;
$R^1$ is alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^2$ is hydrogen, alkyl, substituted alkyl, cycloalkyl or substituted cycloalkyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ is hydrogen;

$R^6$ is hydrogen, alkyl, substituted alkyl, cycloalkyl, substituted cycloalkyl, aryl, substituted aryl, heteroaryl, substituted heteroaryl, heterocycloalkyl, substituted heterocycloalkyl, heteroalkyl, substituted heteroalkyl, heteroalkenyl, substituted heteroalkenyl, heteroalkynyl, or substituted heteroalkynyl; or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring;

n is 0, 1 or 2;

or a pharmaceutically acceptable salt, tautomer or stereoisomer thereof.

4. The compound according to claim 3

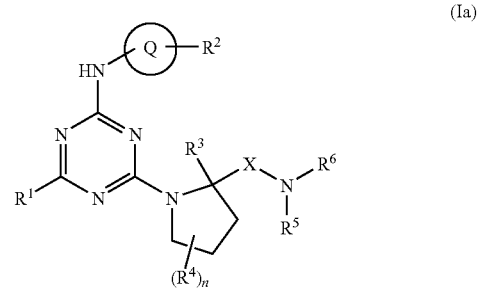

(Ia)

wherein:
Q is pyrazole or imidazole;
X is C=O;
$R^1$ is alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^2$ is hydrogen, alkyl, substituted alkyl, cycloalkyl or substituted cycloalkyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ is hydrogen;

$R^6$ is pyridine, substituted pyridine, pyrazine, substituted pyrazine, thiadiazole, thiazole;

substituted thiazole, piperidine or substituted piperidine, or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring, n is 0, 1 or 2;

or a pharmaceutically acceptable salt, tautomer or stereoisomer thereof.

5. A compound of the formula

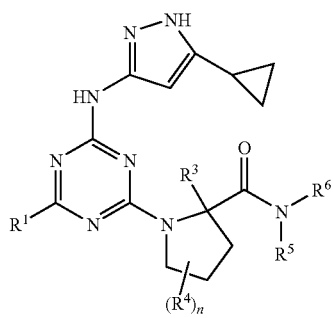

(II)

wherein:

$R^1$ is alkyl, substituted alkyl, hydroxy, alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino, or alkylaminocarbonyl;

$R^3$ is hydrogen, alkyl or substituted alkyl;

$R^4$ is independently one or more hydrogen, alkyl, substituted alkyl, hydroxy, alkoxy, halogen, haloalkyl, haloalkoxy, cycloalkyl or substituted cycloalkyl;

$R^5$ is hydrogen;

$R^6$ is pyridine, substituted pyridine, pyrazine, substituted pyrazine, thiadiazole, thiazole;

substituted thiazole, piperidine or substituted piperidine, or $R^5$ and $R^6$ are taken together with the nitrogen atom to which they are attached to form an optionally substituted monocyclic 4-8 membered saturated or unsaturated carbocyclic or heterocyclic ring, or an optionally substituted bicyclic 7-12 membered saturated or unsaturated carbocyclic or heterocyclic ring, n is 0, 1 or 2;

or a pharmaceutically acceptable salt, tautomer or stereoisomer thereof.

6. A pharmaceutical composition comprising a pharmaceutically acceptable carrier and one or more compounds of claim 1 or pharmaceutically acceptable salts or stereoisomers thereof.

7. A pharmaceutical composition comprising a pharmaceutically acceptable carrier and one or more compounds of claim 1 or pharmaceutically acceptable salts or stereoisomers thereof in combination with one or more other anti-cancer or cytotoxic agents.

8. A pharmaceutical composition comprising a pharmaceutically acceptable carrier and one or more compounds of claim 2 or pharmaceutically acceptable salts or stereoisomers thereof.

9. A pharmaceutical composition comprising a pharmaceutically acceptable carrier and one or more compounds of claim 3 or pharmaceutically acceptable salts or stereoisomers thereof.

10. A pharmaceutical composition comprising a pharmaceutically acceptable carrier and one or more compounds of claim 5 or pharmaceutically acceptable salts or stereoisomers thereof.

11. A method for the treatment of cancer, comprising administering to a patient in need thereof a therapeutically effective amount of a compound of claim 1 or stereoisomers or pharmaceutically acceptable salts thereof.

12. A method for the treatment of cancer, comprising administering to a patient in need thereof a therapeutically effective amount of a compound of claim 5 or stereoisomers or pharmaceutically acceptable salts thereof.

13. The method of claim 11 wherein the cancer is carcinoma of the prostate, pancreatic ductal adreno-carcinoma, breast, colon, lung, ovary, pancreas or thyroid cancer, neuroblastoma, glioblastoma, medulloblastoma, melanoma, multiple myeloma, or acute myelogenous leukemia (AML).

14. The method of claim 12 wherein the cancer is carcinoma of the prostate, pancreatic ductal adreno-carcinoma, breast, colon, lung, ovary, pancreas or thyroid cancer, neuroblastoma, glioblastoma, medulloblastoma, melanoma, multiple myeloma, or acute myelogenous leukemia (AML).

* * * * *